United States Patent
Apple et al.

(10) Patent No.: US 6,494,824 B1
(45) Date of Patent: Dec. 17, 2002

(54) MEDICAL, RADIOTHERAPY SOURCE VIAL

(75) Inventors: Marc G. Apple, 1606 Sycamore Hills Dr., Fort Wayne, IN (US) 47906; Brian L. Bates, Bloomington, IN (US); John A. DeFord, Bloomington, IN (US); Neal E. Fearnot, West Lafayette, IN (US); James D. Purdy, Lafayette, IN (US); Joseph P. Lane, Bloomington, IN (US); Delbert C. Miller, Bloomington, IN (US); Gregory A. Frankland, Unionville, IN (US)

(73) Assignee: Marc G. Apple, Ft. Wayne, IN (US)

( * ) Notice: Subject to any disclaimer, the term of this patent is extended or adjusted under 35 U.S.C. 154(b) by 0 days.

(21) Appl. No.: 09/253,310

(22) Filed: Feb. 20, 1999

Related U.S. Application Data

(60) Provisional application No. 60/075,284, filed on Feb. 20, 1998.

(51) Int. Cl.[7] ............................................. A61N 05/00
(52) U.S. Cl. ........................................................ 600/3
(58) Field of Search ................................ 600/1, 3, 4, 5, 600/7

(56) References Cited

U.S. PATENT DOCUMENTS 3,673,411 A    6/1972 Glasser (List continued on next page.)

FOREIGN PATENT DOCUMENTS

WO    9912609    3/1999

OTHER PUBLICATIONS

A Calibrated Dose Dispenser for Gaseous $^{133}$Xe; Gutkowski et al.; Journal of Nuclear Medicine; Dec., 1975, vol. 16 No. 12.

*Primary Examiner*—Kevin Shaver
*Assistant Examiner*—Joseph A. Cadugan
(74) *Attorney, Agent, or Firm*—Baker, Donelson, Bearman & Caldwell

(57) ABSTRACT

A catheter apparatus and radiation dosimetry unit indicator for delivery of a prescribed radiation dose to a patient. A radiotherapy source vial (700) includes a fluid container (701) of radioactive fluid with a seal (702,731) disposed about the container. Seal (702,731) is moveable with respect to container (701) to change the contained volume therein. A radioactive fluid transport site (703) is in communication with the contained volume and with an exterior (726) of the container (701), and may include a septum (707) or a valve (711). An engagement mechanism (704) is connectable to an external control mechanism (706) whereby the contained volume in the radioactive fluid container can be decreased and increased by actuation of the external control mechanism.

20 Claims, 33 Drawing Sheets

U.S. PATENT DOCUMENTS

| | | |
|---|---|---|
| 3,848,773 A | 11/1974 | Adler et al. |
| 4,029,104 A | 6/1977 | Kerber |
| 4,192,438 A | 3/1980 | Foster et al. |
| 4,208,588 A | 6/1980 | Rudin |
| 4,254,774 A | 3/1981 | Boretos |
| 4,328,811 A | 5/1982 | Fogarty |
| 4,497,349 A | 2/1985 | Farley |
| 4,565,301 A | 1/1986 | Hubbard et al. |
| 4,615,468 A | 10/1986 | Gay |
| 4,654,027 A | 3/1987 | Dragan et al. |
| 4,801,047 A | 1/1989 | Klatte et al. |
| 4,808,165 A | 2/1989 | Carr |
| 4,815,449 A | 3/1989 | Horowitz |
| 4,823,167 A | 4/1989 | Manska et al. |
| 5,087,247 A | 2/1992 | Horn et al. |
| 5,112,305 A | 5/1992 | Barath et al. |
| 5,227,969 A | 7/1993 | Waggener et al. |
| 5,423,744 A | 6/1995 | Gencheff et al. |
| 5,427,104 A | 6/1995 | Briend et al. |
| 5,429,582 A | 7/1995 | Williams |
| 5,458,571 A | 10/1995 | Lampropoulos et al. |
| 5,464,395 A | 11/1995 | Faxon et al. |
| 5,484,384 A | 1/1996 | Fearnot |
| 5,485,835 A | 1/1996 | Vande Streek et al. |
| 5,503,613 A | 4/1996 | Weinberger |
| 5,528,652 A | 6/1996 | Smith et al. |
| 5,536,241 A | 7/1996 | Zapol |
| 5,540,659 A | 7/1996 | Teirstein |
| 5,556,389 A | 9/1996 | Liprie |
| 5,571,086 A | 11/1996 | Kaplan et al. |
| 5,616,114 A | 4/1997 | Thornton et al. |
| 5,618,266 A | 4/1997 | Liprie |
| 5,716,317 A | 2/1998 | Okano et al. |
| 5,916,143 A | 6/1999 | Apple et al. |
| 5,947,890 A | 9/1999 | Spencer et al. |
| 5,961,439 A * | 10/1999 | Chernomorsky et al. ...... 600/4 |

* cited by examiner

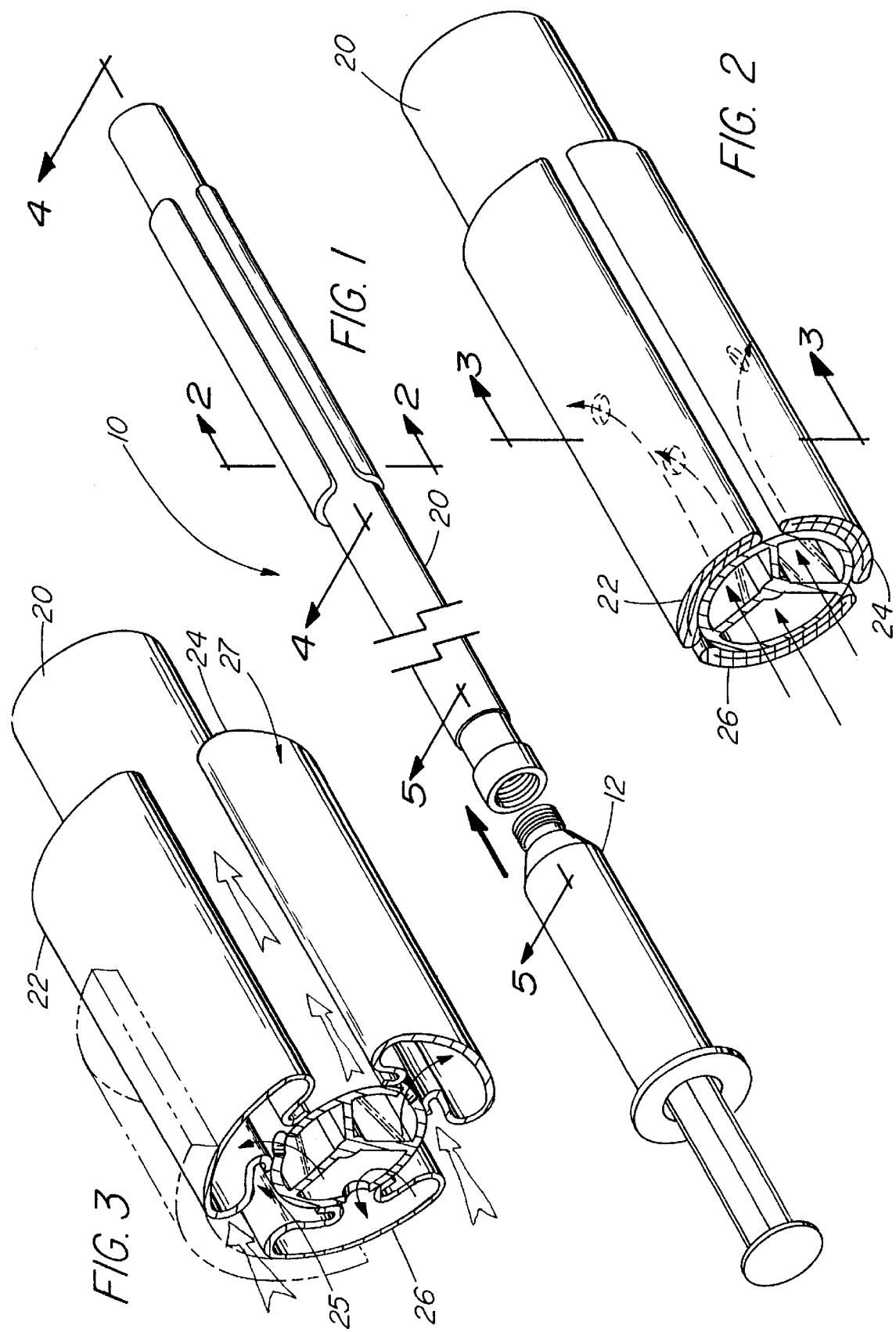

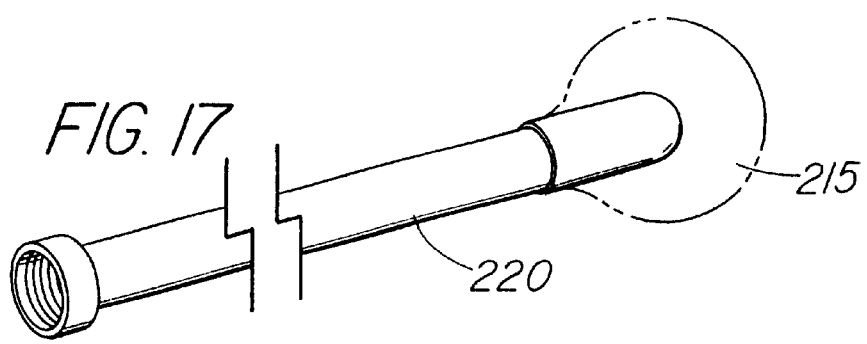
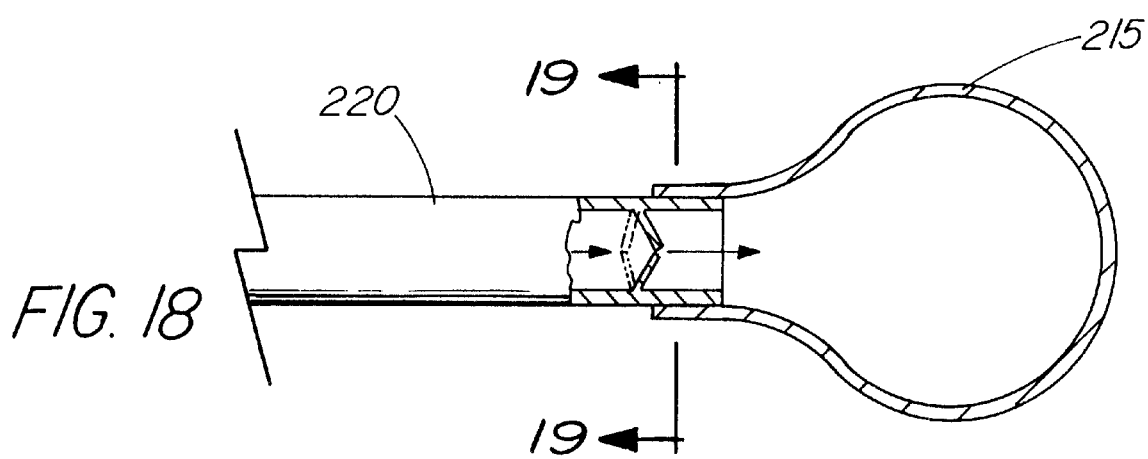
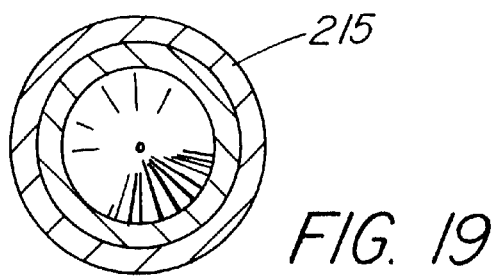

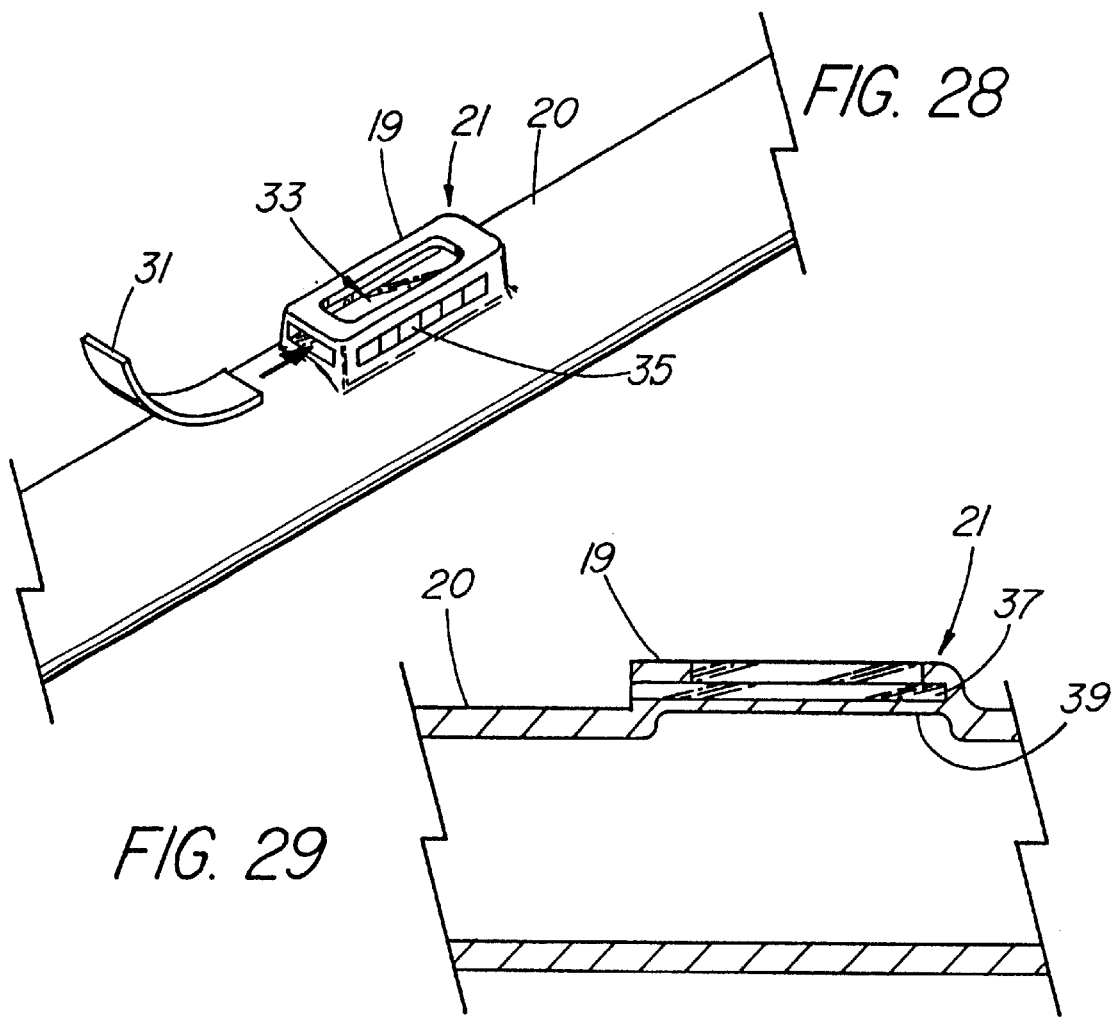
FIG. 28
FIG. 29
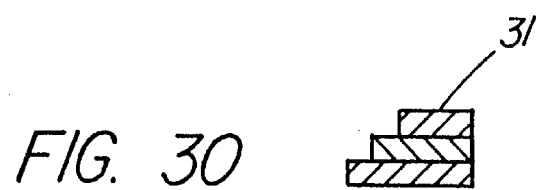
FIG. 30
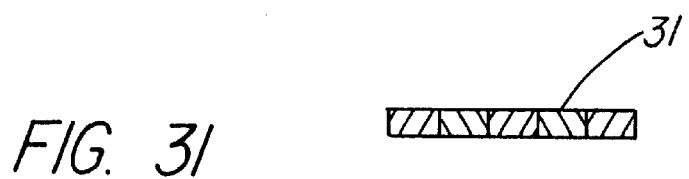
FIG. 31

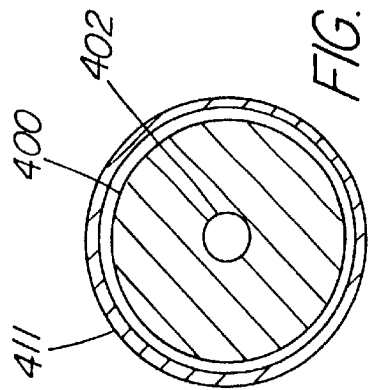
FIG. 41
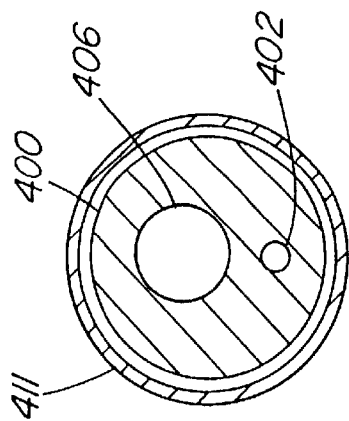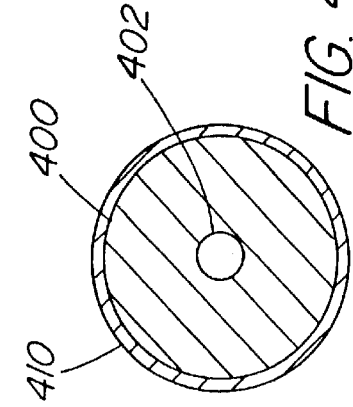
FIG. 38
FIG. 40
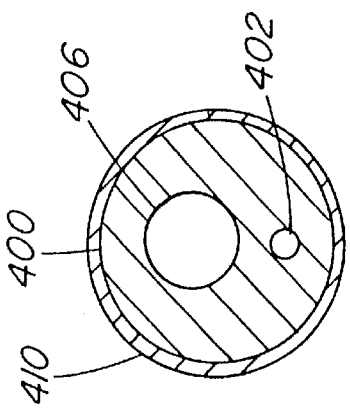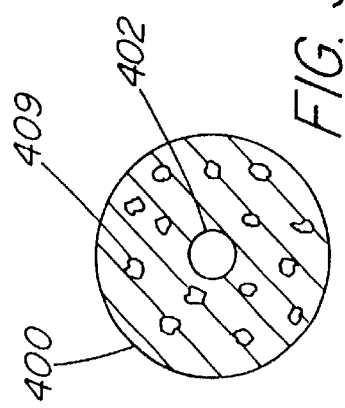
FIG. 37
FIG. 39
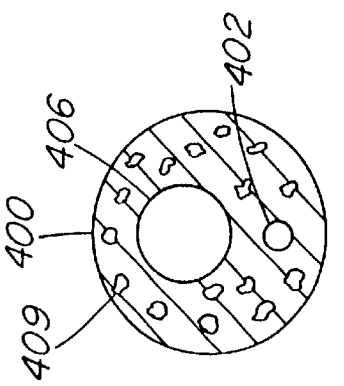
FIG. 36

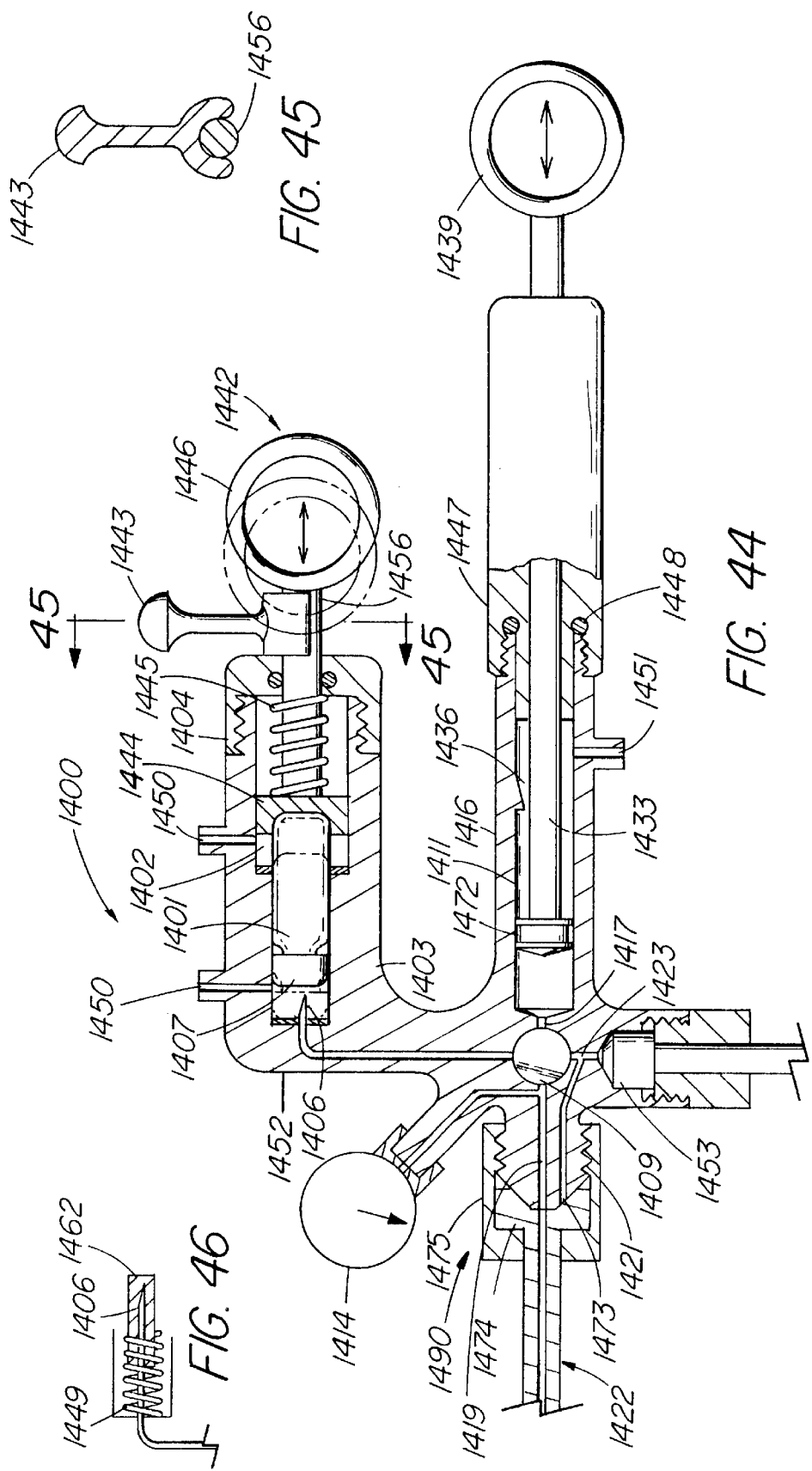

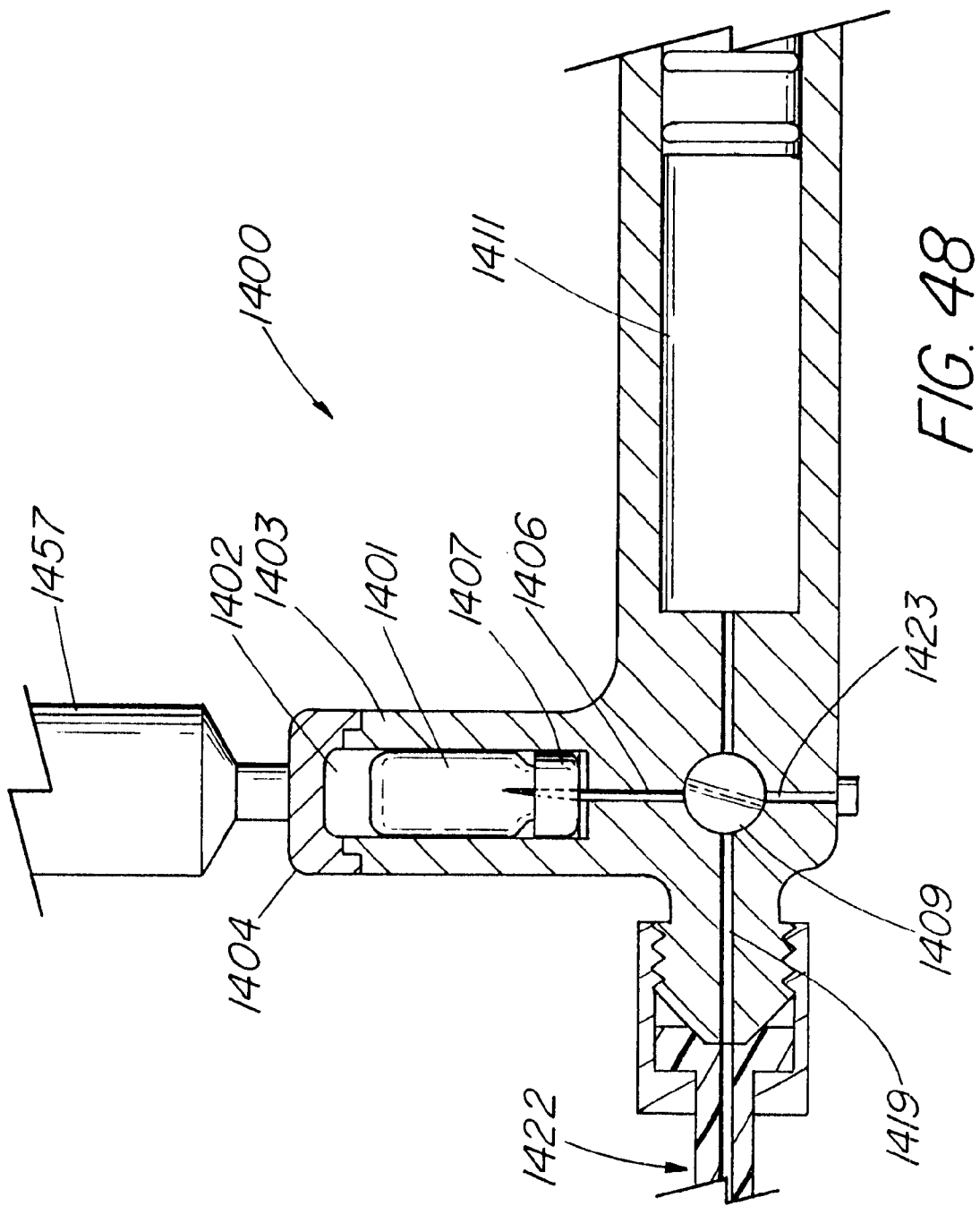

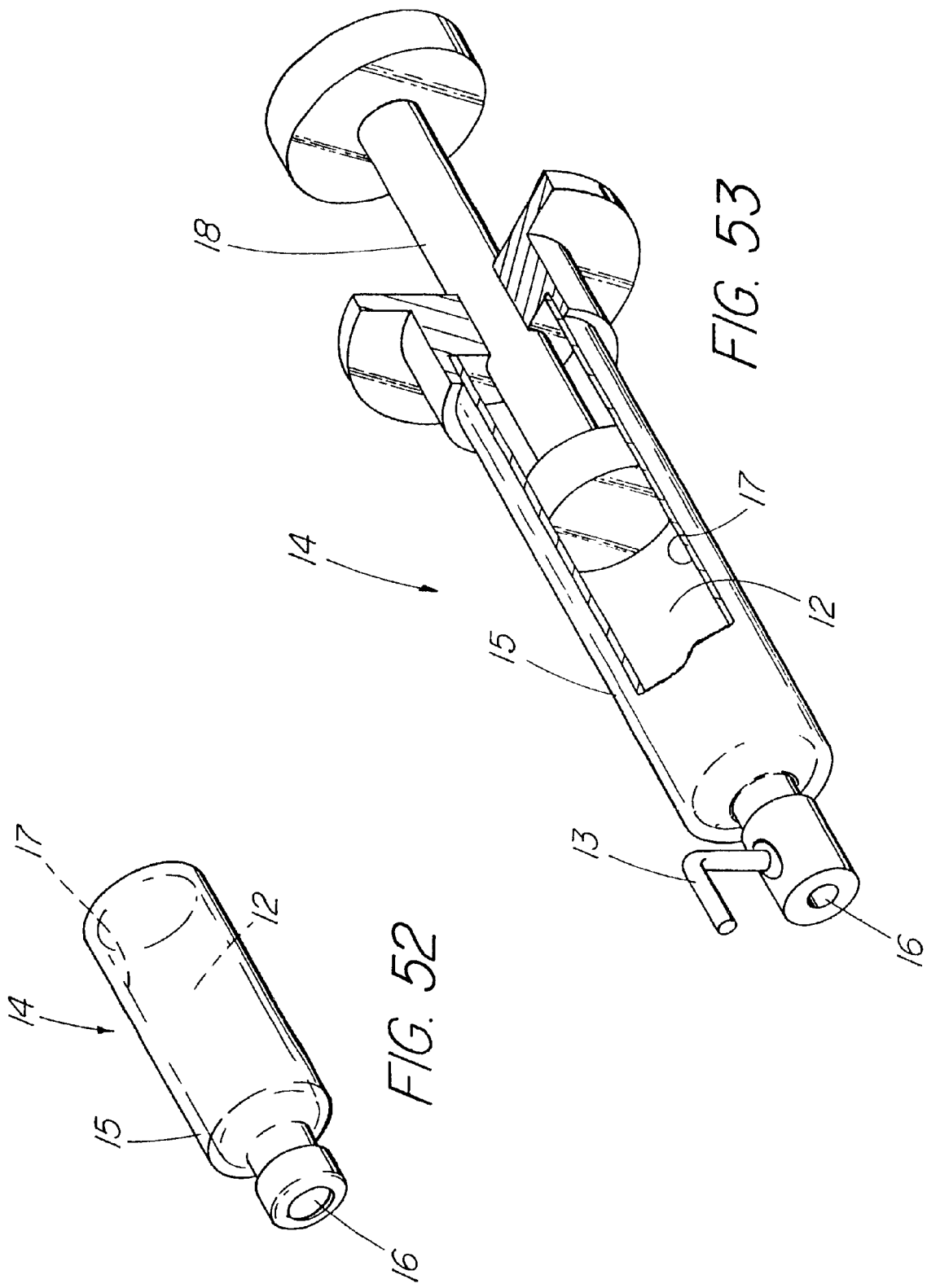

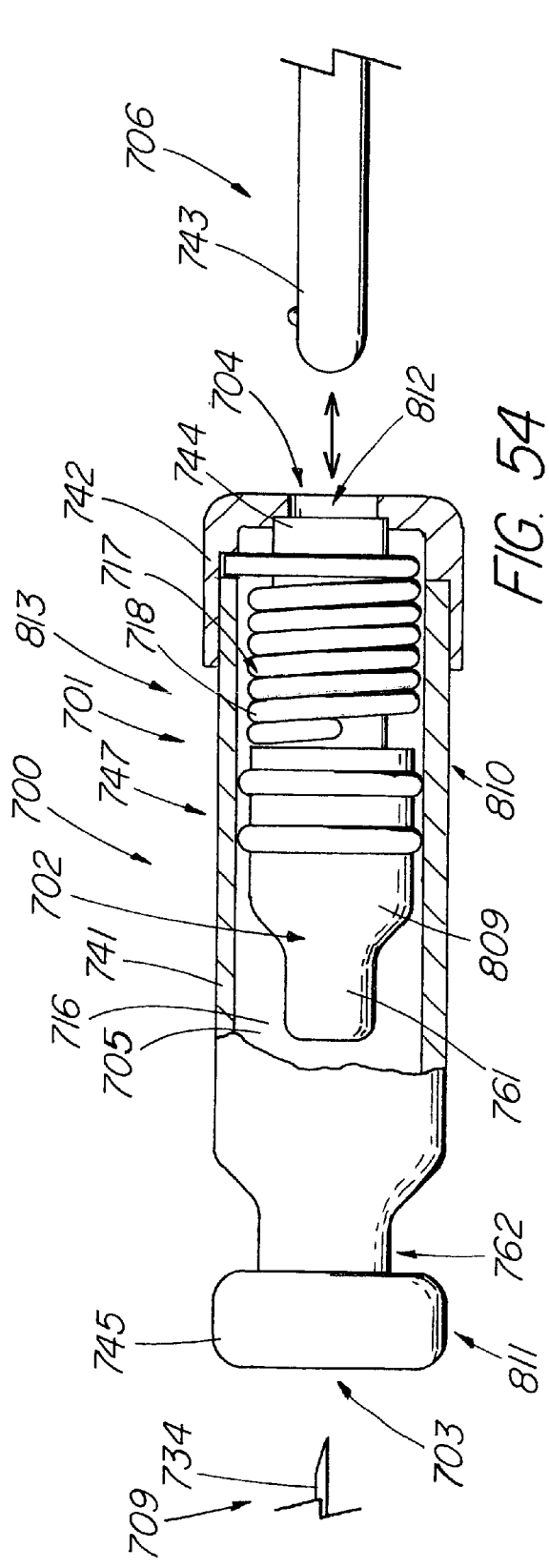
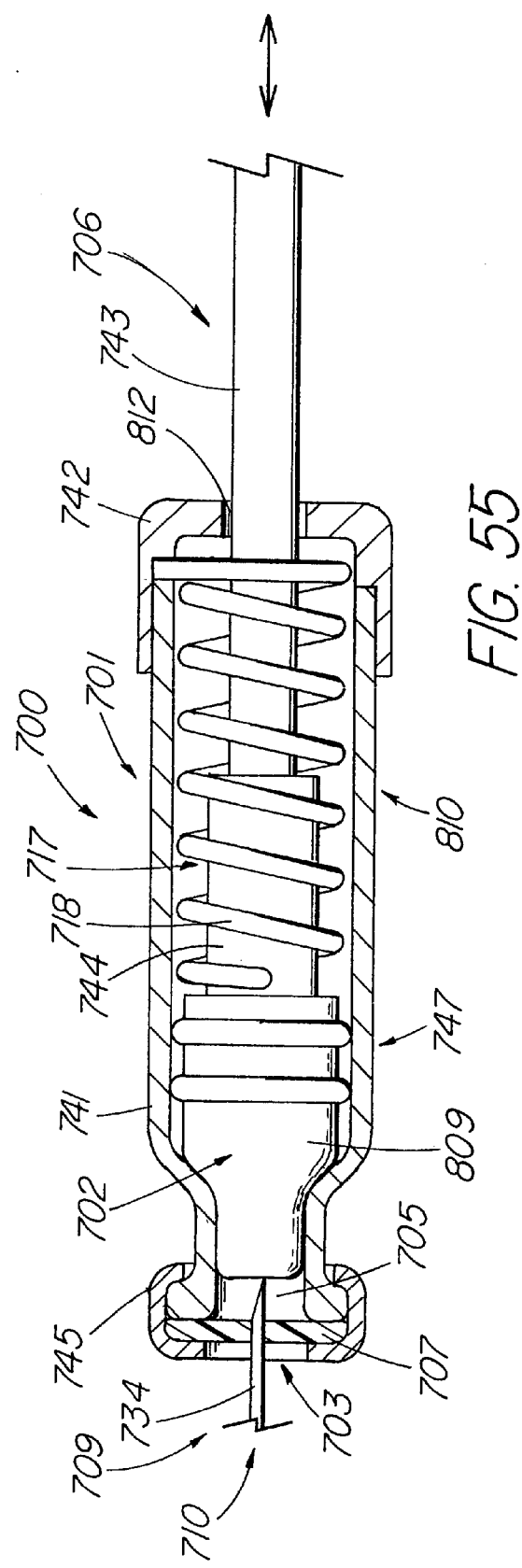

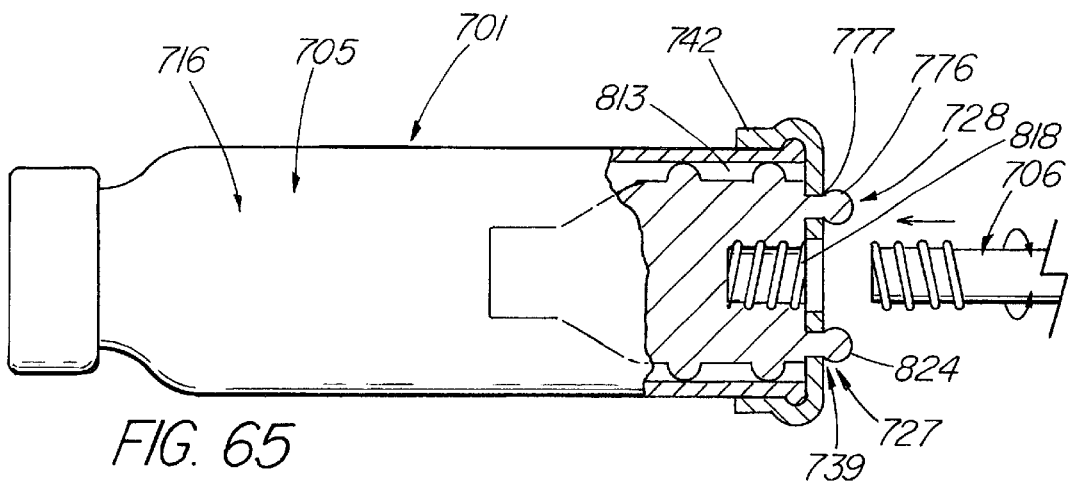
FIG. 65
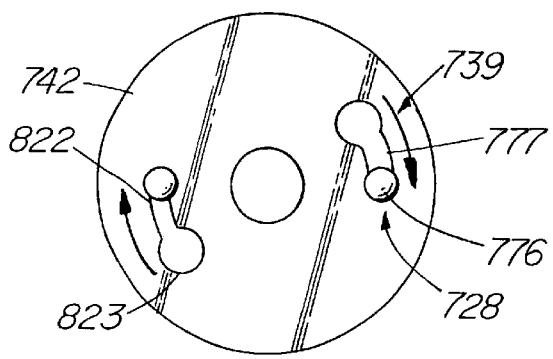
FIG. 66
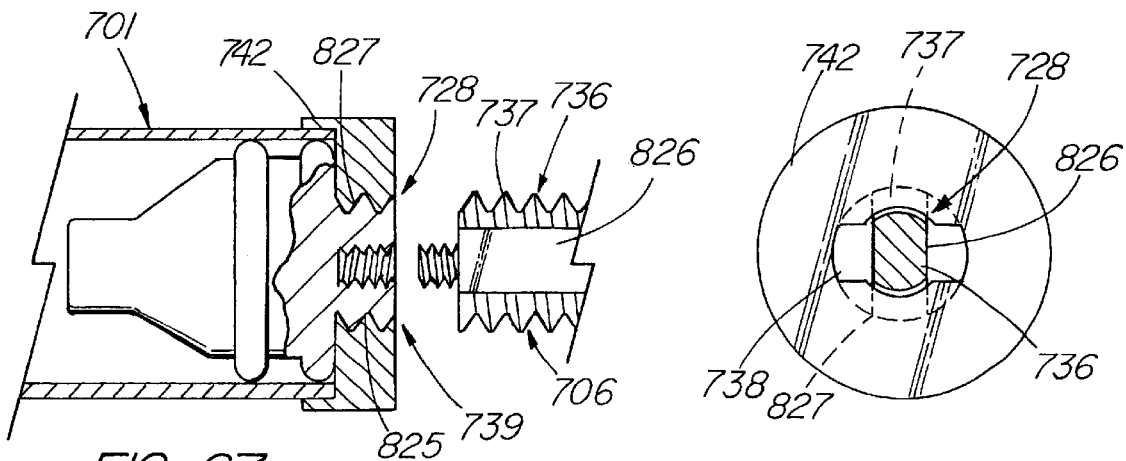
FIG. 67
FIG. 68

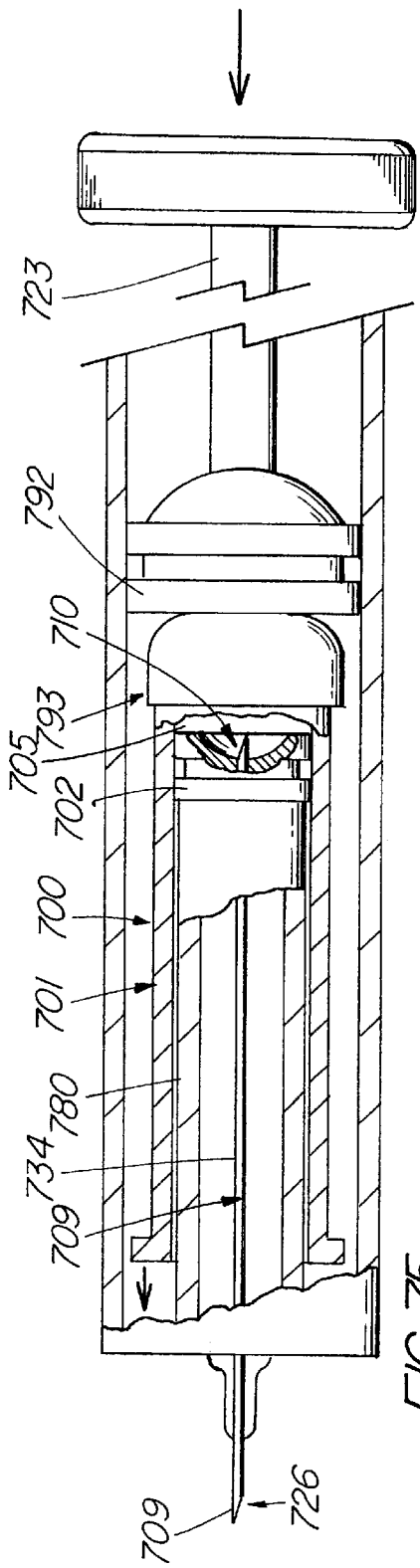
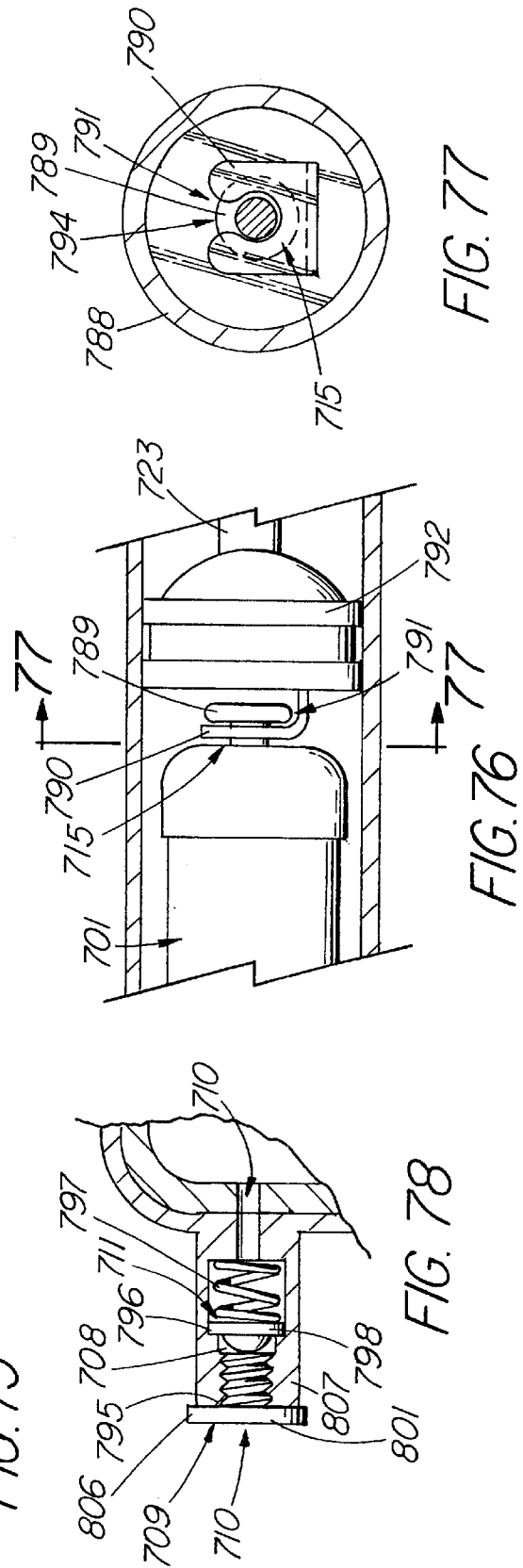
FIG. 75
FIG. 76
FIG. 77
FIG. 78

MEDICAL, RADIOTHERAPY SOURCE VIAL

CROSS REFERENCE TO RELATED APPLICATIONS

This application claims priority of provisional application Ser. No. 60/075,284, filed Feb. 20, 1998.

TECHNICAL FIELD

This invention relates generally to medical devices and, in particular, to a medical, radiotherapy source vial for containing a prescribed radiation dose for a patient.

BACKGROUND OF THE INVENTION

Angioplasty is an established procedure for reducing the effect of atherosclerotic plaque on and intraluminal narrowing of the arterial walls within the vascular system of the patient. The effect is reduced by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, as many as one-third to one-half of the patients soon develop restenosis. Restenosis can occur after angioplasty or other recannulation procedures, with or without stenting, wherein the migration and proliferation of benign cells cause a restenotic lesion to form, resulting in the further blockage of the intravascular structure.

Radiation is administered to patients for a variety of reasons, such as to treat restenosis, malignant or benign tumors, or the like. Examples of such treatments are disclosed in U.S. Pat. Nos. 5,059,166; 5,213,561; and 5,302,168.

It would be preferred to be able to provide a radiation delivery system which would:

a) deliver a predetermined totally-cumulative and homogeneous dose of radiation to the lesion site, at a predetermined penetration depth, while minimizing the exposure of surrounding healthy tissue to the radiation;

b) enable the treating physician or other health-care personnel to be bedside to the patient during the administration of the radiation therapy without exposing the physician or health care personnel to any unreasonable risk;

c) use radiation material that is readily and inexpensively available from a commercial provider;

d) use minimal special equipment storage, or delivery devices, except for routine facilities available in most nuclear medicine or radiation oncology departments;

e) use a radiation carrier material that if applied as an unsealed free-gas form, the inert, noble gas properties essentially enable the molecules of the carrier material to rapidly dissipate throughout the body of the patient without any prolonged organ accumulation or chemical interaction, and rapid dilution of the carrier material is quickly re-released from the bloodstream through the lungs;

f) minimize long term occlusion of normal blood flow during therapy, thereby providing more flexibility as to administration time and dosage;

g) use a radiation carrier material that is stable and which can be pressurized, stored, and made to high millicurie activity per cubic centimeter with reasonable cost and availability;

h) use beta particles having excellent initial dose rate delivery and energy transfer when directly adjacent to the targeted tissue within the first one millimeter, and not penetrate much beyond this depth;

i) use gamma photon energies having depth doses that provide complementary dose deposition with the beta particles for the first one millimeter, and primary additive dose delivery for an additional two to three millimeters of the targeted tissue;

j) use these beneficial physical and biological radiation properties for treating restenosis, and malignancies (for example-in the brain, lung, esophagus, trachea, cervix, biliary ductal system, colon or rectum, the gastrointestinal system, the gynecological system, or head and neck) and other internal ailments where an internal application of radiation directly applied to the tissue may be needed; and k) attenuate the transmission dose to blood circulating through the apparatus, and while creating increased by-product radiation, delivering useful radiation dose over hundreds of micrometers of target tissue.

In order to accomplish these primary objectives, it would be desirable to have the device for delivering a therapeutic dosage of radioactive fluid to include a means to supply the treatment device with a given dosage of radioactive fluid from a source reservoir and then transfer the radioactive fluid back to the source reservoir at the completion of the treatment. Current systems for delivering radioactive gas, primarily designed for lung inhalation studies, lack the ability to retrieve the gas once it is introduced into the patient. Various syringe-type devices are known in the art for the purposes of delivering gas or inflating balloon catheters, however, they lack the safeguards necessary for working with radioactive gas, such as proper shielding and leakage prevention features that protect the patient and clinical personnel. In addition, it would be desirable to have a system whereby the standard commercially-available radioactive source vial with a pre-calibrated radioactive dosage could be directly loaded into the injection apparatus rather than relying on a standard syringe system which requires that a technician transfer or preload the radioactive material into the apparatus prior to the procedure, requiring additional handling and calibration.

SUMMARY OF THE INVENTION

The foregoing problems are solved and a technical advance is achieved in an illustrative medical, radiotherapy source vial for delivering a prescribed dose of radiation to a patient, for example, during and/or after an angioplasty procedure to inhibit, if not eliminate, restenosis and/or proliferation. The vial includes a radioactive fluid container having a contained volume for containing a prescribed dose of a radioactive fluid such as radioactive xenon gas. Advantageously, a radioactive fluid seal is disposed about the container and movable with respect to the container to change the contained volume of the container and, evacuate the radioactive fluid therein to radiation treatment apparatus. A radioactive fluid transport site such as a valve or septum is also positioned about the fluid container, which communicates with the contained volume and the exterior of the radioactive fluid container. An engagement mechanism such as a receiver is fixedly disposed about the container or seal and fixedly connectable to an external control mechansim. As a result, the contained volume in the fluid container can be decreased and increased by the actuation of the external control mechanism.

In one aspect, the radioactive fluid transport site can include a septum, a port, and/or operable valve. The engagement mechanism comprises a receiver such as a threaded arrangement for engaging with the external control mechanism. In one configuration, the fluid transport site is disposed on the radioactive fluid seal.

In another aspect of the invention, a resilient mechanism is disposed about the radioactive fluid container for urging the seal to a position in the container at which the contained volume is at an initial contained volume. In this aspect, the resilient mechanism can include by way of example a compression or tension spring.

In another aspect, the vial includes an attachment mechanism that is disposed on one or more of the container, fluid seal, or engagement mechanism. The attachment mechanism has an engaged condition and when therein maintains the contained volume fixed.

In still yet another aspect of the invention, the radioactive fluid seal is expandable and can, advantageously, include an inflatable member such as a balloon or bladder for urging the radioactive fluid from the container.

BRIEF DESCRIPTION OF THE DRAWING

FIG. 1 is an assembly drawing of an embodiment of medical radiation treatment system of the present invention;

FIG. 2 is a detailed isometric partially sectional view of the deflated catheter apparatus taken along line 2—2 of FIG. 1;

FIG. 3 is a detail sectional view of the fully-inflated catheter apparatus taken along line 3—3 of FIG. 2;

FIG. 17 is an isometric view of a fifth embodiment of the present invention disclosing a deflated catheter apparatus for use in treating malignancies in an organ such as the brain, esophagus, lung, or colon;

FIG. 18 is a detailed part sectional view of the inflated catheter apparatus of FIG. 17;

FIG. 19 is a detail sectional view of the pressure-sensitive flapper valve for the inflated catheter apparatus taken along line 19—19 of FIG. 18;

FIG. 28 is an enlarged, pictorial, proximal end view of the catheter apparatus of FIG. 1 with an alternative embodiment of an indicator thereon;

FIG. 29 is an enlarged, longitudinally sectioned view of the elongated member of the catheter apparatus of FIG. 1 taken along a line through the dosimetry indicator thereof;

FIG. 30 is an enlarged sectional view of an alternative embodiment of the radiation sensitive film of FIG. 28;

FIG. 31 is an enlarged sectional view of another alternative embodiment of the radiation sensitive film of FIG. 28;

FIGS. 36–41 are cross sectional views of alternative embodiments of the present invention;

FIG. 44 is a partially sectioned side view of a second embodiment of the delivery apparatus;

FIG. 45 is a cross-sectional view of the locking handle of the apparatus of FIG. 44;

FIG. 46 is an alternate embodiment of the piercing cannula of the apparatus of FIG. 44;

FIG. 48 discloses a sectioned side view of a fourth embodiment of the delivery apparatus that includes a second syringe to pressurize and displace radioactive fluid from the source vial;

FIG. 52 is a pictorial view of a gas-tight container having a specific interior volume and concentration of radioactive fluid for administering a radiation treatment to a patient;

FIG. 53 is a pictorial view of the gas-tight container of the medical radiation treatment device of FIG. 1;

FIGS. 54–56 are a partially sectioned side views of an embodiment of a radiotherapy source vial;

FIG. 65 is a partially sectioned side view of a locking mechanism embodiment of a radiotherapy source vial;

FIG. 66 is and end view of the embodiment of FIG. 65;

FIG. 67 is a partially sectioned side view of a second locking mechanism embodiment of a radiotherapy source vial;

FIG. 68 is an end view of the embodiment of FIG. 67;

FIGS. 73–75 are partially sectioned side views of an alternate embodiment of a radiotherapy source vial;

FIG. 76 is a side view of an alternate coupler embodiment of a radiotherapy source vial;

FIG. 77 is an end view of the embodiment of FIG. 76;

FIG. 78 is an enlarged sectional view of an alternate embodiment of a radiotherapy source vial.

DETAILED DESCRIPTION

Figure 4:
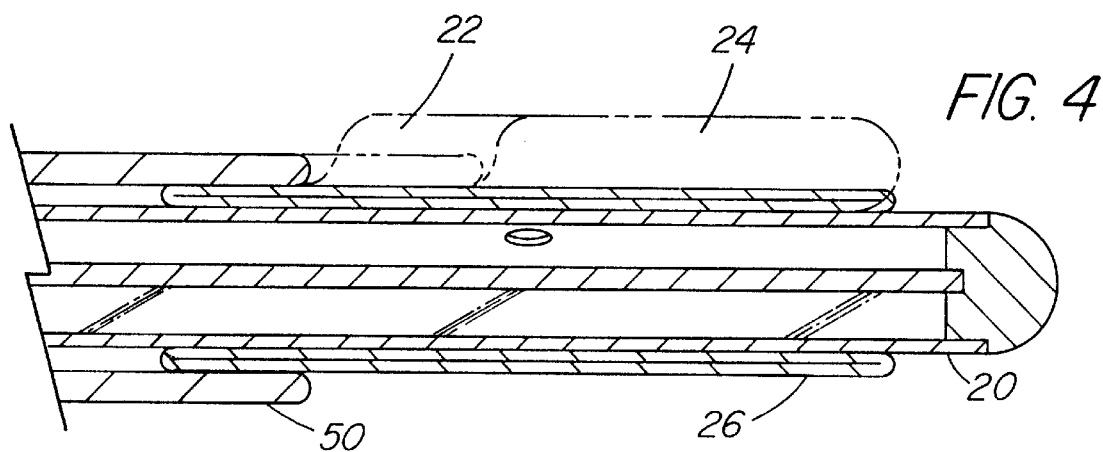
FIG. 4 is a detailed longitudinal sectional view of the deflated catheter apparatus taken along line 4—4 of FIG. 1.
Figure 5:
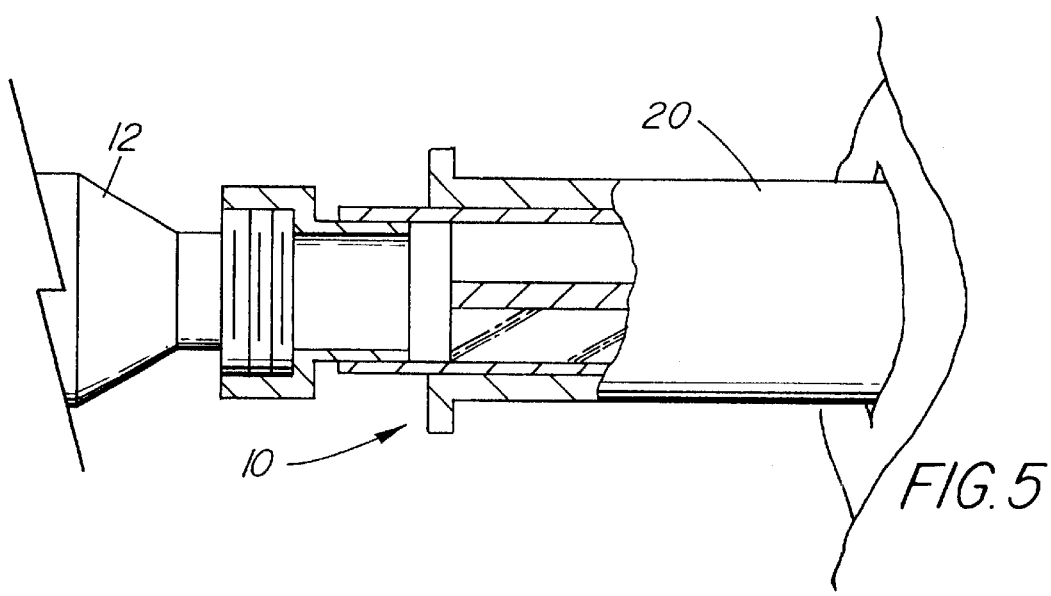
FIG. 5 is an enlarged partially sectional view of the engagement between the protected, syringed gas supply and the catheter apparatus of FIG. 1.
Figure 6:
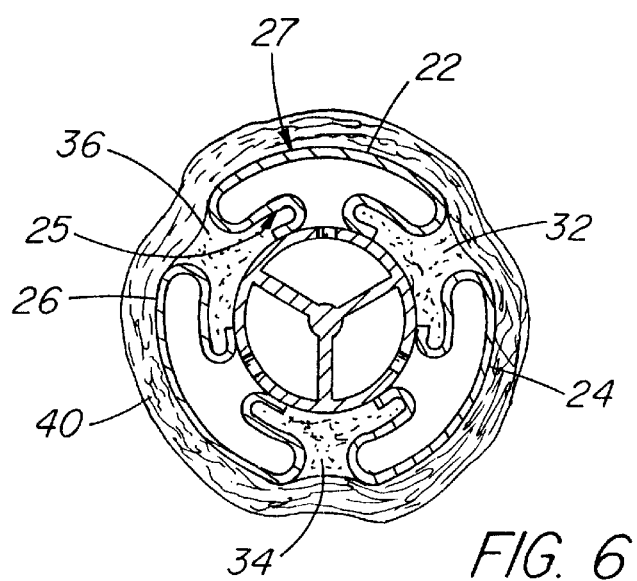
FIG. 6 is a detailed cross-sectional view of the fully-inflated catheter apparatus as shown in FIG. 1 inside an arterial wall.

FIGS. 1 to 6 disclose the preferred embodiment of a medical radiation treatment system 10 of the present invention which includes a medical radiation treatment device 14 that is connectable to a radioactive fluid delivery device such as balloon catheter apparatus 20. With reference to FIGS. 52 and 53, medical radiation treatment device 14 includes a sealed source of radioactive fluid, preferably gas 12, which is contained in a sealed, preferably fluid or gas-tight, container 15. The gas-tight container 15 in one aspect of the invention is a commercially available, 3 cc, sealed vial with a gas-tight seal membrane 16 at one end thereof for accessing the radioactive gas. The gas-tight seal or membrane is punctured with a piercing cannula or needle so as to permit the radioactive gas in the vial to flow therefrom to the delivery device such as balloon catheter apparatus 20. The fluid or gas-tight container 15 can have an interior volume 17 ranging in size from 0 to 10 cubic centimeters. Preferably interior volume 17 can range from 1 to 7 cubic centimeters. More preferably, interior volume 17 can range from 2 to 6 cubic centimeters and, most preferably, from 2 to 3 cubic centimeters. The particular range of the interior volume is dependent on the size of the particular vessel to be treated which can range from 3 to 8 mm in diameter. This range is intended to serve the coronary, carotid, and other peripheral vessels, and the hepatic visceral vasculature. A-V grafts in the range of 5 to 8 mm are also intended to be included in this grouping. For purposes of treating coronary vessels, a 3 cc vial is selected for containing approximately 2 cc of a radioactive gas including for example, xenon-133. To deliver a prescribed total radiation dose, the radioactive fluid includes a carrier such as carbon dioxide gas or any non-radioactive inert or noble gas and a radioactive substance such as xenon-133 or xenon-127 or other inert radiogases dispersed in the carrier carbon dioxide gas. The carrier is at least 90% by volume of the radioactive fluid with the radioactive substance being at most 10% by volume of the radioactive fluid. Preferably, the carrier gas is approximately 95% by volume of the radioactive fluid, and the radioactive substance is approximately less than or equal to 5% by total injectable volume of the radioactive fluid. These concentrations and volumes of gas allow a catheter balloon to be inflated to a volume of approximately 0.6 to 1.0 cc generally resulting in relatively low atmospheres of pressure. The radioactive fluid or gas contained in the vial has a specific concentration in the range of 50 to 500 millicuries per cubic centimeter for providing a prescribed dose of radiation to a lesion site for the prevention of restenosis, hyperplasia or smooth muscle cell proliferation. As determined preliminarily from porcine studies, a total radiation dose ranging from 500 to 3000 Centi Gray (cGy) appears to be an appropriate prescribed dosage. These studies also indicate that a preferred range would include 800 to 1500 cGy. A more preferred total radiation dose would range from 800 to 1000 cGy. To provide such total radiation dose, the specific concentration of the radioactive fluid in the container should range from 50 to 500 millicuries per cubic centimeter, preferably 100 to 150 millicuries per cubic centimeter depending on the anatomical site to be treated such as with the coronaries, the peripheral vasculature, the carotids and other areas such as associated with A-V grafts.

FIG. 52 depicts an enlarged pictorial view of medical radiation treatment device 14 including sealed container 15 with radioactive fluid 12 contained in interior volume 17 thereof. As previously suggested, seal or membrane 16 is disposed at one end of the sealed container, which can be punctured by a piercing cannula or needle. This septum is preferably made of a synthetic rubber, such as Viton® or the like, which minimizes risk of prolonged leakage and/or gas/fluid adherence.

FIG. 53 depicts an enlarged pictorial view of medical radiation treatment device 14 of FIG. 1 including a sealed, gas-tight container 15 with a gas-tight plunger 18 or gas-tight plunger base positioned opposite the distal end thereof for pushing radioactive fluid 12 from interior volume 17 of the container when as valve 13 is operated to the open position. The gas-tight valve can be a separate component that is attachable to the container or can be integrated into the container. This embodiment of sealed container 15 provides for a much more complete evacuation of the radioactive fluid in interior volume 17. In addition, the container walls can have varying degrees of glass/plastic radiation shielding for alternating higher radiation activity levels.

Intravascular treatment with localized ionizing radiation delivered via conventional solid radio-sourced catheter-based systems has demonstrated a reduction in post-angioplasty neointimal formation in animal models and randomized human clinical trials. Prior art systems can falter with regards to dose homogeneity, optimal efficacy, radiation safety restrictions, patient handling, and radionuclide availability. The present medical radiation treatment system was developed and tested for irradiation with historically safe xenon-133 inert radiogas. In order to determine the efficacy of xenon-133 radiogas to inhibit neointimal formation and subsequent luminal restenosis, angioplasty balloon injury was performed in the coronary arteries of 17 juvenile porcine subjects. Following balloon injury of the coronary arteries of these porcine subjects, 3.0 to 3.5 mm balloons of 30 to 40 mm lengths were positioned to cover and overlap the injured vessel segment. A negative pressure was obtained in the radiocatheter prior to placement. Xenon-133 activity of 250–300 mCi (in 2.0–2.5 cc's) was injected to fill the balloon segment, uniformly abutting the lumen wall. A dose of either 15 Gy or 30 Gy was prescribed and delivered to a target tissue depth of 0.25 mm from the expanded balloon surface. The dwell time during inflation was 2±0.5 minutes (avg.). Prior in vitro dosimetry trials were performed to obtain reference micro-dosimetry results. Summary data analysis including reference tables and graphics, were performed and applied for delivery ranges as described above. This was performed using multiple trials with Cook GRII® balloon catheters of various coronary sizes with different quantities of xenon-133 (millicuries), exposure time (min.), and volumes (cc). Customized solid water phantoms, layered Gafchromic film, laser/light densitometry readings, and referenced dosimetry graphics were standardly applied to obtain these referenced measurements.

Localization of the radiogas filled balloon was verified by Gamma Camera and fluoroscopic imaging. The radiation exposure measured 100 mR/h at the chest wall and 5 mR/h immediately bedside. Two weeks following treatment, the animals were harvested, the arteries perfusion fixed, stained, and morphometrically analyzed. The intimal area (IA) was compared between the irradiated and control arteries. The following results were obtained:

|  | IA (mm$^2$) | P-Value (one way ANOVA test) |
| --- | --- | --- |
| Control (n = 22) | 1.04 ± 0.20 | — |
| Xe-133 15 Gy (n = 9) | 0.34 ± 0.17 | 0.018 |
| Xe-133 30 Gy (n = 8) | 0.38 ± 0.18 | 0.033 |

66% and 44% of the 15 Gy and 30 Gy groups respectively showed IA (mm$^2$) of ≦0.06. A slight trend toward increased thrombosis was noted in the 30 Gy group.

Intimal area (IA) corrected for medical fracture length (IA/FL) was also compared for the harvested vessels:

|  | IA/FL | % absolute ratio reduction |
| --- | --- | --- |
| Control (n = 22) | 0.55 ± 0.06 | — |
| 15 Gy (n = 9) | 0.16 ± 0.08 | 71% |
| 30 Gy (n = 8) | 0.32 ± 0.12 | 45% |

As a result, it was concluded from the harvested vessels that a xenon-133 radiogas balloon catheter is feasible and effective in markedly reducing neointimal formation in the porcine model and can offer a safe and pragmatic modality for clinical use.

The balloon catheter apparatus 20 is preferably of latex or a similar synthetic compound, commonly used for intravascular applications, and void of any silicon-based or other metal-based materials. The balloon catheter apparatus is disposable after each patient use, and is designed to handle peak expected pressures less than those used in conventional angioplasty. These pressures typically range from one to ten atmospheres.

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as preferably xenon, or an isotope of xenon. However, the present invention is not limited to xenon gas or an isotope thereof, and the preferred fluid includes all gases and isotopes thereof, radioactive gases or radiogases (inert and/or non-inert) or gases capable of fluorescence, phosphorescence, or luminescence (electron stimulation). Examples of gases include, but are not limited to, xenon, krypton, neon, radon and their isotopes. A radiogas can be dissolved in a liquid or solution (sterile) such as sterile water or saline and be used as a liquid radiofluid. Liquids include all isotopes of liquids and solutions. An isotope can be radioactive or non-radioactive. Radioactive includes nuclear (nucleus) decay of an atom. A radionuclide is any radioactive atom. Fluorescence, phosphorescence or luminescence is associated with electron instability and subsequent emission of radiant energy. Liquids also include all gases dissolved in liquids or solutions. Examples of liquids include, but are not limited to, liquid phosphorus, rhenium, yttrium, technetium, iodine, gallium, chromium, strontium, thallium, samarium, ytterbium, palladium, and all isotopes thereof, and all compounding and binding solutions thereof. All gels utilizing the aforementioned gases or liquids (solutions) are also contemplated. Additional radionuclides can include osmium, vanadium, ruthenium, bismuth, or other transitional heavy metals and their isotopes for liquid and/or gel-type compounding. All inert dual photon/electron emitting radionuclides are further contemplated as well as all inert single particle radio-emitting nuclides and all non-inert radionuclides thereof. Still further contemplated are all inert or non-inert radiofluids which use electron stimulation to produce by-product fluorescent, phosphorescent or luminescent radiant energy for patient treatment. The use of by-product radiant energy emissions including fluorescent, phosphorescent or luminescent emissions can be utilized for therapeutic treatment. Implementation of radionuclide and by-product radiant energy emissions can be applied by the use of the catheter apparatus in the following combinations;

(a) gases and/or fluids or single fluids alone either as a gas-gas or gas-liquid, and/or either inert or non-inert, and/or radioactive or non-radioactive such that the photon or electron emissions of one radiofluid can induce electron shift, scatter, or a quantum level change in the electron shell of the same or other combined "fluid" atoms thereby causing production of relatively low energy photon/electron (possibly in a cascaded amplification) emissions into the targeted tissue as a controlled/calculated dose;

(b) radiofluid(s) as described in (a), except that induction of listed radiant energy is provided via electrical source stimulation from an electrode, cathode, wire or other transmission source such that controlled electrical currents and/or electrical potential delivered through the catheter to the radiofluid or non-radiofluid of the balloon catheter which causes expected electron excitation and/or quantum level fluctuations with by-product fluorescence, phosphorescence and/or luminescence for the aforementioned therapeutic treatments; and (c) phosphorus and/or other known fluorescent metals or alloys are implanted in the balloon material and/or catheter structure so that the combinations described in (a) and (b) (i.e., radioemission, by-product decay energy and/or direct electrical stimulation) can cause effect on the implanted/layered materials so as to create fluorescent, phosphorescent or luminescent energy delivery as these materials stabilize their electron structure after such stimulation.

The unique medical radiation treatment delivery system 10 of the present invention uses a radioactive fluid. The catheter apparatus 20 includes at least a single balloon and, preferably, a plurality of balloon sections 22, 24, and 26, which are inflated with the radioactive fluid. Residual blood flows through the vessel when the balloon or balloon sections 22, 24, and 26 are inflated through a plurality of interposed sections 32, 34, and 36 disposed between the balloon sections.

Figure 25:
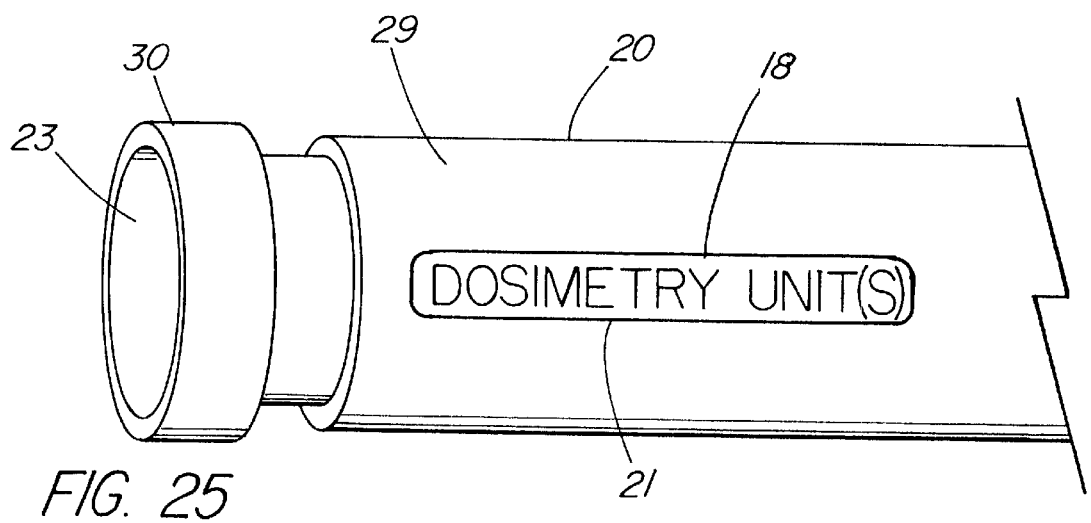
FIG. 25 is an enlarged, pictorial, proximal end view of the catheter apparatus of FIG. 1 with a radiation dosimetry unit(s) indicated thereon.

FIG. 25 depicts an enlarged, pictorial, proximal end view of a medical fluid delivery device such as catheter apparatus 20 of FIG. 1. Affixed, positioned, disposed, or connected to, on, or about the outer surface of catheter apparatus 20 near the distal end thereof is indicator 21, which is indicative of a radiation dosimetry unit of measurement. By way of example, radiation dosimetry unit of measurement is at least indicative of the radiation that can be radiated through at least one portion of the catheter apparatus. The at least one portion of the catheter apparatus includes a single balloon or, preferably, balloon sections 22, 24, and 26, which are inflated with a radioactive fluid. The radiation dosimetry unit of measurement for the balloon or balloon sections of the catheter apparatus can include, but is not limited to, radiation dose rate, total radiation dose at a predetermined tissue depth, radiation source activity, radiation time exposure, tissue depth of a radiation dose, radiation source, or an incidental radiation dose rate. The total radiation dose at a reference tissue depth for a radioactive fluid delivery device such as catheter apparatus device 20 is approximately equal to the radiation source activity (i.e., specific activity in millicuries per volume or density unit) multiplied by the radiation dose rate of the device multiplied by the exposure time of the radioactive fluid source. By way of example, a typical prescribed total radiation dose for a radiation delivery device such as catheter apparatus 20 can be 1400 cGy. This total radiation dose rate is referenced to a tissue depth at a delivery interface of typically 0.25 mm or 0.50 mm for a radioactive fluid such as xenon-133 gas. A typical radiation dose rate for a balloon catheter of the present invention can typically be in the range of 2 to 10 cGy per minute per millicurie (mCi).

The radiation dose rate of a balloon material is a function of or is dependent upon the thickness of the balloon material, the density of the balloon material, and/or the volume of the balloon. In addition, the volume is, in turn, dependent upon the length of the radiation source and, in particular, the longitudinal length of the balloon along with the diameter and radius of the balloon. The axial length of the balloon is important with respect to the radiation source in that accumulative dosimetry effects (scatter, coincidence, photo electric) are achieved with the radioactive fluid disposed along the length of the catheter. The radiation dose rate is also effected by the surface area of the inflatable balloon in response to the radioactive fluid.

Radiation source activity is a function of the radioactive fluid or preferably of the radioactive gas that is used with the radiation treatment. As described hereinafter, radioactive xenon-133 gas is preferred in that it is an inert gas that provides synchronous gamma and beta radiation emission with a half life of approximately five days. Concentrations of xenon-133 gas can typically range from 10 mCi to 150 mCi per cc or more of gas volume at the time of calibration.

Radiation exposure time is prescribed by the attending physician, commonly with a speciality in radiation oncology, nuclear medicine or nuclear oncology. Exposure times range from less than a minute upwards to ten minutes, depending on the activity of the radiation source. Particular concentrations of the radiation source are normally provided with commercially available radiation sources. These concentrations are used by the physician to determine radiation exposure time. The radiation dose rate is a function of the properties of delivery devices such as catheter apparatus 20, which in turn is a function of balloon material thickness, density and volume as previously indicated. An external or internal brachytherapy medical radiation delivery device can be experimentally dose calibrated and verified by a radiation physician specialist, medical physicist, or certified radio/ nuclear laboratory, or with approved device-specific computer software for patient treatment. With such a calibrated radiation dose rate, the physician can calculate and prescribe the required radiation source concentrations and exposure times for treatment of the patient. The calibration of the delivery device typically includes positioning the delivery device in a phantom and positioning radiation detectors/ sensors at a prescribed distance away from the delivery device in the phantom. A series of measurements are used to graph the radiation from a series of radioactive fluid concentrations applied thereto. Such calibration is necessary and demanded by various regulatory agencies so that the radiation treatment provided to a patient is within specified limits of the prescribed total radiation dose. In addition, multiple radiation safety profiles are evaluated for handling and delivery.

Figure 26:
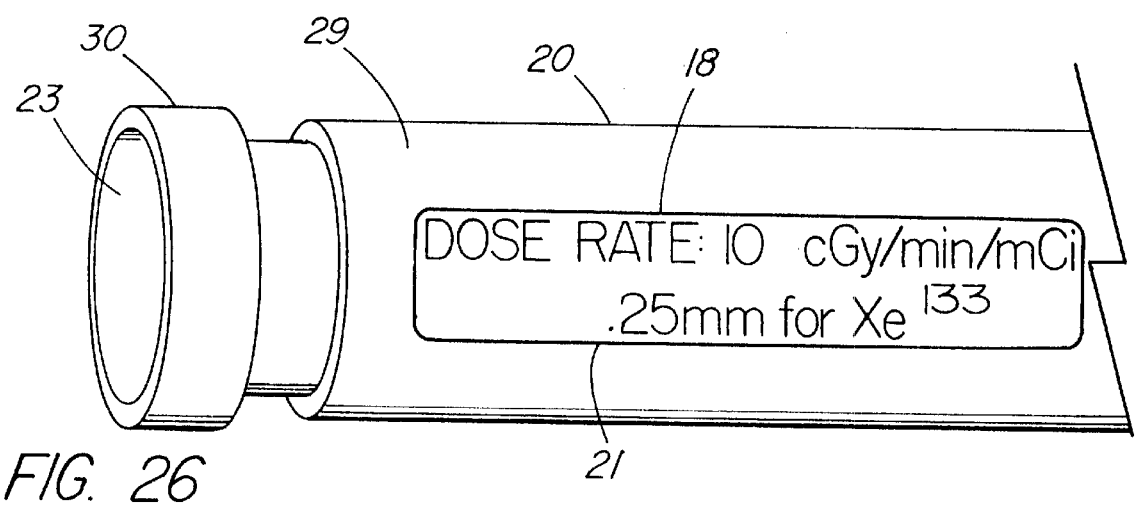
FIG. 26 is an enlarged, pictorial, proximal end view of the catheter apparatus of FIG. 1 with a radiation dose rate indicated thereon.

FIG. 26 depicts an enlarged, pictorial, proximal end view of catheter apparatus 20 of FIG. 1. In this particular embodiment, the radiation dosimetry unit of measurement is the radiation dose rate, which is indicated as 10 cGy/min/ mCi at a tissue depth of 0.25 mm for a radiation source of xenon-133. With this radiation dosimetry unit of measurement indicated on the catheter, an attending physician can readily calculate and prescribe a desired total radiation dose for a patient with commercially available radiation concentrations of, for example, xenon-133 and a calculated radiation exposure time as a verified standard for a particular catheter/balloon make, style, and size. As a result, the attending physician eliminates the need to perform more laborious calculations and independent measurements, or having the delivery device sent to a medical physicist or laboratory for calibration of the radiation dose rate of the delivery device.

In addition, the catheter is made in a uniform-single construct with a gas-tight injection port component, which is leak-proof and injection "friendly" and has a septum of "resistant" synthetic rubber (Viton), which minimizes risk of leak or xenon adsorption. Furthermore, a leak-tight directional valve controls and locks direction of radiofluid passage for safety. A standard-type catheter would not provide this.

Although the indicator is affixed, positioned, disposed, connected to, on, or about the proximal end of the catheter for visualization by the attending physician, this indicator 21 is normally indicative of the portion of the delivery device such as the inflated balloon of a balloon catheter, which is inflated for the purposes of making contact with tissue to be treated. More particularly, the indicator and the radiation dose rate is indicative of the material that comes in contact with the tissue to be treated. By way of example, the outer surface or wall of the balloon catheter along with the density and thickness thereof are one of the major factors in determining the radiation dose rate. This radiation dosimetry unit of measurement is experimentally calculated or computer modeled and verified with experimental calculations and applied to the proximal end of the delivery device. The indicator of the dosimetry unit can be printed or painted on the outer surface of the catheter, embossed in or raised from the outer surface of the delivery device. The indicator can comprise at least one of a plurality of symbols, letters or numbers disposed on the radioactive delivery device for indicating the dosimetry unit of measurement. It is also contemplated that any indicator of whatever type can be affixed, disposed or positioned on the delivery device for the purposes of indicating at least one radiation dosimetry unit of measurement. Not only can the radiation dosimetry unit of measurement be directed to the portion of the delivery device that comes in contact with the tissue to be treated, but also radiation indicators such as incidental radiation dose rate, which is important to attending personnel to minimize their exposure to radiation.

Figure 27:
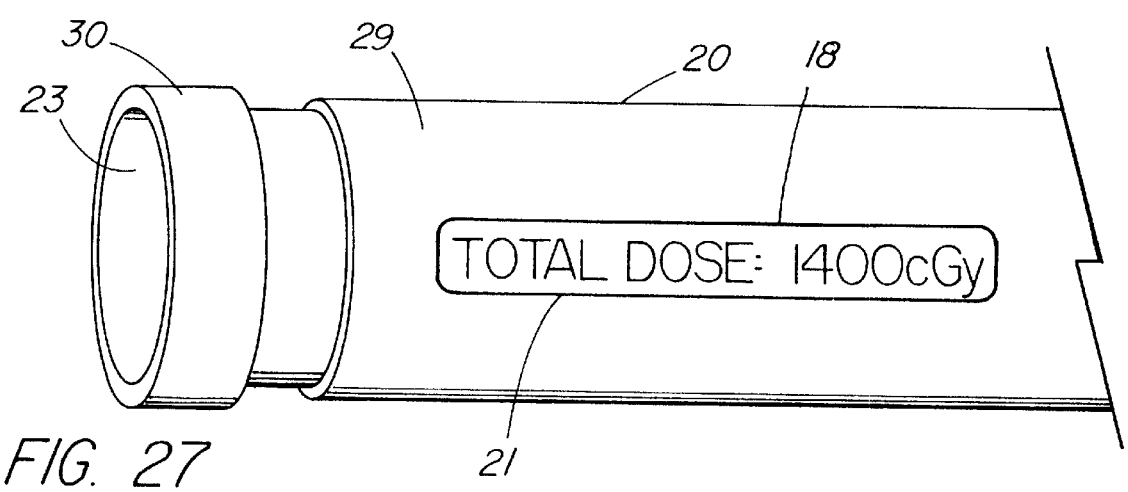
FIG. 27 is an enlarged, pictorial, proximal end view of the catheter apparatus of FIG. 1 with a total radiation dose indicated thereon.

FIG. 27 depicts an enlarged, pictorial, proximal end view of catheter apparatus 20 of FIG. 1 in which the radiation dosimetry unit of measurement is indicated as total dose and, in particular, a total radiation dose of, for example, 1400 cGy. This indicator 21 is thus printed, embossed, or raised and indicated as total dose. Inflation lumen 23 extends longitudinally through elongated member 29 of catheter apparatus 20. A gas tight fitting/hub 30 is affixed in a well-known manner to elongated member 30 of catheter apparatus 20. These particular components of catheter apparatus 20 are also depicted in FIGS. 25 and 26. Elongated member 29 comprises a polyurethane, polyethylene, polyimide, polyvinyl chloride, polyamide, polytetrafluoroethylene, silicone, or any other suitable material. The selection of the catheter material is typically dependent on the particular anatomical site that the catheter apparatus is to be positioned or extended through. These elongated member materials can also be coated with a hydrophillic slip coating to further ease insertion and introduction to the treatment site. In addition to well-known hydrophillic slip coatings, the inner and/or outer surfaces of the elongated member can be treated such as with ion beam bombardment or deposition, which is commercially available from the Spire Corporation, Bedford, Mass. Ion beam bombardment or deposition can significantly alter the surface energy density of the elongated member material to reduce adhesion of thrombus or other agents thereon. This treatment is also known to provide an antibacterial, antifungal, or an antithrombogenic surface.

To minimize radiation exposure to attending personnel elongated member 29 of catheter apparatus 20 can include a high density material to absorb and/or block the radiation from the radioactive fluid when in inflation lumen 23. By way of example, this high density material can constitute a loading of greater than 30 percent by weight of, for example, barium, tungsten, lead, tantalum, titanium, bismuth, gold, platinum, palladium or rhodium.

Referring the reader's attention to FIGS. 1–4 and 6–8, the portion of the delivery device such as balloon 22 through which radiation from a radioactive fluid is normally directed includes at least one of silicone, latex, a synthetic material similar to latex, polyamide, vinyl, polyethylene, polytetrafluoroethylene, polyethylene terephthalate, fluorinated ethylene propylene, or any other suitable material. The balloon material can also include a loading of high density material to absorb or block radiation and thereby consequentially redirect the radiation to the treatment site. This material can also block or lessen radiation exposure of blood passing through the balloon sections. This high density material can be a loading of greater than 20 percent by weight of at least one of barium, tungsten, lead, tantalum, titanium, bismuth, gold, platinum, palladium or rhodium. The radiation dose rate of the balloon can also be altered or redirected by applying a thin coating of a metal or other reflecting materials to the various inner and outer surfaces of the balloon as herein later described.

FIG. 28 depicts an enlarged, pictorial, proximal end view of catheter apparatus 20 of FIG. 1 with an alternative embodiment of indicator 21 affixed, disposed or positioned thereon. Indicator 21 includes a housing or holder 19 as depicted in which a radiation sensitive film 31 is positioned therein. The arrow indicates the placement of radiation sensitive film 31 into indicator holder 19. Positioned adjacent to aperture 33 on the indicator is a visible shades scale 35 having various shades of gray between white and black at the opposite ends thereof. When exposed to various dosages of radiation, radiation sensitive film 31, such as a Gafchromic type film from, for example, Nuclear Associates of Carle Place, N.Y., changes color. The Nuclear Associates' Gafchromic film exhibits various hues of blue in response to radiation. This change in color is visible as a change from clear to black with various shades of gray therebetween. The various shades of gray or blue indicate the amount of radiation film 31 has been exposed to. Thus, the attending physician can readily match the visible shade of radiation sensitive film 31 with gray scale 35 to determine the radiation dose and activity of the radiation source. For purposes of convenience, total dose amounts can be printed or indicated right next to each shade of gray on gray scale 35.

FIG. 29 depicts an enlarged longitudinal sectioning of elongated member 29 of catheter apparatus 20 through indicator 21. Radiation sensitive film 31 is inserted into channel 37 of the indicator for visual reading of the change in color of the film. The bottom material 39 of indicator 21 is preferably selected to be that of the material coming in contact with the tissue to be treated. Even more preferably, the bottom material is selected to be of equal thickness along with the same loading of the high density material of the balloon material. This is to best approximate the radiation dose being applied through the balloon to the treatment site. Depending on the radiation volume size, the thickness and loading of the bottom material can be modified to more closely approximate the total radiation dosage being radiated at the treatment site.

FIG. 30 depicts an enlarged sectional view of an alternative embodiment of radiation sensitive film 31. In this embodiment, the radiation sensitive film is layered in a stair step configuration to provide a greater change in color or the gray scale depending on the type of radiation source being utilized.

FIG. 31 depicts still another alternative embodiment of radiation sensitive film 31 in which strips of radiation sensitive Gafchromic type film are butted end-to-end. Each strip or segment has a different sensitivity to radiation and thus can be utilized to indicate a much larger range of radiation doses being exposed thereto.

Figure 33:
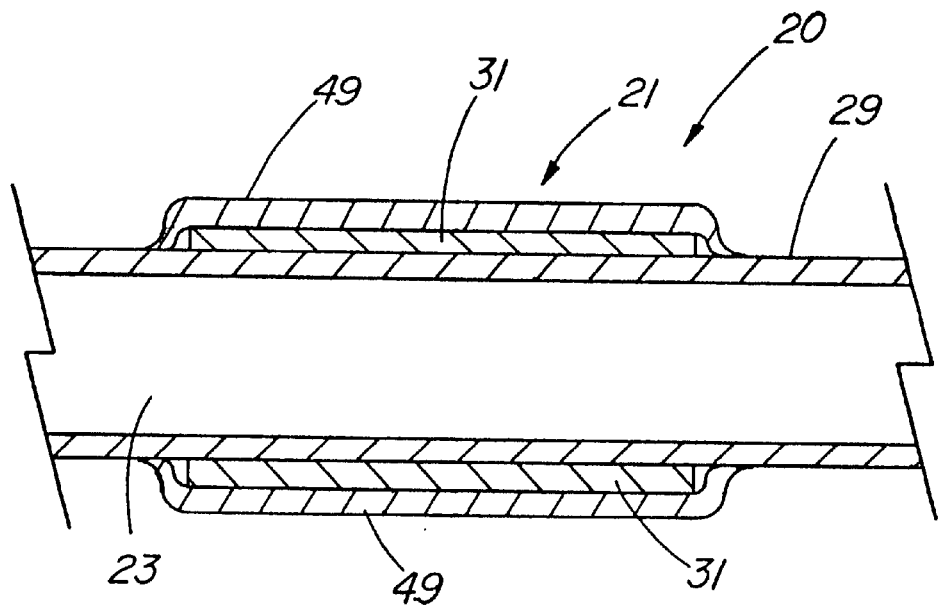
FIG. 33 is an enlarged, longitudinally sectioned, proximal end view of the catheter apparatus of FIG. 1 with still another alternative embodiment of an indicator thereon.

FIG. 33 depicts an enlarged, sectioned, proximal end view of catheter apparatus 20 of FIG. 1 with still another alternative embodiment of radiation indicator 21 thereon. In this particular embodiment, radiation indicator 21 includes radiation sensitive film 31 positioned around elongated member 29 of the catheter. The thickness of elongated member 29 underneath radiation sensitive film 31 is formed to approximate the relative thickness of the balloon catheter as well as the treatment depth of the tissue intended to be in contact with the balloon. As a result, the wall thickness of member 29 beneath radiation sensitive film 31 best approximates the balloon material and tissue so that the radiation sensed by film 31 is that at the desired tissue treatment depth. The xenon radioactive gas resides in inflation lumen 23 of the elongated member as well as the inflatable balloon. Positioned over and around radiation sensitive film 31 is transparent material 49 such as clear silicone so as to hold the radiation sensitive film in position around the proximal end of the catheter apparatus. The clear transparent property of this material or other similar materials provides for minimal distortion of the hue or color of the radiation sensitive film.

Figure 34:
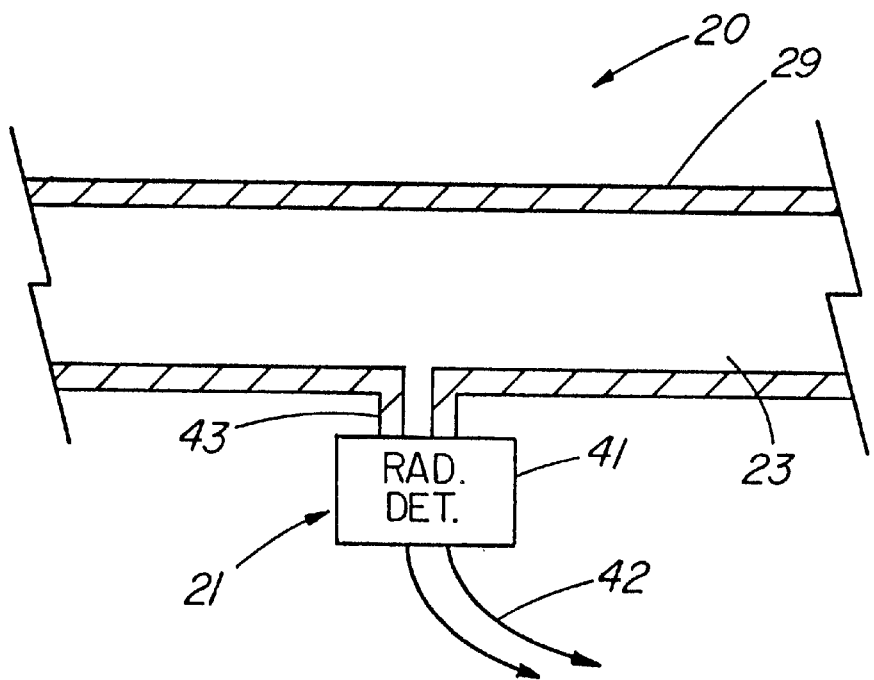
FIG. 34 is an enlarged, longitudinally sectioned, proximal end view of the catheter apparatus of FIG. 1 with yet still another alternative embodiment of an indicator thereon.

FIG. 34 depicts an enlarged, sectioned, proximal end view of the catheter apparatus 20 of FIG. 1 with yet still another embodiment of indicator 21 disposed thereon. In this particular embodiment, the radioactive fluid not only passes through inflation lumen 23 of elongated member 29 but also out of side port 43 to electronic radiation detector 41. This electronic radiation detector is commercially available and is an electronic ion exchange detector. Electrical conductor leads 42 extending from the radiation detector are connected to an electronic display unit such as an LCD or LED display for displaying radiation level(s).

Figure 32:
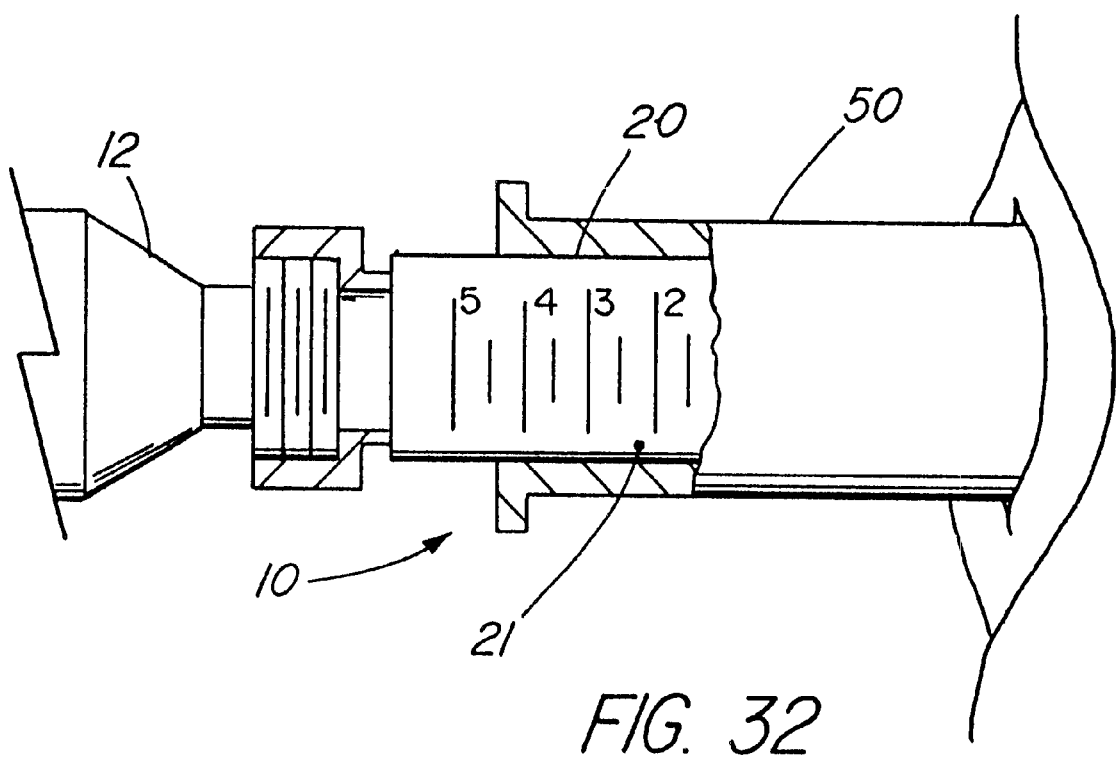
FIG. 32 is an enlarged, partially sectioned view of the catheter apparatus of FIG. 1 with a dosimetry unit indicator thereon.

Returning the reader's attention to FIGS. 1–6, the method of the present invention is designed to apply ionizing radiation prophylactically to post-angioplasty vascular tissue or tumors disposed internally within a patient while minimizing exposure of healthy tissue. Initially, the location and the size of the lesion 40 to be treated are clinically identified, perhaps, with a fluoroscope. The catheter apparatus 20 is then introduced and positioned adjacent to the lesion 40. The plurality of discrete balloon sections 22, 24, and 26 of a special, hypo-dense, thin material enable the inflated catheter apparatus 20 to more closely match the internal tissue wall, and minimize the amount of internal gas loss in the event of leakage. The catheter apparatus 20 includes an outer retractable radiation sleeve or shield 50 to prevent the exposure of healthy tissue adjacent to the lesion to radiation. After the catheter apparatus 20 is positioned alongside the lesion 40, the radiation shield 50 is retracted to a specific measurable length as depicted in FIG. 32. This specific length controls dosage rate and radiation source volume size. The balloon sections 22, 24, and 26 are then inflated with the radioactive fluid exposing the lesion 40 to the radiation dosage. The preferred gas, xenon or xenon isotope, emits beta and gamma particles into the lesion 40. Furthermore, indicator 21 can be used to establish dosage rate and total radiation dose.

Figure 7:
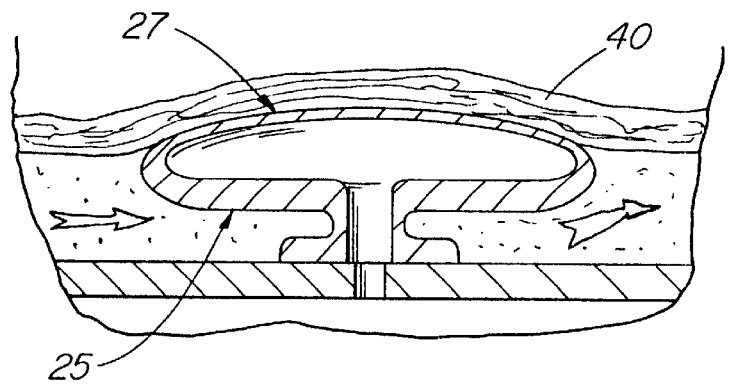
FIG. 7 is a second embodiment disclosing a detailed longitudinal sectional view of a balloon of a catheter apparatus being fully-inflated and having a thickened interior wall and a thinner, hypo-dense outer wall.
Figure 8:
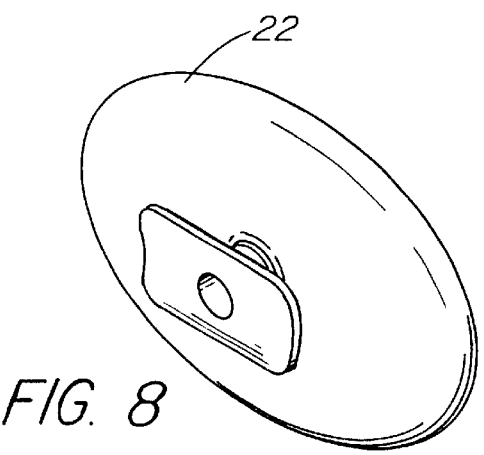
FIG. 8 discloses a detail of an inflated balloon of the catheter apparatus shown in FIG. 7.

The catheter apparatus 20 enables substantial blood or other fluid flow between the balloon sections 22, 24, and 26 when fully inflated. The balloons sections 22, 24, and 26 include a unique inner and outer surface 25 and 27 configuration. The radiation flow is directed through the outer surface 27 of the catheter apparatus 20 to the lesion 40 while exposure to radiation of the blood flowing internal to the catheter apparatus 20 is minimized. Accordingly, the inner surface 25 is more attenuating to the transmission of radiation than the outer surface 27. Either the inner surface (wall) 25 is thicker than the outer surface (wall) 27 as shown in FIG. 7, or the inner surface 25 includes a layer of material that is resistant to the penetration of radiation (not shown).

Figure 9:
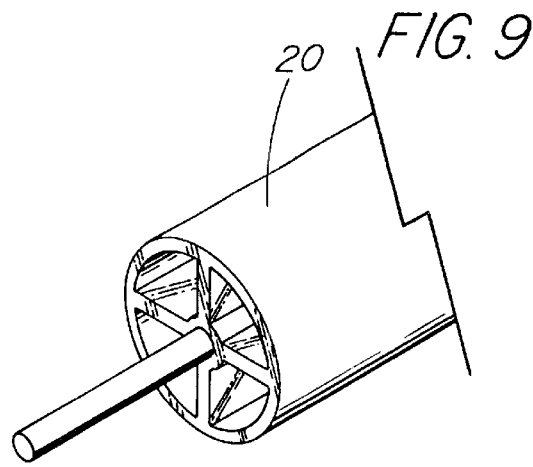
FIG. 9 discloses a third embodiment of the catheter apparatus having a removable central lumen guide/localizing wire that is radio-opaque.
Figure 10:
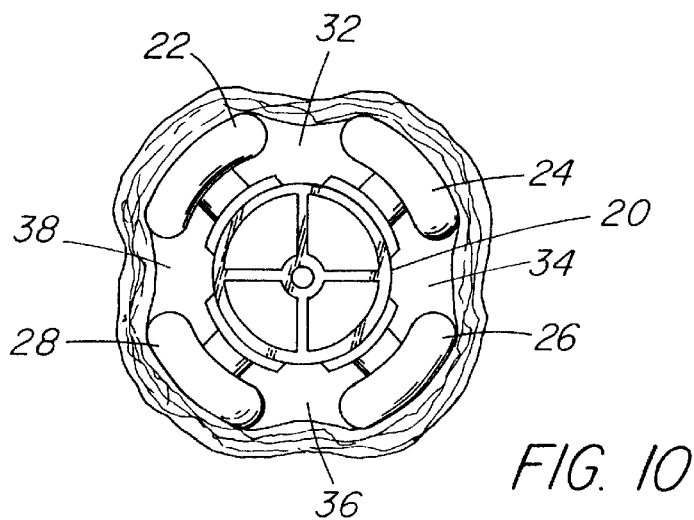
FIG. 10 is a detailed cross-sectional view of the fully-inflated catheter apparatus of FIG. 9 within the arterial wall.
Figures 11, 12, 13:
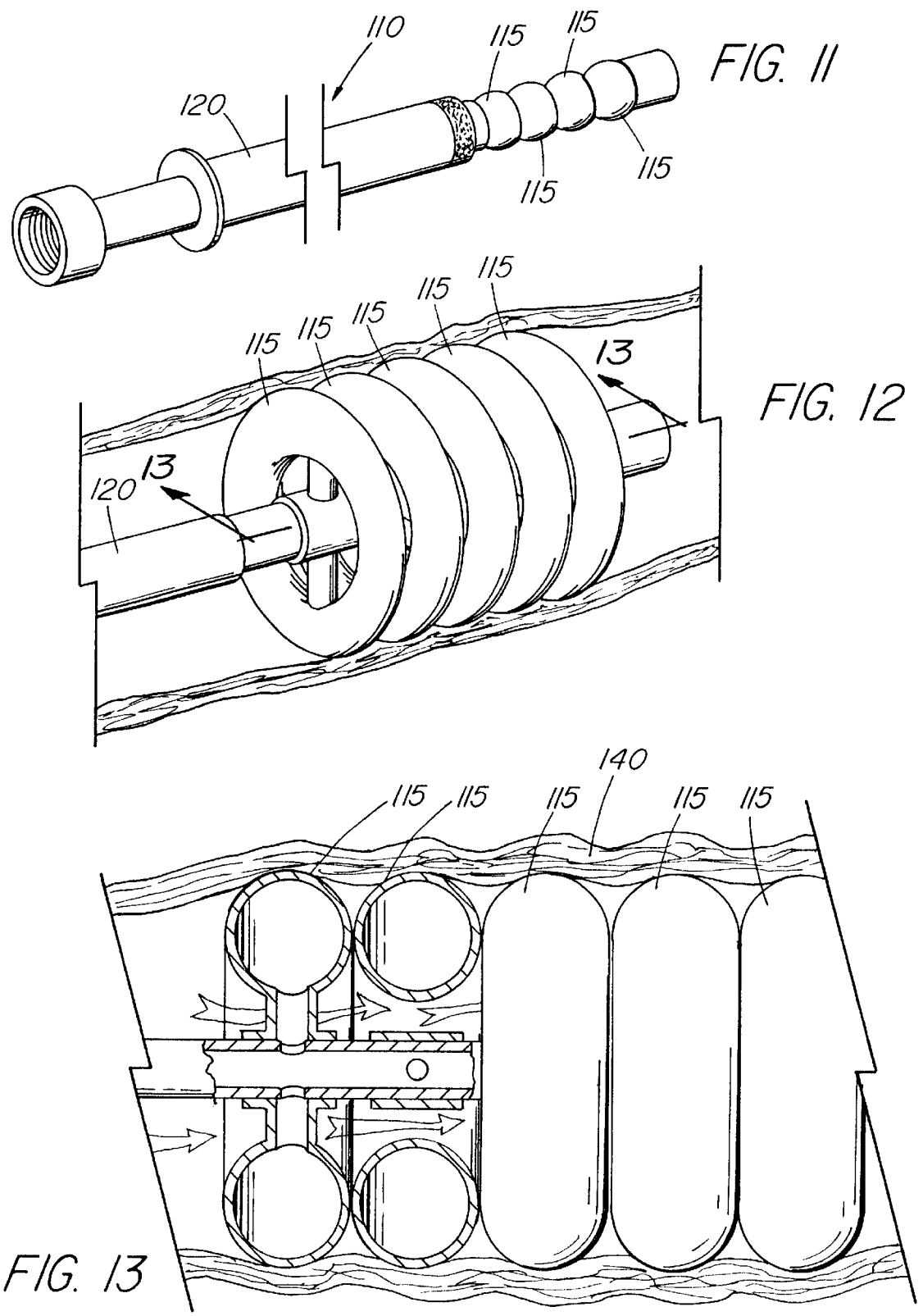
FIG. 11 is an assembly drawing of a fourth embodiment of the catheter system of the present invention with the catheter apparatus being deflated.
FIG. 12 discloses a detail view of the fully-inflated catheter apparatus of FIG. 11.
FIG. 13 is a detailed part sectional view of the fully-inflated catheter apparatus taken along line 12—12 of FIG. 12.
Figure 14:
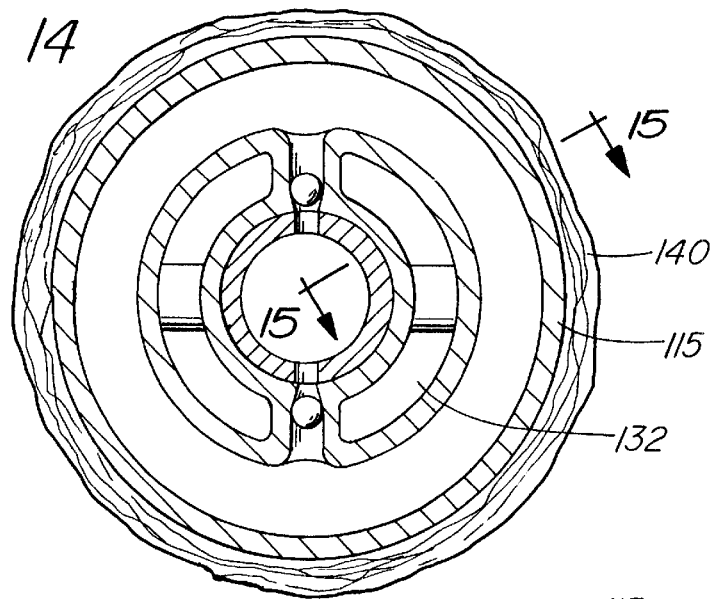
FIG. 14 is a detailed cross-sectional view of the fully-inflated catheter apparatus of FIG. 11.
Figure 15:
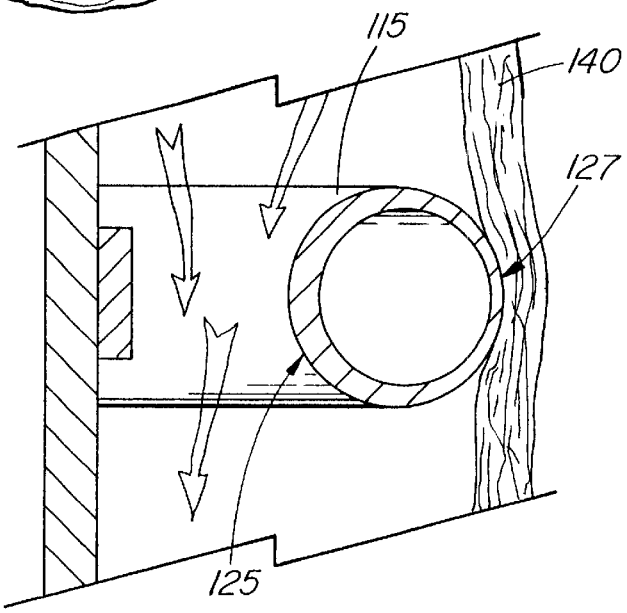
FIG. 15 is an exploded sectional view of a fully-inflated balloon of the catheter apparatus of FIG. 14, the balloon having a thickened inner wall and a thinner hypo-dense outer wall.

Preferably, either three discrete balloon sections are used as shown in FIGS. 1 through 6, or four balloon sections 22, 24, 26 and 28 with interposed sections 32, 34, 36 and 38 can be used as shown in FIGS. 9 and 10.

One primary application of the system of the present invention is for use after standard, angioplasty procedure: including multiple lesions at one treatment session. Controlled internal radiation therapy is provided to an artery or vessel for the prevention of arterial restenosis due to smooth muscle hyperplasia or similar related pathology. This will enable cannulation via the same access port from the preemptive dilatation procedure.

Discrete balloon sections or segmented systems 22, 24, and 26 or possible variants thereof are specifically structured to enable the application of a radioactive gas for therapeutic intent.

FIGS. 11 through 16 disclose another embodiment of catheter apparatus 120 of the present radiation delivery device invention. Drafted segmental and peripheral "tire-like" balloon sections or segment configurations 115 optimize direct circumferential abutment of the entire lumen wall. This will minimize intraluminal attenuation factors and maximize homogenous dose rate delivery, conforming and enabling irregularly-shaped intimal surfaces. Also, when the catheter segments 115 are pressurized and expanded, a significant residual rate of intraluminal blood flow is enabled internal to the segments.

The catheter apparatus of the present invention is designed to minimize the secondary risk of medical complications caused by blood flow deficiency due to underlying disease or vasospasm in the peripheral, kidney, and, particularly, the heart vessels. The centrally directed perfusion flow can also contribute to outwardly directed pressure gradients, therefore, further supporting and stabilizing the radioactive-gas expander balloons against the arterial wall.

The catheter apparatus of the present invention enables individual patient flexibility as to dosage, treatment exposure time, and lesion segment lengths. Also, since blood flow cannot be completely occluded during therapy, radiation time need not be limited to less than three minutes, and therefore, very high energy gamma emitters or radiation activity levels are not needed. More expensive loading devices, shielded treatment rooms, and solid radio sources are thereby avoided. Also, healthy tissue is not unnecessarily exposed to passing or placement-preparation time irradiation as with other solid-source systems.

If inadequate blood flow rates or distal symptoms occur, this closed, sealed and inert radioactive gas system 10, 110 can be easily deflated without exposing the patient or medical personnel to real radiation risk. After flexibly allowing for several minutes of reperfusion time, the catheter apparatus 20, 120 can be simply reinflated and the prescribed treatment time/dose (several times if needed) is resumed without diminishing the therapeutic benefit.

Furthermore, the system of the present invention enables the treating therapeutic radiologist to address more than one vessel system or lesion even distal to the distribution of the primary lesion that may require subjective variation in post-dilatation balloon length and diameter due to sensitivity of distal ischemic-prone tissue from risk of prolonged diminished blood flow.

The sectioned, segmented or compartmentalized radioactive gas delivery tracks communicating with the end point expander balloons, will minimize the potential volume of gas leak should a balloon lose integrity. The residual catheter gas volume may be withdrawn into the shielded syringe without further leakage. The bloodstream released gas poses no real radiation or chemical threat to the patient, because of the physical and biological properties of the inert gas.

Figure 16:
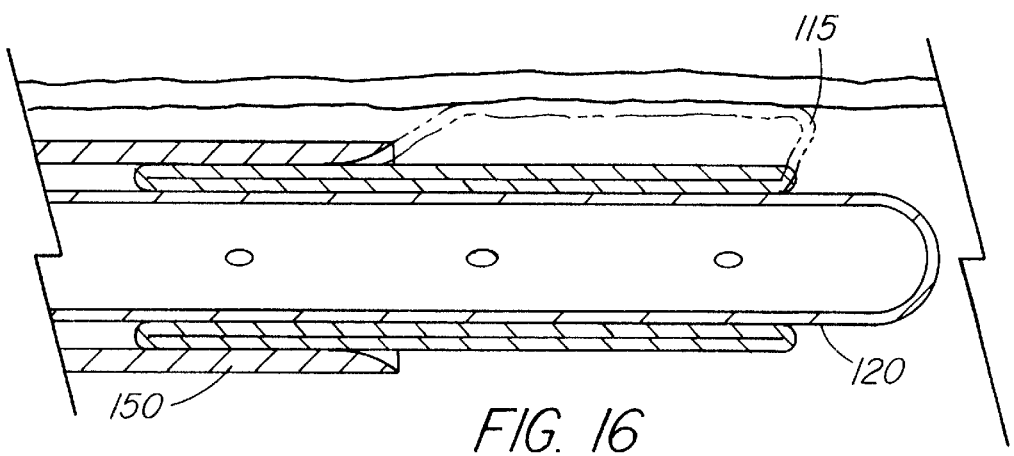
FIG. 16 is a detailed sectional view of the partially-inflated catheter apparatus of FIG. 11, complete with the retractable sleeve.

The length of the distal expandable component of the catheter apparatus 20 or 120 is covered by a thin, retroslidable or static sleeve 50 or 150, as shown in FIGS. 4 and 16, which is radiopaque for purposes of imaging localization. The sleeve 50 or 150 is in direct continuity with and manipulatable externally by the physician. The sleeve is positioned proximal to the access port to the balloon sections or segments. After confirmation of placement of the distal catheter apparatus 20 or 120 by fluoroscopic means, the catheter sleeve 50 or 150 is slowly pulled back, and a concordant ruler is exposed in parallel, measured in millimeters, whereby the treating physician accurately determines the length of the balloon to be expanded, and the length of the vessel wall to be treated 40 or 140. Alternatively and preferably, indicator 21 can be utilized to establish selectively the dosage rate as illustrated in FIG. 32. This will enable immediate confirmatory calculations as to specific dose rates, treatment time, and the volume of the radioactive gas injected.

The proposed radioactive gas or gases emit gamma photons enabling imaging and semi-log calculations to be performed at bedside using a conventional gamma camera and computer (not shown), which is left on the monitor distal to the treatment field to detect any early leakage for concerned physicians at minimal additional cost.

Although the lumen diameter is narrow and contains only a small fraction of the total volume of radioactive gas injected per session, the designed shielding properties of the sleeve 50 or 150 or outer lumen wall layer minimize any significant normal tissue or blood cell exposure over the remaining non-inflated catheter length, particularly with the energies of emission of the isotopes selected.

The interval and possibly staggered placement design of the entry portals and columns between the catheter body and expansion "modules" or balloons enable cutoff control of the balloon expansion length due to the controlled length of outer sleeve retraction.

The primary rationale and benefits for the therapeutic application of radioactive xenon gas with the "ASP" or similar catheters for intravascular brachytherapy enable precise determination of total dose, dose rate, and depth distribution of radiation emitted from a source.

Radioactive xenon-133 gas, and less commonly used xenon-127 gas and krypton 85, as well as, technetium compounds, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Rapid expulsion of the relatively lower energy nuclear emissions of the xenon, is quickly re-released from the bloodstream through the lungs.

Xenon is a very stable element which can be pressurized, stored, and made to high millicurie activity per cubic centimeter (cc) with very reasonable cost and availability.

Xenon-133 provides both a beta particle (101 keV avg.; 364 keV max.), and at least two usable photons (32 keV 48 percent; 81 keV 37 percent).

The beta particles offer excellent initial dose rate delivery when directly adjacent to the tissue with the first millimeter. The particle does not penetrate much beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mCi to 150 mCi per cc or more of gas volume. Also, the cost is currently estimated to be less than a few hundred dollars a dose of 150 mCi. A single dose order can be used to treat several patients per day for a full week, as the physical half-life is 5.2 days. Also, no special equipment, storage, or delivery devices are necessary, except for routine facilities available in most nuclear medicine or radiation oncology departments.

In vivo and in vitro facilities with standard exhaust hoods or negative pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachytherapy. The most expensive addition to a standard treatment room is a simple negative pressure ventilation system, as a backup safety mechanism.

Selective balloon shapes and designs with various thicknesses and pliable lucent and radio penetrable materials enable site specific, intracavity or intraparenchymal insertion and localization from external origin and placement. FIGS. 17, 18, and 19 illustrate various other applications for catheter apparatus 220 which can include brain, lung, esophagus, trachea, cervix, biliary ductal system, colon or rectum, the gastrointestinal system, the gynecological system, and head and neck. All can optimize the self-introduction of radioactive xenon-133 or others, with controlled expansion and dose rate delivery while enabling individual tissue compliance such that the entire tissue is immediately and homogeneously adjacent to this high or low dose rate source without requiring surgical implant disruption, patient isolation, use of high energy concentrations of other radionuclides, patient or medical personnel risk from leakage, expensive materials, or costly radio-safe suite facilities.

The compliance, stress, and thickness properties of the balloons enable adequate and complete volume expansion against the variable surface of the arterial wall at less pressure than conventional therapeutic dilation plasty catheters.

Figure 20:
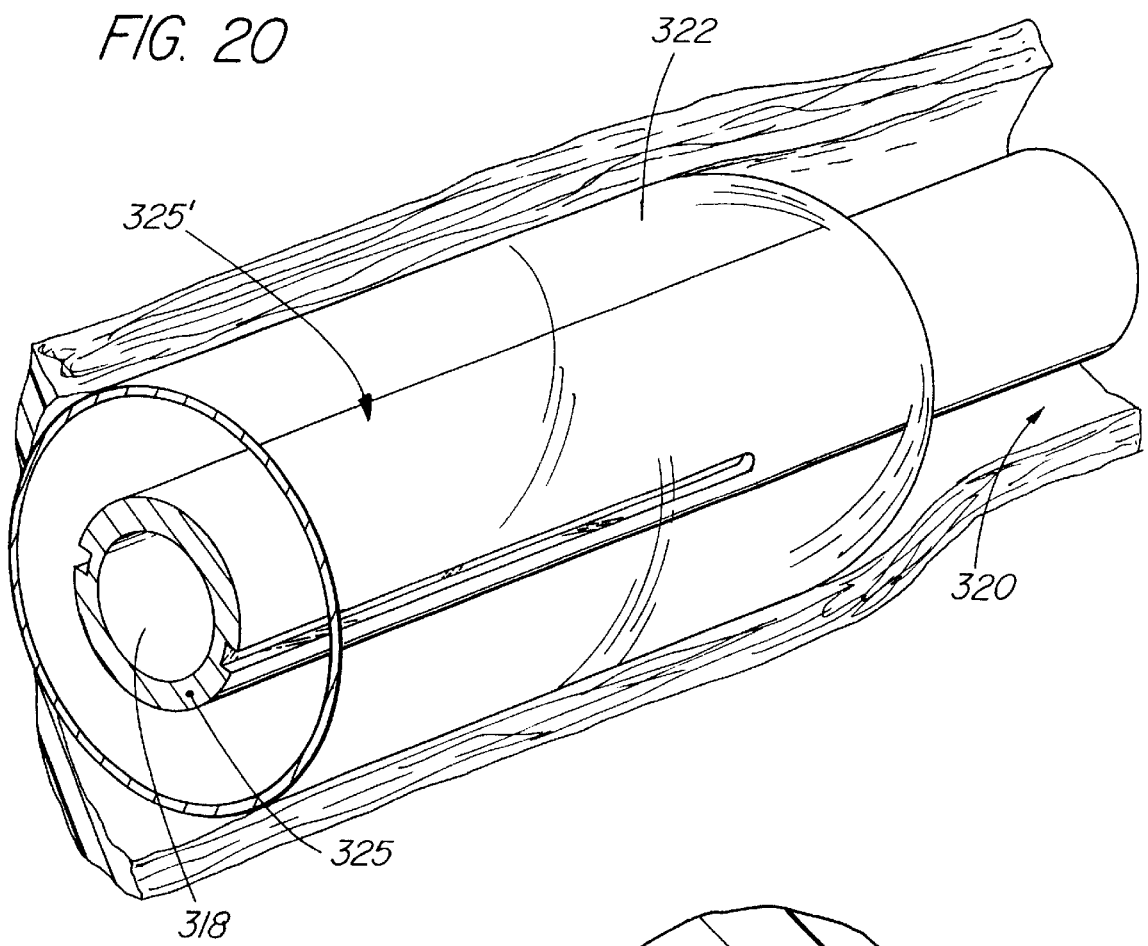
FIG. 20 is an enlarged partially sectioned assembly drawing of a sixth embodiment of the catheter system of the present invention, with a single balloon fully inflated as the blood flows through the center section of the apparatus.
Figure 21:
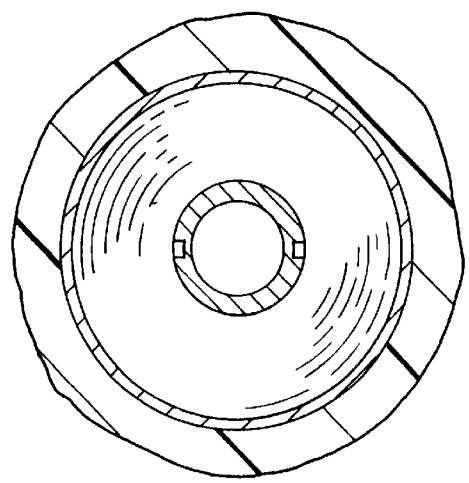
FIG. 21 is a cross-sectional end view of the catheter system of FIG. 20.

FIGS. 20 and 21 disclose yet another embodiment of the catheter apparatus 320, the catheter comprising an inner lumen 318 (with wall 325) for the transmission of blood when the catheter is inserted into a blood vessel. A specific coating of integrated and layered transitional metal or metal alloy compounds from the surface to the center of the exterior side 325' of the wall of the catheter lumen 318 protects the blood in the lumen from radiation, and enhances the radiation dosage delivered to the target. Either the heavy transitional metals or denser ranges of heavy metals are recommended, such as titanium, tungsten, aluminum, and germanium. The alloys can also include silicon. As used herein, the term "metal" includes pure metals, metal alloys, and metal alloy compounds.

FIG. 20 shows a balloon 322 extending around the inner lumen, and expanded by radiation fluid, the expanded balloon being in contact with the internal wall of a blood vessel 324. The lumen wall 325 attenuates the transmission dosage to the blood circulating through the hollow inner lumen of the central catheter apparatus 320. In addition, the system creates increased by-product radiation, bremmstrahlung and incidental scatter, from the impact of beta particles and gamma photons traveling into or toward the lumen wall 325. This energy, which would otherwise be wasted, produces by-product low-energy x-ray photons, which increase the deposited energy dosage into the target tissue via scattered angle coincidence or secondary redirected x-ray production from the slowing of beta particles traveling into or next to the metal compound on the wall surface 325'. These particles might ordinarily be considered too far from or having too little energy to reach the target tissue. However, the by-product x-rays (bremmstrahlung radiation) travel through the balloon outer wall and deliver useful radiation dosage over a range of several hundred micrometers to the targeted tissue.

Figure 22:
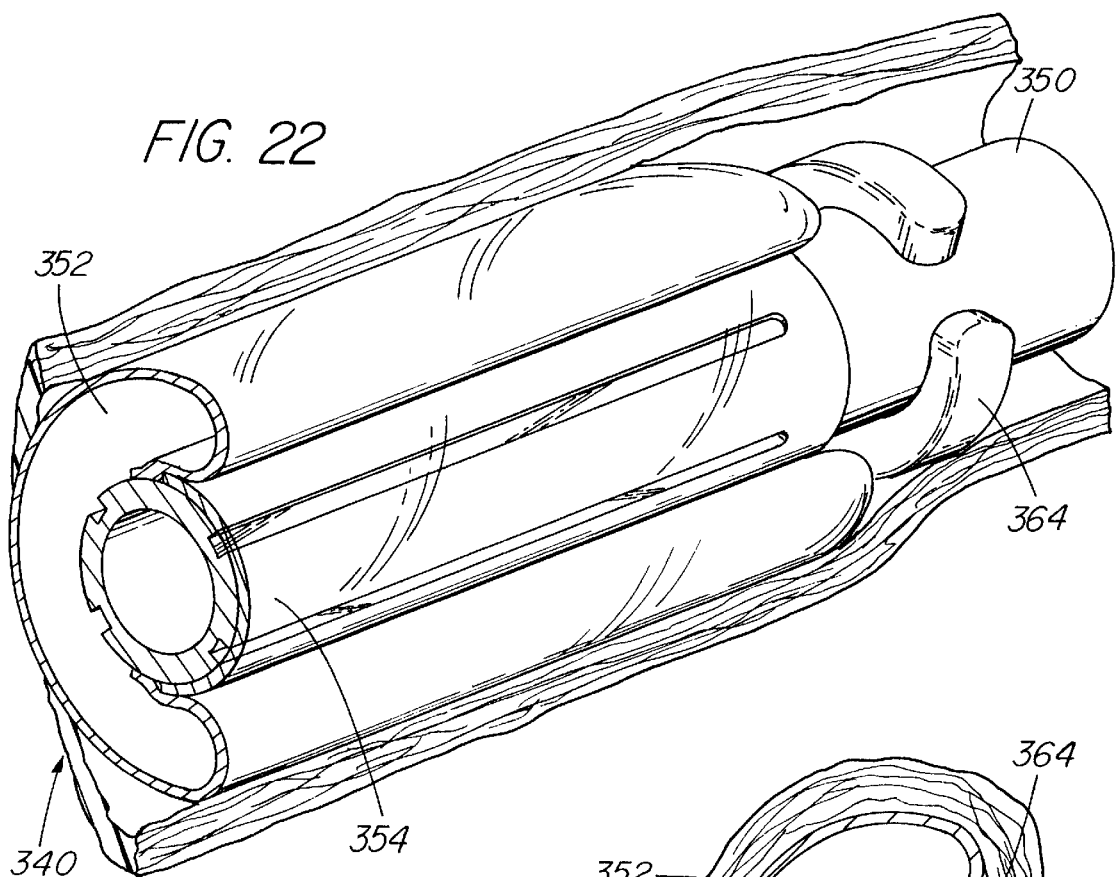
FIG. 22 is an enlarged partially sectioned assembly drawing of a seventh embodiment of the catheter system of the present invention, with two separate, semi-circular balloons, one balloon being inflated and delivering a treatment dose, while the opposing balloon is deflated.
Figure 23:
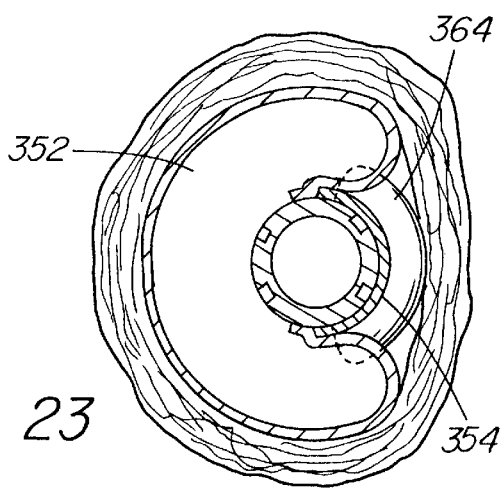
FIG. 23 is a cross-sectional end view of the catheter system of FIG. 22.
Figure 24:
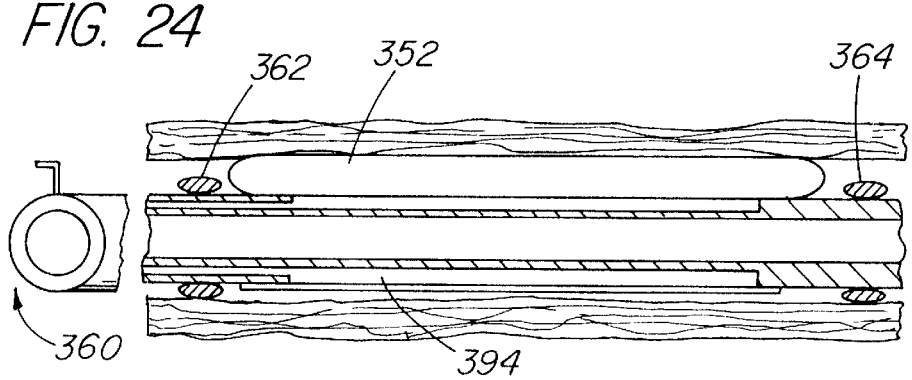
FIG. 24 is a longitudinal sectional view of the catheter system of FIG. 22.

Still another catheter apparatus 340 is disclosed in FIGS. 22, 23 and 24. Two opposing and separate, semi-circular balloons 352 and 354 include opposed support displacers 362 and 364 attached just proximal and distal to the balloon lengths upon the outer lumen wall 350 of the inner lumen.

An injection port unit 360 enables fluid-tight redirection of radioactive fluid flow from between the balloons 352 and 354. Thereby, while one balloon 352 is inflated and delivering treatment dosage, the opposing balloon is deflated 354. The support displacers 362 and 364 are juxtaposed against the vessel wall enabling blood to flow more easily through the space opposite to the treatment side.

The single-unit injection port 360 with synthetic septum is fluid-tight and leak-proof. The port 360 is preferably made of Viton rubber, enabling easy needle penetration without loss of gas under pressure via leaky adaptive Luerlock additions.

The radioactive xenon gas can be partially dissolved in sterile saline or lipid-containing solution for solubilizing the xenon. The resulting material can then be injected into a balloon system.

It is also contemplated that the dosimetry unit of measurement indicator 21 disposed, affixed, or positioned on a delivery device can be an electronic display panel such as LCD or LED. The display panel indicator can be connected to an electronic radiation sensor or detector positioned at that portion of the device for treating tissue. Such displays and detectors are commercially available.

Figure 35:
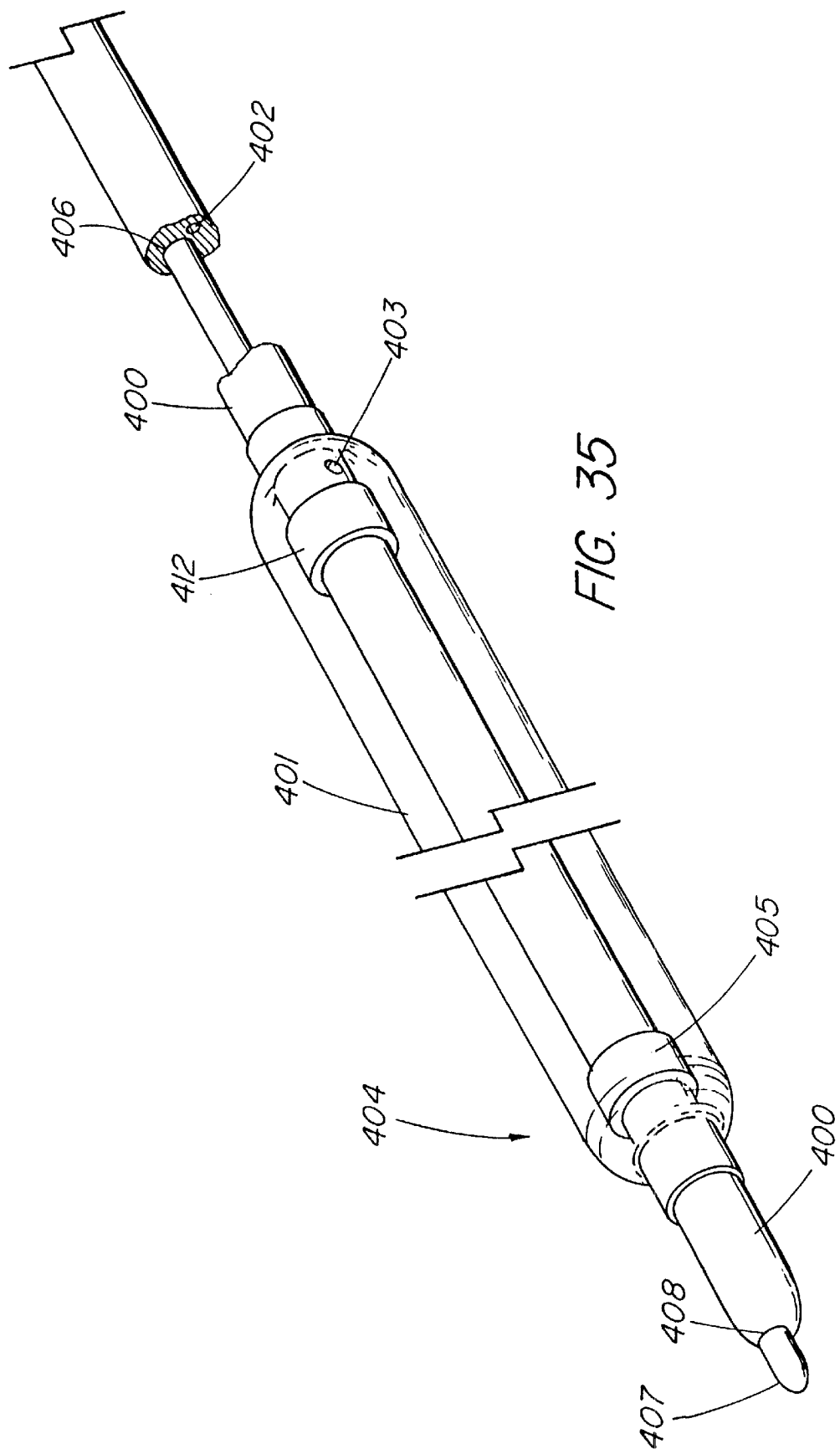
FIG. 35 is a partial perspective, partial sectioned view of yet another embodiment of the present invention.

Still another embodiment of catheter apparatus 400 is depicted in FIG. 35. A single angioplasty-style balloon 401 is mounted about the distal end 404 of the catheter 400. The balloon, which typically is under slight negative pressure just prior to treatment, is inflated with radioactive fluid that travels though inflation lumen 402 and enters the balloon at inflation port 403. In this embodiment, the inflation lumen 402 is made much smaller that in a typical balloon catheter 400 in order to minimize the amount of radioactive fluid in the catheter during treatment. This has the advantage of reducing potential exposure to the operator and non-target tissue of the patient, as well as reducing the amount of the costly radioactive source material needed to achieve the desired dosimetry at the treatment site. The size of the inflation lumen 402 is primarily limited by the tooling required to form the small lumen, typically, but not limited to approximately 0.010" in diameter. Radiopaque markers 405, 412 positioned near the proximal and distal ends of the balloon 401 aid the operator in placement of the balloon 401 under fluoroscopy. An alloy of tungsten and iridium makes an excellent radiopaque material, but almost any biocompatible radiopaque material can be used. The catheter 400 further includes a second lumen 406 through which a wireguide 407 can be introduced to assist in placement of the balloon 401 at the treatment site. The wireguide lumen is sufficiently large (typically over 0.020" in.) to accommodate a standard coronary wireguide. The wireguide 407 exits the catheter 400 through an orifice 408 at the catheter's distal end 404.

FIGS. 36—41 depict alternative methods of providing shielding to protect the patient and/or operator from radiation outside of the intended balloon source. FIGS. 36–38 are cross-sectional views of the catheter embodiment of FIG. 35, while FIGS. 39–41 represent cross-sectional views of a catheter embodiment similar to FIG. 35, except lacking the second larger guidewire lumen 406. FIGS. 36 and 39 depict a catheter 400 that has been loaded with a high density shielding material 409 including, but not limited to barium, tungsten, lead, tantalum, titanium, bismuth, gold, platinum, palladium, rhodium, or any other similar suitable material, or a combination thereof. A load of 20% barium sulfate, provides good shielding properties and excellent radiopacity without comprising the integrity of the catheter. Much higher amounts of shielding material can cause failure of the bonds between the balloon material and the catheter. FIGS. 37 and 40 depict catheters 400 that have had shielding added by the addition of a layer 410 of metal ions that have been deposited on the outside surface of the catheter 400 by a technique such as ion beam deposition (Spire Corp., Bedford Mass.). Another method or producing such a layer would be to shrink or bond a plastic film containing metal ions to the outer surface of the catheter 400. FIGS. 38 and 41 depict catheters 400 that are shielded by a outer sleeve or guiding catheter 411 which is loaded with a shielding material such as barium sulfate. Since bonding is not applicable for a such a sleeve, the amount of metal added to the plastic can be higher than that for the balloon catheter 400. The shielding sleeve 411 can comprise the entire length of the catheter (leaving the balloon portion exposed), or can be used only on the portion of the catheter that is outside the body in order to protect the operator handling the delivery system.

Figure 42:
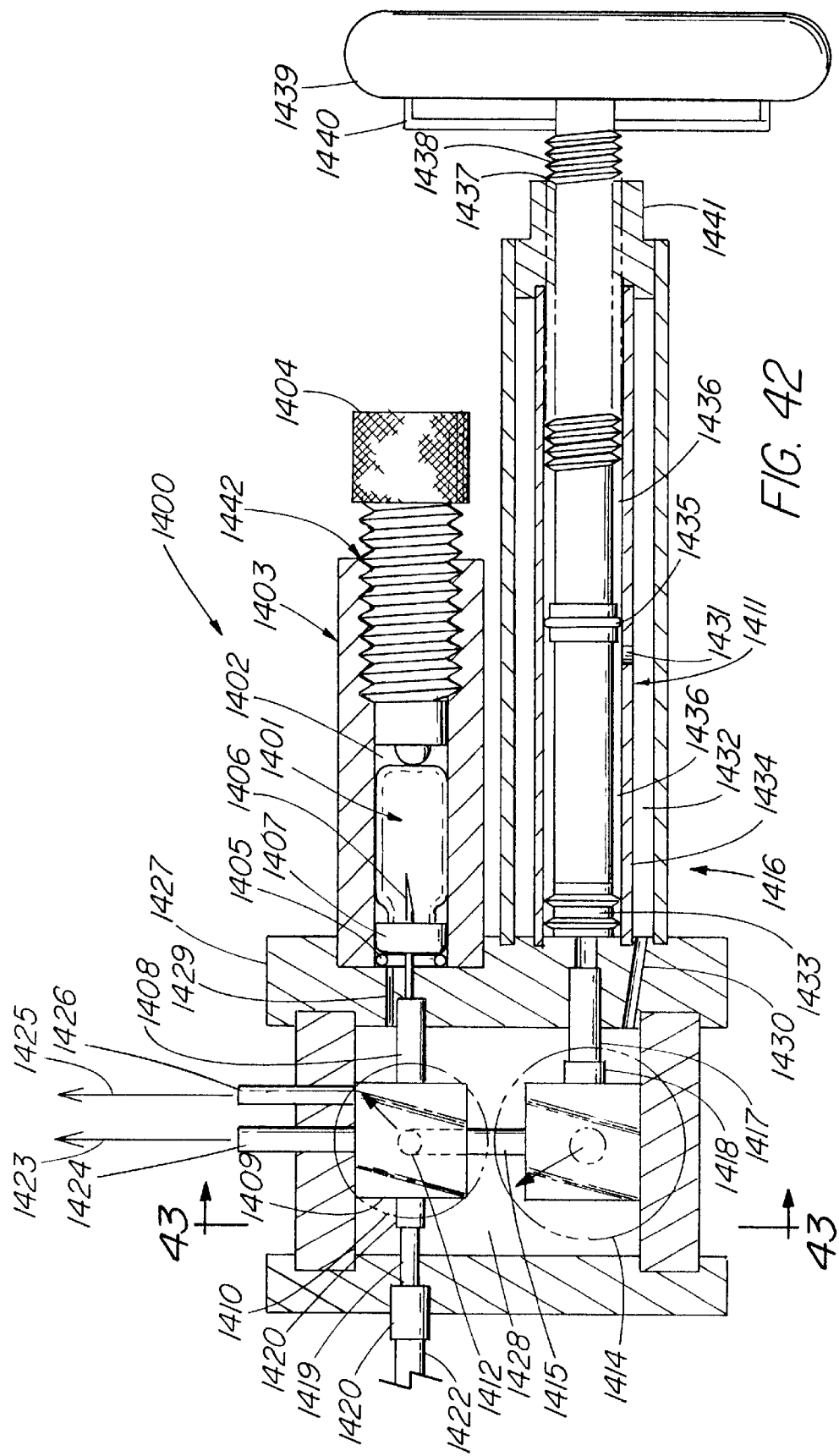
FIG. 42 depicts a partially sectioned top view of the a first preferred embodiment of a delivery apparatus of the present invention.
Figure 43:
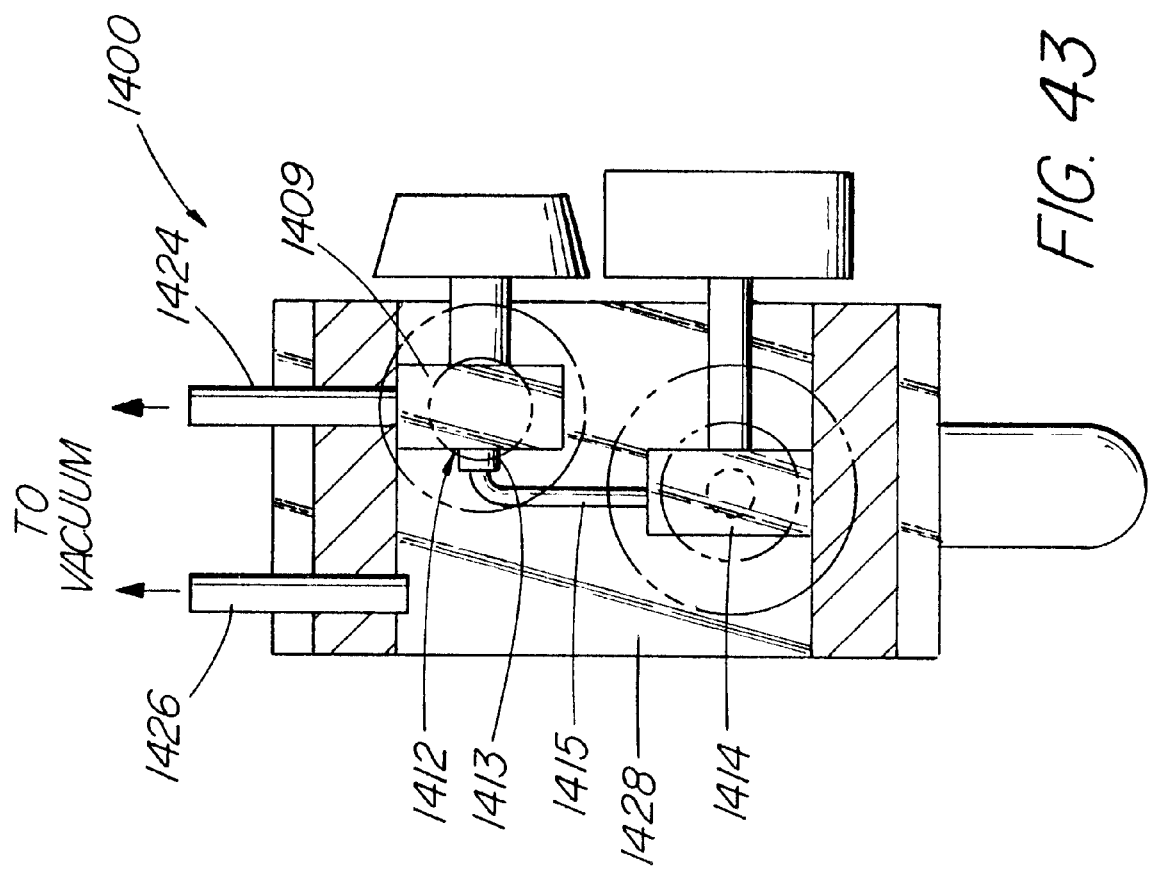
FIG. 43 depicts a partially sectioned, front view of the delivery apparatus of FIG. 42.

FIG. 42 depicts a partially sectioned top view of a medical radiation treatment delivery apparatus 1400 of the present invention, more details of which are shown in FIG. 43. The delivery apparatus 1400 basically includes a radioactive gas vial enclosure, such as source vial housing 1403; a selector mechanism such as a multiple position valve 1409, and a gas-tight, variable volume chamber such as a gas-tight syringe 1411 interconnected as depicted by passageways, lines, connectors, ports, or cannula 1406, 1408, 1412, 1413, 1415, 1417–1421, and 1424 to radiation delivery balloon catheter 1422. A commercially available fluid pressure guage 1414 is positioned between cannula 1415 and 1417 using for example, a well-known connector 1418. Multiple position valve 1409 and, preferably, four-way valve 1409 is interconnected between connector 1408 and 1420, cannula 1415 and vacuum line connector 1424. Valve 1409 includes a selector knob 1421 to interconnect main cannula 1415 selectively to vial connector 1408, catheter connector 1420, and vacuum line connector 1424. Delivery apparatus 1400 includes valve gauge housing 1427 for housing the pressure gauge and the four-way valve along with the associated previously described lines, connectors, ports, or cannula within chamber 1428. As a safety feature, an additional vacuum line 1425 is attached to secondary vacuum line 1426 for evacuating any radiation fluid from within chamber 1428. A primary vacuum line 1423 is connected to the multiple position or four-way valve 1409 for evacuating radiation fluid via the valve 1409. In order to provide additional safety for the operator and patient, the outer housings material of the delivery apparatus may also include a high density material of at least one of barium, tungsten, lead, tantalum, titanium, bismuth, gold, platinum, palladium, rhodium, or any other similar suitable material for shielding from beta and gamma particles emitted by the radioactive source material. This shielding material may incorporated into the plastic housing and/or comprise a lining or chamber enclosing the source vial or delivery syringe.

Delivery apparatus 1400 further includes source vial chamber enclosure 1403 such as housing 1403 attached to valve gauge housing 1427. Included in the source vial chamber housing 1403 is source vial chamber 1402 for positioning source vial 1401 therein. The source vial enclosure 1403 includes an enclosing means 1404 that permits loading of the gas vial into the chamber and also serves to seal the enclosure 1403 to prevent gas leakage. Extending from vial connector 1408 is well-known piercing cannula 1406 extending into chamber 1402. A source vial 1401 is positioned in chamber 1402. The source vial includes a radiation fluid such as, but not limited to, Xenon-133 gas therein for delivery to an external device 1422, such as a balloon delivery catheter 1422. The source vial 1401 is inserted in chamber 1402 and urged toward piercing cannula 1406 via an urging mechanism 1442 such as a threaded chamber cap 1404, which comprises the enclosing means 1404 for the gas vial enclosure and the maintains a gas-tight seal for chamber 1402. In the illustrative embodiment, urging mechanism 1442 such as a threaded chamber cap 1404, is threaded into the chamber. The inner surface of the urging mechanism 1442 contacts the vial 1401, which is urged forward to contact the fixed piercing cannula 1406. The piercing cannula 1406 extends through the vial septum 1407 of source vial 1401 for establishing communication with the radiation fluid contained therein. The source vial septum 1407 is urged forward to one end of the vial chamber 1402 to engage O-ring 1405 to maintain a gas-tight seal. Should any radioactive fluid escape the vial 1401 and enter chamber 1402, communication channel 1429 extending between chambers 1402 and 1428 permits secondary vacuum line 1425 attached to the secondary vacuum port 1426 to scavenge the fluid therefrom.

Delivery apparatus 1400 also includes syringe housing 1416 connected to valve-gauge housing 1427. A gas-tight syringe 1411 is positioned in syringe housing 1416 and connected to the pressure gauge 1414 by cannula 1417. Communication channel 1430 communicates with air space 1432 and 1436 for evacuating any radioactive gas or fluid that escapes the syringe 1411. Secondary syringe communication channel 1431 interconnects air space 1432 and 1436. Syringe housing 1416 is enclosed at one end with threaded collar 1441 through which well-known and commercially available threaded advancing mechanism 1438 connected to handle 1439 and thread release mechanism 1440. Opening 1437 around advancing mechanism 1438 allows air to be drawn into the syringe housing to permit evacuation of escaped radioactive fluid. At the other end of the housing is syringe barrel 1434 in which syringe plunger 1433 is positioned. Well-known O-ring 1435 is positioned at the proximal end of the plunger to maintain a gas-tight seal.

The syringe plunger 1433 is used to evacuate fluids such as air or radiation fluid from the delivery catheter when the multiple position valve 1409 is appropriately positioned. The gas-tight syringe 1411 and plunger 1433 are also used to evacuate and return air or radiation fluid to and from the source vial 1401, the vacuum line 1425 or the delivery catheter 1422 with appropriate selection of the multiple position valve.

The method for using the radiation treatment delivery apparatus 1400 involves placing a radiation source vial 1401 within a source vial chamber 1402 thereof, which is then sealed. The source vial 1401 is advanced using an urging mechanism 1442, such as a threaded cap 1482 (FIG. 47), until the septum 1407 of the vial 1401 is pierced by a needle piercing cannula 1406 connected to a multiple position valve 1409, such as a four-way valve. This step can be done by a technician or support personnel prior to bringing the apparatus 1400 to the actual treatment site. Prior to treatment, the apparatus is attached to a radiation delivery device such as a balloon catheter 1422. The vacuum line ports 1424, 1426 of the apparatus are connected to a scavenger system. Treatment is initiated with the catheter passageway 1419 which leads to the catheter 1422, being selected and the plunger 1433 of the syringe 1411 being withdrawn to evacuate air from the balloon catheter 1422 attached to the apparatus. The multiple position valve 1409 is then switched to the primary vacuum line 1423 and the air from the syringe 1411 is discharged into a commercially available radioactive gas scavenger unit. The multiple position valve 1409 is then positioned to passageway 1406 and source vial 1401, and the syringe 1411 is loaded with the radioactive gas. To treat the patient, the multiple position valve 1409 is positioned to the catheter passageway 1419, and the syringe plunger 1433 is advanced, preferably using a threaded advance mechanism 1438, until the radioactive gas is completely transferred from the syringe 1411 to the catheter 1422. After the prescribed dosage period, the radioactive fluid is evacuated into the syringe 1411. The multiple position valve 1409 is then positioned to passageway 1406 and source vial 1401. and the gas is returned to the source vial. The multiple position valve 1409 is switched to the vacuum line 1423 to evacuate some of the remaining gas in the system.

FIG. 43 depicts a partially sectioned front end view of injection apparatus 1400 of FIG. 42. This particular figure illustrates the interconnection between the multiple position valve 1409 and pressure guage 1414 via the gauge to valve cannula 1415 and connector 1413 that attaches at the syringe port 1412 located in this particular embodiment at the underside of the multiple position valve 1409 Primary and secondary vacuum line connectors 1424 and 1426 are also depicted with respect to the multiple position valve 1409 and valve-pressure gauge chamber 1428.

FIG. 44 is a partially sectioned side view of a second embodiment of the injection apparatus 1400 of the present invention. The apparatus includes a system for extracting a radioactive fluid such as xenon-133 gas from a source vial 1401 by drawing the fluid into a gas syringe 1411 under negative pressure, where it is then injected into an external device such as delivery catheter 1422 depicted, for example, in FIGS. 1–41. As a safety measure, the apparatus can be attached to a well-known scavenger system to carry away any radioactive fluid that remains in the apparatus following treatment or that might leak from or around one of the connections or seals. The components of the radioactive fluid injection apparatus are integrated within an outer housing 1452 that helps shield the user from radiation.

The radiation fluid source vial 1401 is loaded into the apparatus by removing the threaded vial chamber cap 1482 of radioactive gas vial enclosure 1403 and placing the source vial 1401 in the source vial chamber 1402. A plunger 1444 is slidably attached to the cap that receives the bottom end of the source vial when the vial is within the chamber. A locking handle 1443 on the shaft 1456 of the plunger, as shown in a cross-sectional view in FIG. 45, is rotated around the shaft 1456 to a position that allows the plunger to be advanced using the external handle 1446. The source vial 1401 is advanced within the source vial chamber 1402 until a piercing cannula 1406 pierces the septum 1407 of the vial. Piercing cannula or passageway 1406 supplies radioactive gas from source vial 1401 to an external device such as a balloon catheter 1422. A spring 1445 attached about the shaft 1456 of the plunger provides tension against the source vial 1401 to hold the vial in place. An alternate embodiment of the piercing cannula 1406 as depicted in FIG. 46. In this embodiment, the piercing cannula is protected by a plastic sheath 1462 held in place by an attached spring 1449 that compresses with the advancing source vial 1401, forcing back the sheath 1462 and allowing the exposed tip of the cannula or passageway to puncture the vial septum.

Returning to FIG. 44, any leakage of radioactive fluid between the piercing cannula 1406 and septum 1407 is drawn from the source vial chamber 1402 via one or more vacuum ports 1450 that attach to a standard radioactive gas scavenger system. After the source vial 1401 has been punctured by the piercing cannula 1406, the multi-position valve 1409 is positioned so that the source vial 1401 communicates with the gas-tight, variable volume chamber such as syringe 1411. The radioactive fluid in the source vial 1401 enters the gas syringe 1411 when the syringe plunger 1433 is withdrawn using the external handle 1439. A double seal on the head 1472 of the plunger 1433 helps prevent leakage of the fluid into the air space 1436 between the plunger and the syringe housing 1416. Any fluid that leaks into this air space 1436 is aspirated through the vacuum port 1451 into a standard external radioactive gas scavenger system. In the illustrated embodiment, an enclosure sealing mechanism 1447, such as a threaded cap 1447 is used to enclose the syringe chamber housing 1416. An O-ring 1448 provides a seal between the syringe chamber housing 1416 and the threaded cap 1447.

Once the gas-tight syringe 1411 has been loaded with radioactive fluid, the multiple position valve 1409 is positioned to passageway or cannula 1419 to allow communication between the gas-tight syringe 1411 and the radioactive fluid delivery catheter 1422. A connector 1421 is located at the distal end 1490 of the injection apparatus 1400 to which the delivery catheter 1422 is attached. In the illustrated embodiment, a threaded coupler 1475 attaches to the connector 1421 which is also threaded. The air space 1474 created within the coupling after it is attached to the catheter communicates with a vacuum channel 1473 that leads to the outgoing vacuum line 1423. Treatment consists of discharging the radioactive fluid in the syringe 1411 into the delivery catheter 1422 for a prescribed period of time to provide a therapeutic radioactive dosage to the target site. During delivery of the radioactive fluid, a pressure guage 1414 is provided to monitor the pressure of the fluid leaving the injection apparatus 1400. After the prescribed period, the syringe plunger 1433 is withdrawn and the radioactive fluid is returned to the syringe 1411. The multi-position valve 1409 is then switched to the source vial position and the radioactive fluid is discharged back into the original source vial 1401. The final step consists of disengaging the source vial 1401 and piercing cannula 1406 to aspirate any radioactive fluid remaining in the system.

Figure 47:
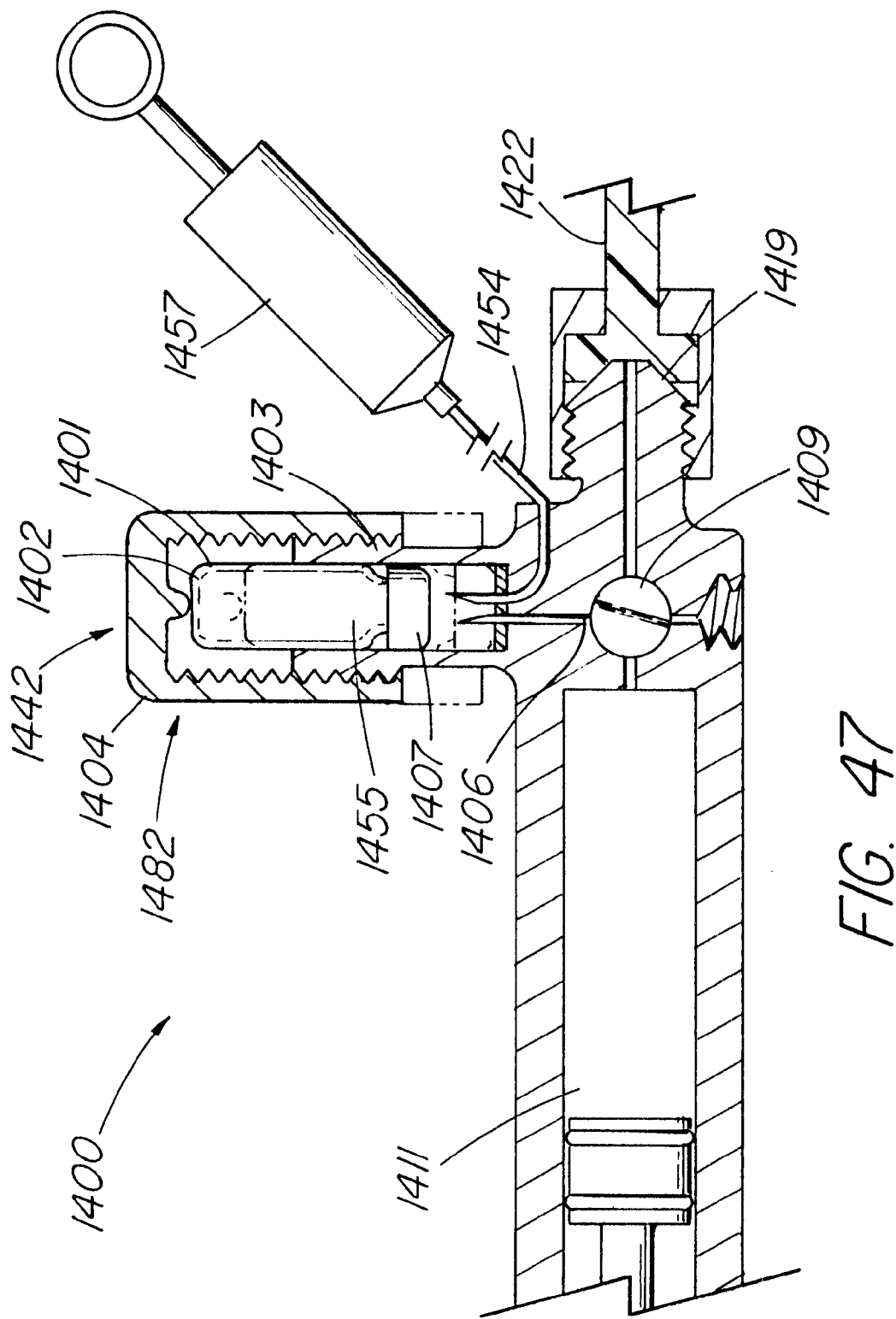
FIG. 47 discloses a sectioned side view of a third embodiment of the delivery apparatus that includes a second syringe to pressurize and displace radioactive fluid from the source vial.

FIG. 47 discloses a sectioned side view of a third embodiment of the injection apparatus 1400 that includes a second syringe 1457 to pressurize and displace radioactive fluid from the source vial 1401. A selector mechanism such as multi-position valve 1409 is positioned for communication between a gas-tight, variable volume chamber such as primary syringe 1411 and the source vial 1401 via passageway or cannula 1406. The secondary syringe 1457 containing an inert fluid is discharged into the source vial via an inlet cannula 1454 that has pierced the septum 1407 of the source vial 1401. The inert fluid fills the space 1455 inside the source vial and displaces the radioactive fluid which is then forced through the outlet piercing cannula 1406 and into the primary syringe 1411. The multiple position valve 1409 is then selected for communication between primary syringe 1411 and the delivery catheter 1422, and the primary syringe 1411 is deployed for treatment. After the gas is withdrawn back into the primary syringe 1411, the multiple position valve 1409 is switched back to permit communication between the primary syringe 1411 and the source vial 1401 into which the remaining gas is returned.

FIG. 48 discloses a sectioned side view of a fourth embodiment of the injection apparatus 1400 that includes a second syringe 1457 to pressurize the gas vial enclosure chamber space 1402 at one end of the source vial 1401 to advance the vial within the enclosure chamber such that the cannula pierces the septum 1407 of the vial. The gas is drawn into a gas-tight, variable volume chamber such as primary syringe 1411 and discharged into the catheter 1422 in a manner similar to the embodiment of FIG. 48.

Figure 49:
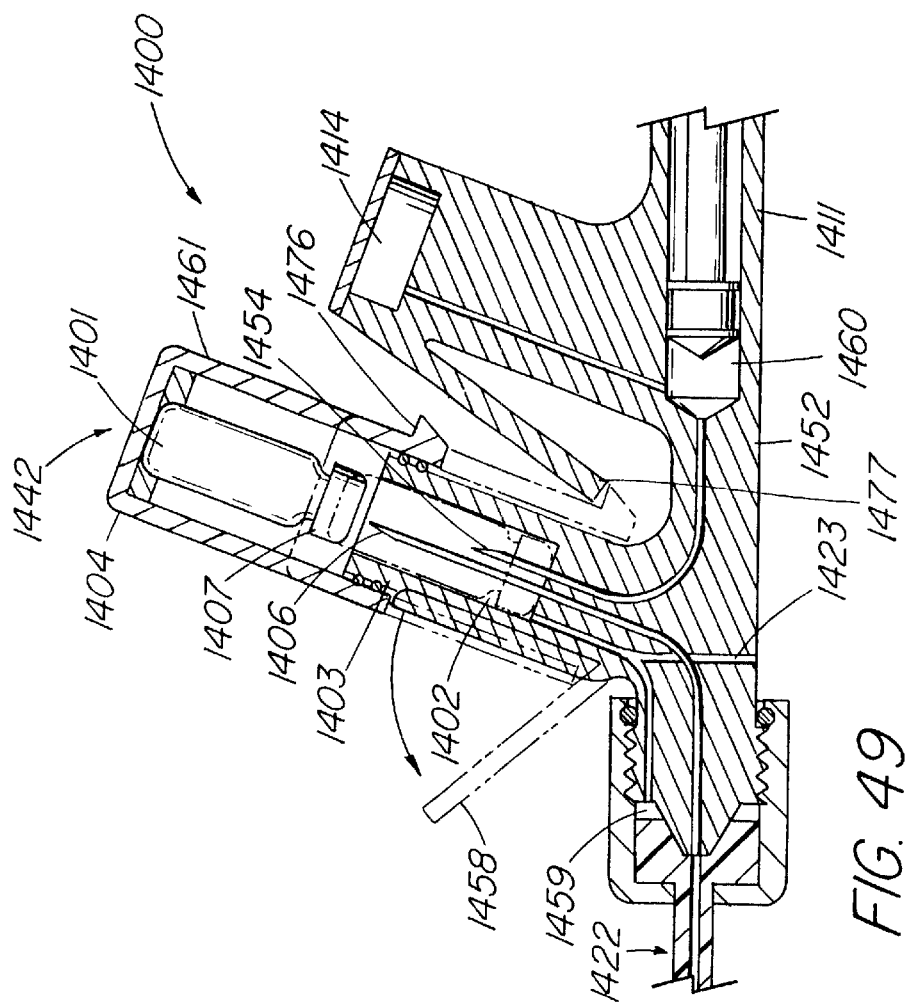

FIG. 49 discloses a partially sectioned side view of a fifth embodiment of the injection apparatus 1400 that includes a gas-tight, variable volume chamber such as syringe 1411 to pressurize and displace radioactive fluid from the source vial 1401 which is contained in vial enclosure 1403, into catheter 1422. A pressure guage 1414 indicates the pressure measured within the internal space 1460 of the syringe. The inert fluid within the primary syringe 1411 is discharged into the source vial via a passageway such as inlet cannula 1454, displacing the radioactive fluid which exits the vial through the outlet cannula 1406 into the catheter 1422. In this embodiment, a safety hinged latch 1458 must be manually displaced to allow a slidable housing 1461 containing the source vial to advance and allow the vial to enter the lower source vial chamber 1402 of enclosure 1403 where the septum 1407 is pierced by the cannulae 1406, 1454. As an additional safety feature, a tab 1476 on the slidable housing engages a catch 1477 on the main housing 1452 to maintain the source vial 1401 in the delivery position throughout treatment.

Figure 50:
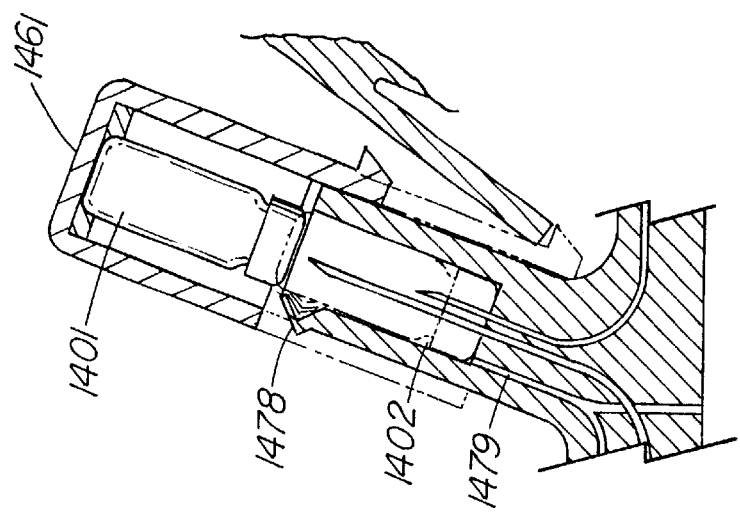
FIGS. 49–50 disclose sectioned side views of a fifth embodiment of the delivery apparatus with a locking slidable source vial housing.

Still an additional or alternative safety feature is depicted in FIG. 50. A vacuum-operated safety latch 1478 prevents the slidable housing 1461 from advancing until a vacuum on the source vial chamber 1402 deploys the safety latch 1478, pulling it inward, to allow the slidable housing 1461 and source vial 1401 to advance into position. The vacuum is created within the source vial chamber 1402 via a channel 1479 leading from the main vacuum line 1423.

Figure 51:
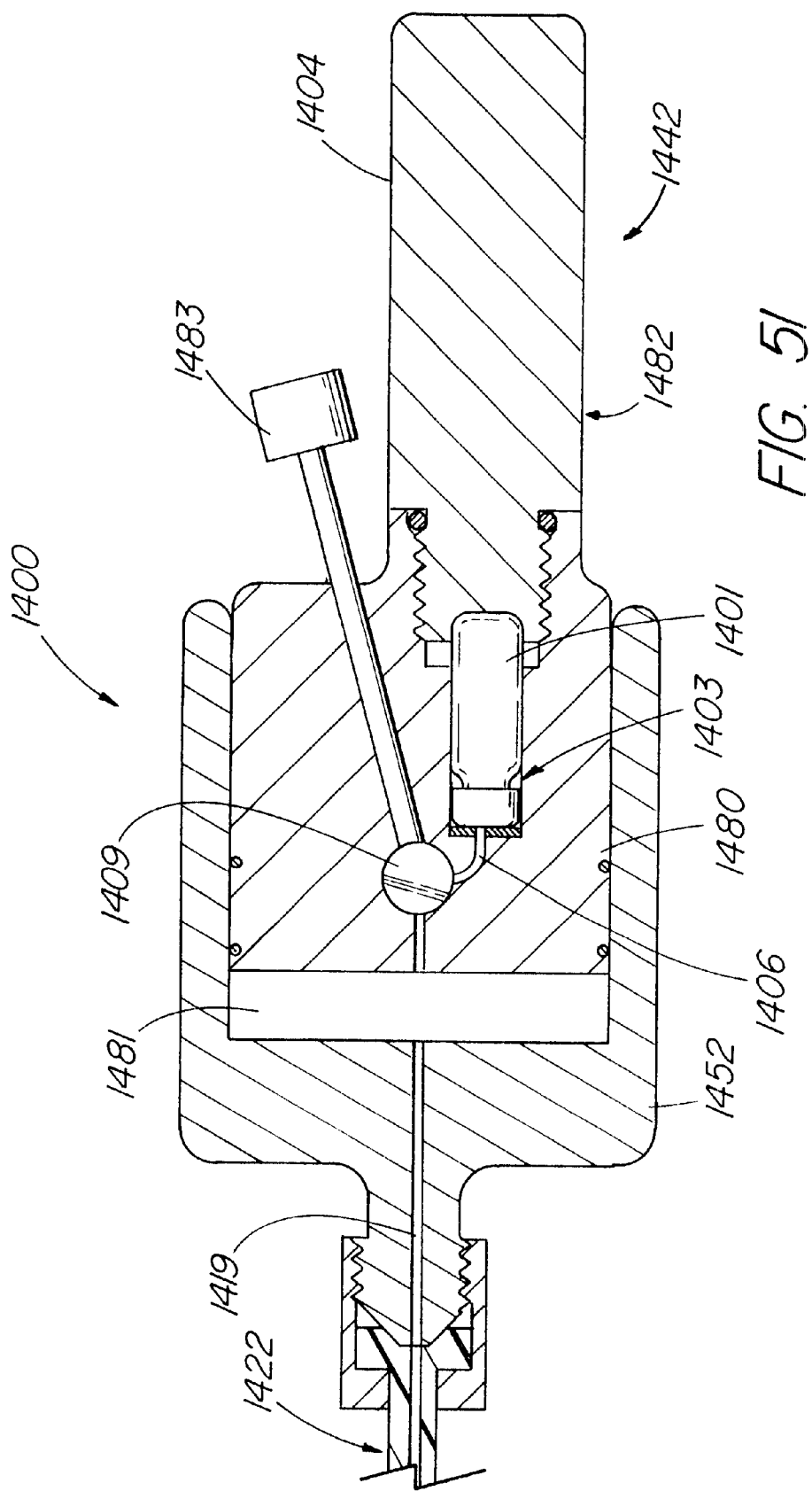
FIG. 51 discloses a sectioned side view of a sixth preferred embodiment of the delivery apparatus in which the source vial housing serves as a plunger for the discharge of radioactive fluid.

FIG. 51 discloses a sectioned side view of a sixth embodiment of the injection apparatus 1400. In this embodiment, the source vial 1401 is placed within gas vial enclosure 1403 that is sealed with a threaded cap 1482. The chamber housing 1403 encases a multiple position valve 1409 that controls the flow of radioactive fluid from the vial to a gas-tight, variable volume chamber such as fluid chamber 1481 within the apparatus. An external knob 1483 controls the position of the valve 1409. The chamber housing 1403 and cap 1482 act as a plunger within the main housing 1452 to compress the fluid chamber 1481 containing the radioactive fluid and discharge the fluid through a passageway such as outlet channel 1419 into delivery catheter 1422.

FIGS. 54–79 disclose a radiotherapy source vial 700 including a radioactive fluid container 701 and a radioactive fluid seal 702 that is movable relative the radioactive fluid container 701. This is to compress the contained volume 705 of the radioactive fluid container 701 and inject fluid through a fluid transport site 703 on the radioactive fluid container 701 once the container has been loaded into an injection apparatus 751 and the radioactive fluid seal 702 is engaged with an external control mechanism 706.

FIGS. 54–59 disclose one embodiment of radiotherapy source vial 700. FIG. 54 is a partially sectioned view of the vial and radioactive fluid container 701, which includes a radioactive fluid seal 702 therein and further includes a stopper portion 809 and a radioactive fluid seal adaptor 744 that fits securely within, and is affixed to the stopper portion 809. The radioactive fluid container 701 includes a radioactive fluid vial portion 741 that is typically made from glass or another radiation fluid-resistant material such as polycarbonate or a metal, including stainless steel. The radioactive fluid container 701 also includes a container end cap 742 that is glued, crimped, or otherwise attached to the posterior end 810 of the radioactive fluid vial portion 741, which also represents the proximal end of the container as it is loaded into the injector apparatus. A resilient mechanism 717, such as a tension spring 718 of the present invention, is also placed within the radioactive fluid container 701 and attached to radioactive fluid adaptor 744 and container end cap 742 by any well know method including fitting the ends of the tension spring 718 into channels, grooves or apertures 748, 749 (FIG. 57) that are formed in the adaptor 744 and container end cap 742. The container end cap 742 includes a central bore 81 2 through which the external control mechanism 706 is inserted to engage with the radiation fluid seal 702, specifically, the radiation seal adaptor 744. In the illustrated embodiment, the external control mechanism includes a commonly-known quick-release pin 743 that engages the engagement mechanism 704 that forms the radiation seal adaptor 744, which is typically molded from plastic as are most of the custom components of the injector apparatus and other radioactive fluid container 701 components such as the container end cap 742 that do not contact the radioactive fluid. Plastic components that contact radiation fluid can be treated to make them radiation-resistant.

Located at the anterior or distal end 811 of the radioactive fluid container 701 is a fluid transport site 703, such as a rubber septum 707. The septum 707 is secured to the radioactive fluid container 701 by a standard vial cap 745, usually made of metal, which allows the septum 707 to be accessed by a needle. The radioactive fluid seal 702, made of a radiation-resistant material such as butyl, is tightly fitted to the interior of the container and preferably has a double seal 747 to prevent leakage. In the present invention, the distal end 761 of the radioactive fluid seal 702 is shaped to fit within the neck 762 of the radioactive fluid container 701, which permits a more complete evacuation of the container's contents and delivery of a know quantity dosage.

FIG. 55 is partially sectioned view of the present invention in which an external control mechanism is engaged with the radioactive fluid seal 702 and is actuated to advance the radioactive fluid seal 702 from the position shown in FIG. 54. The contained volume 705 of the radioactive fluid container 701 is at an initial volume 716, whereby the contained volume 705 is decreased and the contents of the radioactive fluid container 701 are expelled through the fluid transport site 703. In the illustrated embodiment, the site comprises an external delivery conduit 709 such as a needle cannula 734 which pierces the septum 707 and establishes a passageway 710. As the external control mechanism 706 is withdrawn, the tension spring 717 supplies a pulling force on the radioactive fluid seal 702, allowing it to return to its initial position 813. The spring 717 permits the longitudinal forces acting on the radioactive fluid seal 702 to be more even, helping to prevent the breaking of a seal during advancement or withdrawal. The tension spring should be of sufficient strength to return the tight-fitting radioactive fluid seal 702 to the original position 81 3 without placing undue force on the external control mechanism 406 as it is withdrawn.

Figure 56:
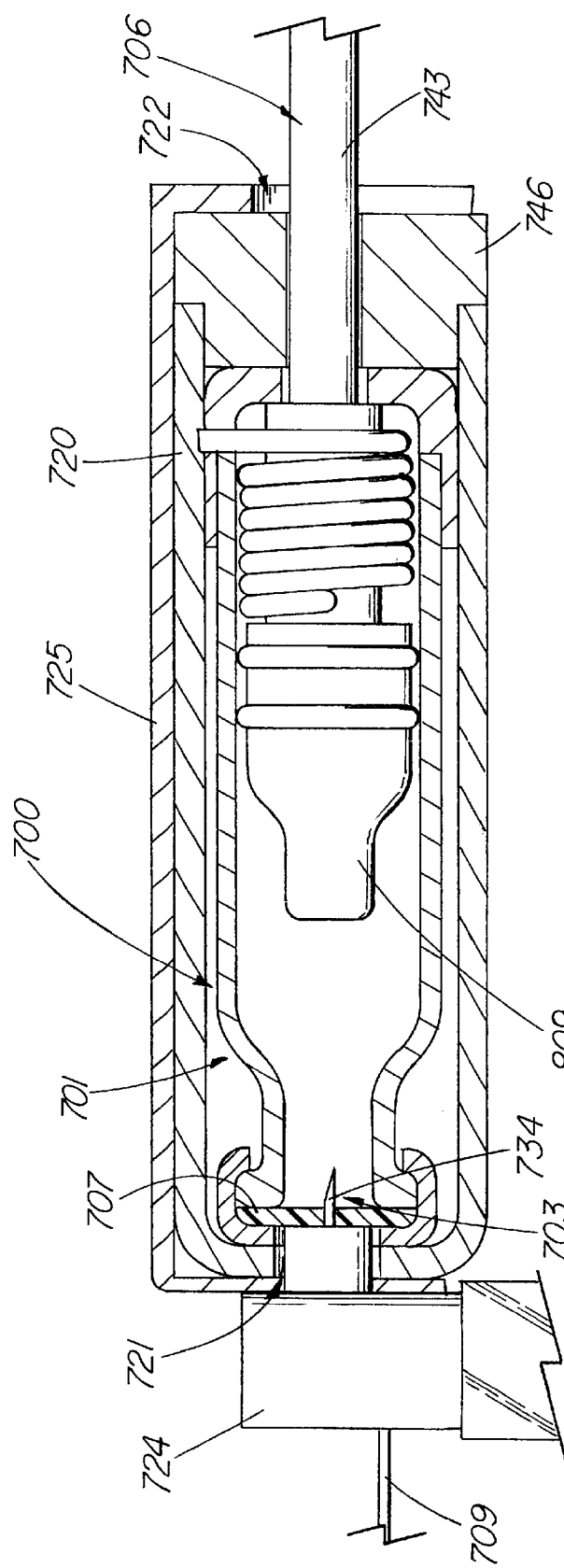
Figure 58:
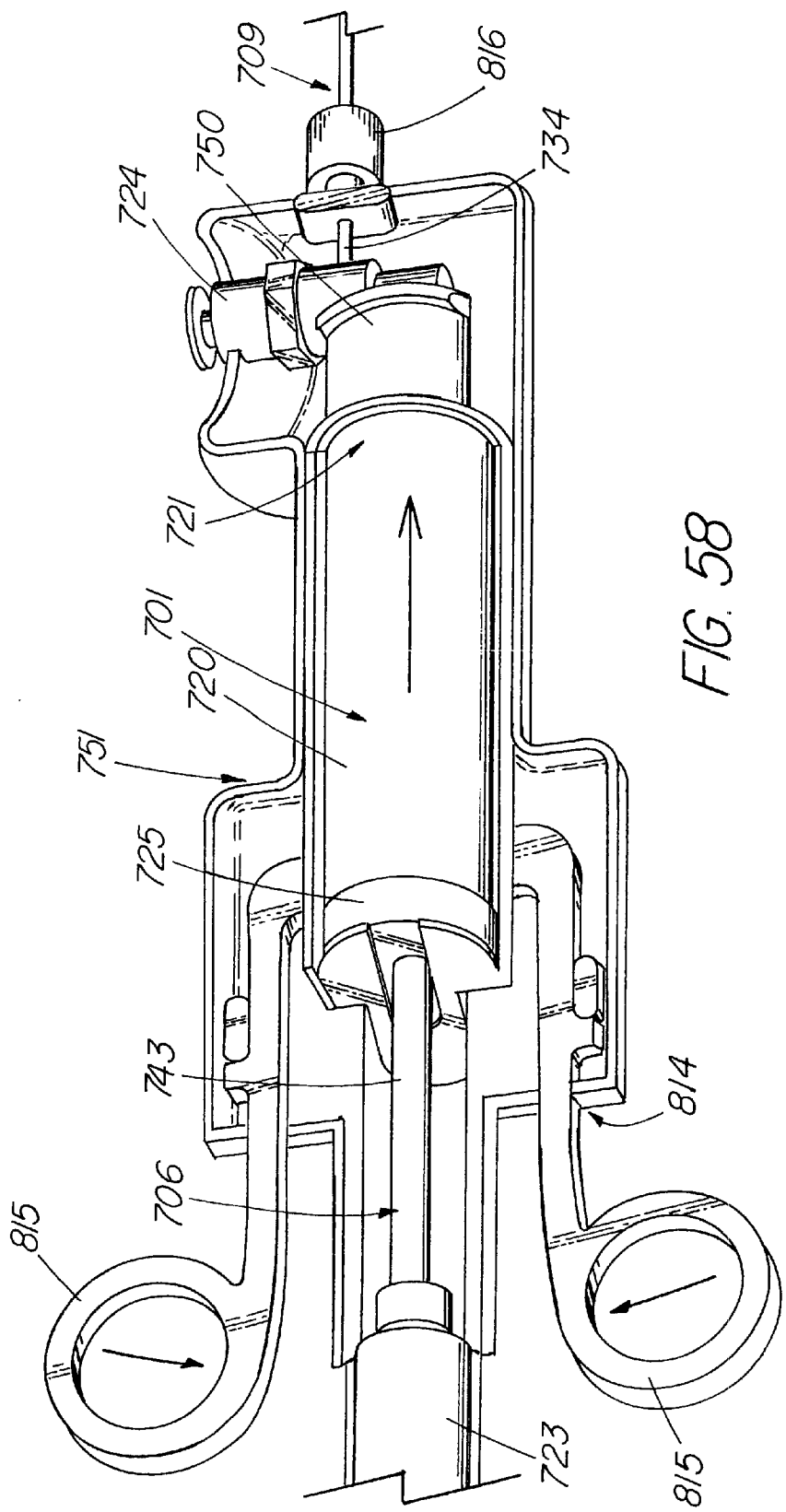
FIGS. 58–59 are partially sectioned isometric views of an embodiment of a injection apparatus and the radiotherapy source vial of FIG. 56.

FIG. 56 is a partially section view side view of the vial of FIG. 54 in which radioactive fluid container 701 is inside an outer shield 720 and loaded into the injection apparatus 751 (FIG. 58). The outer shield 720 is typically made of lead for protection during handling and use and provides both a safe shipping container as well as shielding for the operator during treatment. The outer shield 720 includes a proximal end cap 746 that is removed for loading of the radioactive fluid container 701. The end cap 746 is press-fitted into the outer shield 720 to provide additional shielding to aid in creating a close fit within a carriage 725. The end cap 746 includes an opening 722 through which the external control mechanism 706 is inserted for engagement with radioactive fluid seal 702. The opposite end of the outer shield 720 includes a second opening 721 through which the needle cannula 734 accesses the septum 707 of the radioactive fluid container 701.

Figure 57:
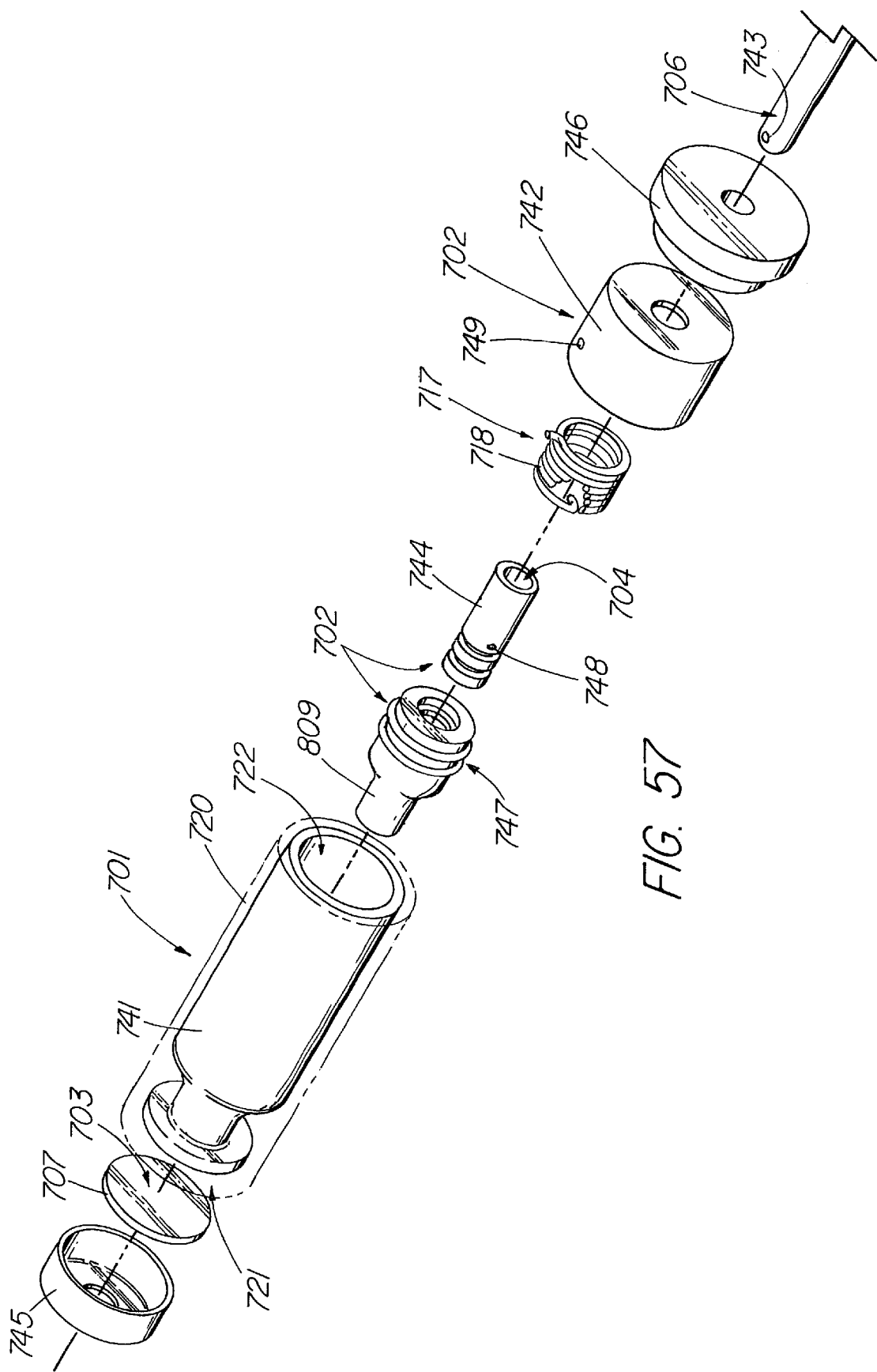
FIG. 57 is an exploded view of a radiotherapy source vial of FIG. 56.
Figure 59:
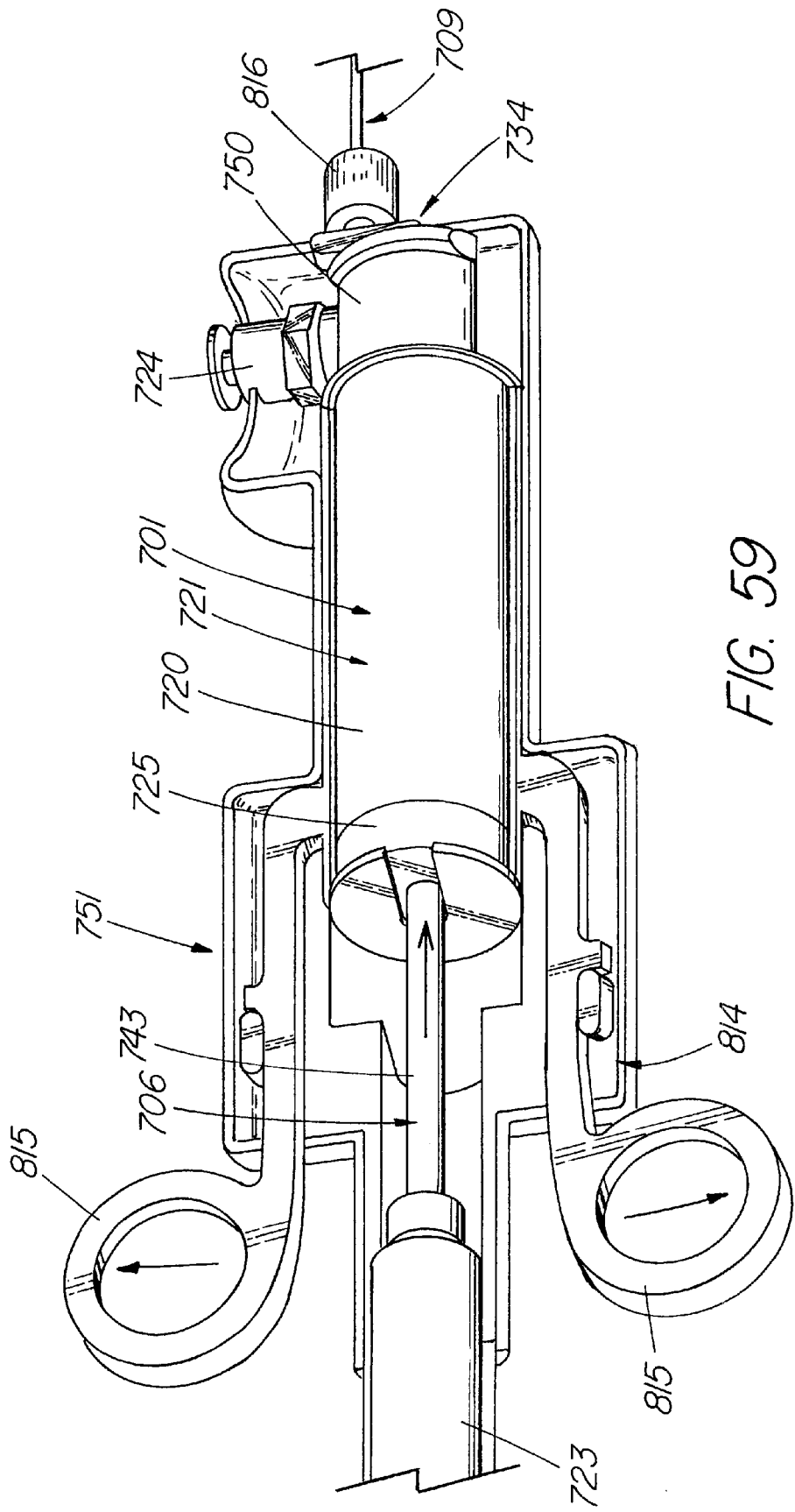

FIG. 57 is an exploded view of the vial of FIG. 54 in which the radioactive fluid container 701 and outer shield 720 are depicted showing the relationship between the different components. FIGS. 58–59 are partially sectioned isometric views of the outer shield 720 of FIG. 57 that encloses the radioactive fluid container 701 loaded and engaged within the injection apparatus 751. In FIG. 58, the carriage 725 is in the loading position and is locked in position by a locking mechanism. In FIG. 59, the handles 815 of the locking mechanism 814 have been depressed inward, allowing the carriage to slide forward and access the needle cannula 734 which is guarded in part by a protective shroud 750 on the carriage 725. The needle cannula is part of a valve assembly 724 that in the illustrated embodiment, is a commercially-available 2-way, 2-position spring return air valve. The external delivery conduit 709 includes an external luer lock fitting 816 for connection to a fluid delivery device, such as a catheter. Once the carriage 725 is locked into place, the handle mechanism 723 can be advanced to advance the external control mechanism 706 and deliver the radioactive fluid.

Figure 60:
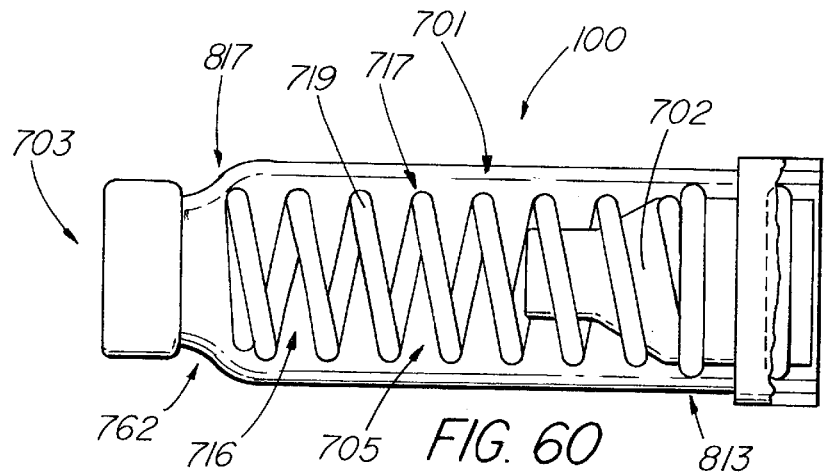
FIG. 60 is a partially sectioned side view of an alternate embodiment of a radiotherapy source vial.

FIG. 60 is a partially sectioned side view of another embodiment of source vial 700 including a radioactive fluid container 701 having a resilient mechanism 717 for urging the radioactive fluid seal 702 toward the initial position 813 establishing an initial volume 716 of the radioactive fluid container 701. In this embodiment, a compression spring 719 is placed within the radioactive fluid container 701 and attached to the radioactive fluid seal 702 in manner similar to the embodiment of FIGS. 55–59. The distal end 817 of the spring is either attached to the radioactive fluid container 701 or rests against the neck 762 of the container. The volume of the vial is adjusted in the same manner as the embodiment of FIGS. 55–59.

Figure 61:
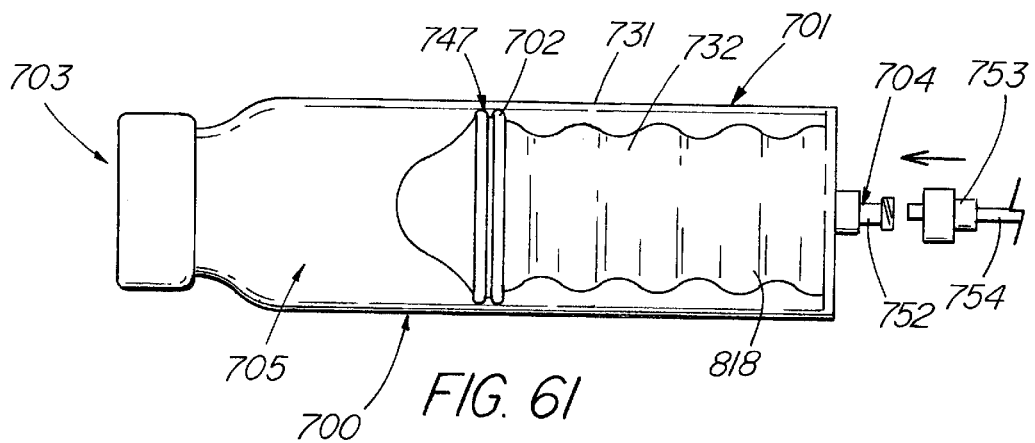
FIG. 61 is a side view of a radiotherapy source vial having an inflatable radioactive fluid seal.
Figure 69:
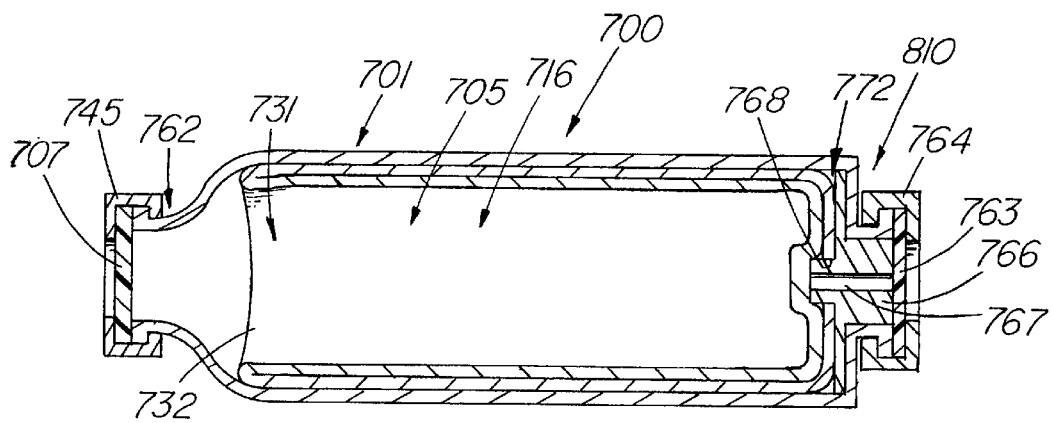
FIGS. 69–70 are partially sectioned side views of an embodiment of a radiotherapy source vial with an inflatable radioactive fluid seal.
Figure 70:
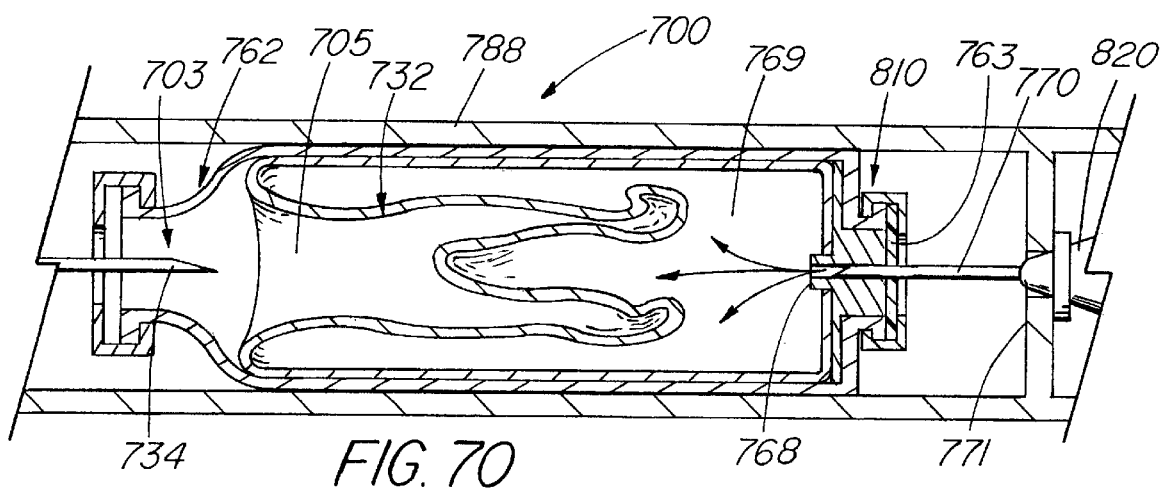

FIGS. 61 and 69–70 are side views of embodiments of source vial 700 including the radioactive fluid container 701 in which the radioactive fluid seal 702 comprises an expandable radioactive fluid seal 731 such as an inflatable bladder 732. FIG. 61 is a pleated bladder 818 that unfolds to fill the contained volume 705 of radioactive fluid container 701 and force the radioactive fluid through the radioactive fluid transport site 703. The pleated bladder includes a double seal 747 near the leading edge to help prevent leakage of the radioactive fluid behind the radioactive fluid seal 702. A Luer fitting 752 on the radioactive fluid container 701 allows connection to a mating luer fitting 753 and a fluid supply line for supplying a fluid, such as saline, to inflate the bladder 818. FIG. 69 is a partially sectioned side view of another embodiment of vial 700 including radioactive fluid container 701 having an inflatable radioactive fluid seal 732. In this embodiment, the inflatable radioactive fluid seal 732 is folded along the interior walls 819 of the radioactive fluid container 701 and attached along the neck 762 of the container such that when inflated, as shown in FIG. 70, the contained volume is compressed both longitudinally and radially until the interior 769 of the inflatable radioactive fluid seal 732 is filled with injected fluid. The fluid for filling the inflatable radioactive fluid seal 732 is supplied by a fluid supply apparatus such as a syringe 820. The infusion needle 770 accesses a second septum 763 at the proximal end 810 of the radioactive fluid container 701. A protective insert 766 is located within the radioactive fluid container 701 at the proximal end 810 and includes a central bore 767 through which the infusion needle 770 enters the interior 769 or contained volume of the radioactive fluid container 701. The protective insert 766 includes a nipple 768 that surrounds the tip of the needle 770 to prevent puncture of the inflatable radioactive fluid seal 732. To further prevent accidental puncture, a stop 771 within the housing 788 or a similar structure contacts a component of the syringe 820 to limit the distal movement of the infusion needle 770.

Figures 62, 63, 64:
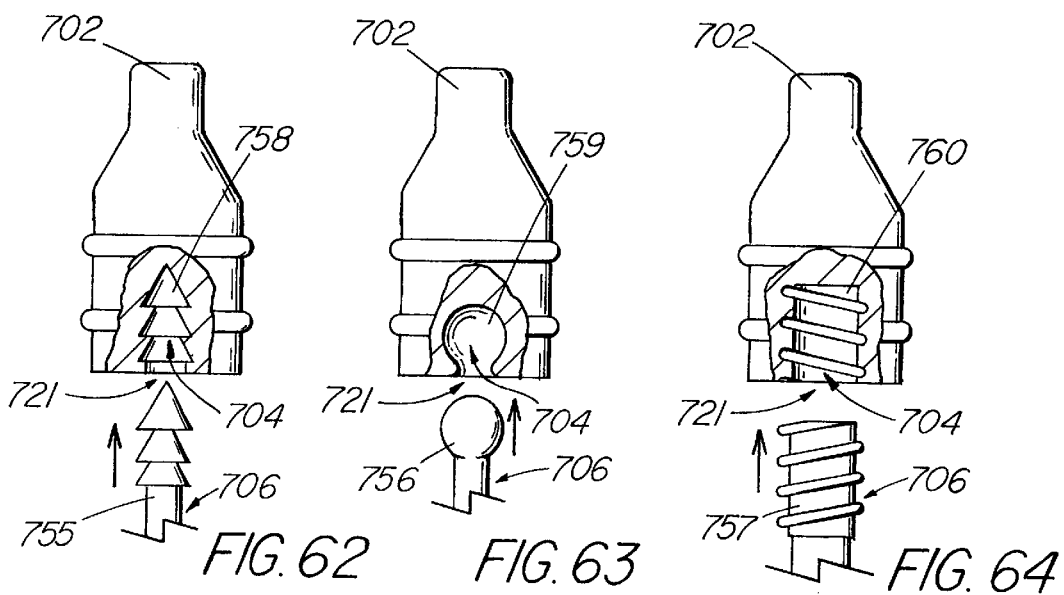
FIGS. 62–64 are partially sectioned side views of engagement mechanism embodiments of a radiotherapy source vial.

FIGS. 62–64 are partially sectioned side views of a few of the many possible alternate embodiments of engagement mechanisms 704 for attaching the external control mechanism 706 to the radioactive fluid seal 701, where a coupling site for coupling to the external control mechanism is located within a receiver. FIG. 62 shows an external control mechanism 706 terminating in a multiple barbed end 755 which press fits into a similarly-shaped receiver 758 on the underside 821 of the radioactive fluid seal 702. In FIG. 63, the terminal end of the external control mechanism is a ball fitting 756 that is inserted into a round receiver 759 on the underside 821 of radioactive fluid seal 702. FIG. 64 shows an external control mechanism 706 having a threaded terminal end 757 that is inserted into a threaded receiver 760 on the underside 821 of radioactive fluid seal 702.

FIGS. 65–68, 71–72 disclose various embodiments of attachment mechanisms 727 for maintaining the radioactive fluid seal 702 in the initial position 813 for maintaining the initial volume 716 of radioactive fluid in the radioactive fluid container 701 during shipping and up until time of deployment. FIG. 65 is a partially sectioned side view of a radioactive fluid container 701 wherein the container end cap 742 has a pair of slots 777 therethrough that align with, and engage a pair of protuberances 776 located on the underside proximal end 818 of the radioactive fluid seal 702. The container end cap 742 is rotatable relative the radioactive fluid container 701. The slots, shown in FIG. 66, each have an enlarged end 823 and a narrowed end 822. The protuberances 776 each have an enlarged terminal portion 824 such that they engage the container end cap 742 when the protuberances 776 are aligned with the enlarged ends 823 of the slots and lock with the container end cap 742 when the vial end cap 742 is rotated counter-clockwise. When the external control mechanism 706 fully engages the engagement mechanism 704 of the radioactive fluid seal 702, it can rotate clockwise to align the protuberances 776 with the enlarged ends 823 of the slots 777 and disengage the locking mechanism 739.

FIGS. 67–68 show another embodiment of attachment mechanism in which a partially threaded rod 736 and partially threaded attachment mechanism 825 are used together as both a locking mechanism 739 and external control mechanism 706. The partially threaded rod 736 has oppositely opposed threaded portions 737 and adjacent unthreaded faces 826 disposed between the threaded portions 737. The partially threaded rod 736 engages the partially threaded attachment mechanism 825 which is integral with the radioactive fluid seal 702 where they align to form a single element with aligned threaded portions 737 and unthreaded faces 826. When the threaded portions of 737 are aligned with the internal threads 827 of container end cap 742, the radioactive fluid seal 702 is engaged in initial position 813. Rotating the partially threaded rod 736 approximately 90° will align the threaded portions 737 with a pair of unthreaded channels 738 which then allow the partially threaded rod 736 and partially threaded attachment mechanism 825 assembly to disengage from the container end cap 742 and slide freely.

Figure 71:
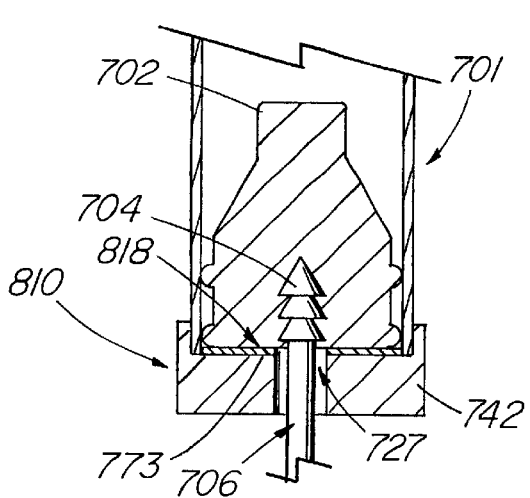
FIGS. 71–72 are partially sectioned side views of attachment mechanism embodiments of a radiotherapy source vial.
Figure 72:
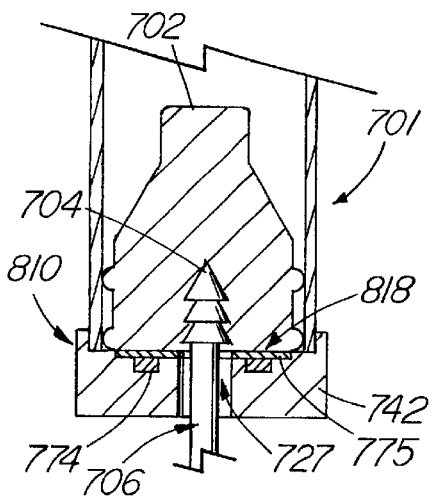

FIGS. 71–72 disclosed two alternate attachment mechanisms 727 embodiments. FIG. 71 is a partially sectioned side view of the posterior end 810 of a radioactive fluid container 701 wherein the attachment mechanism consists of an adhesive layer 773 between the radioactive fluid seal 702 and the container end cap 742. Longitudinal force applied to the radioactive fluid seal 702 by the external control mechanism 706 is sufficient to break the bond of the adhesive layer, thereby allowing the radioactive fluid seal 702 to advance. In FIG. 72, the attachment mechanism comprises a plurality of magnets 774 are located in the container end cap and secure the radioactive fluid seal 702, whose underside 818 has a metallic surface. Like the embodiment of FIG. 71, the external control mechanism 706 supplies the forces to break the attachment. Alternately, the magnets 774 could be incorporated into the radioactive fluid seal 702 with the container end cap 742 being at least partially comprised of metal.

Figure 73:
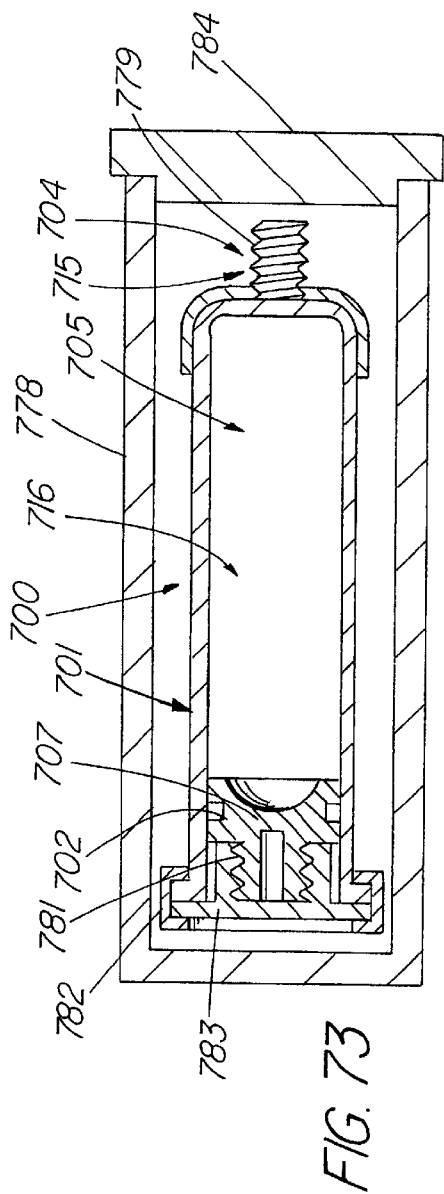
Figure 74:
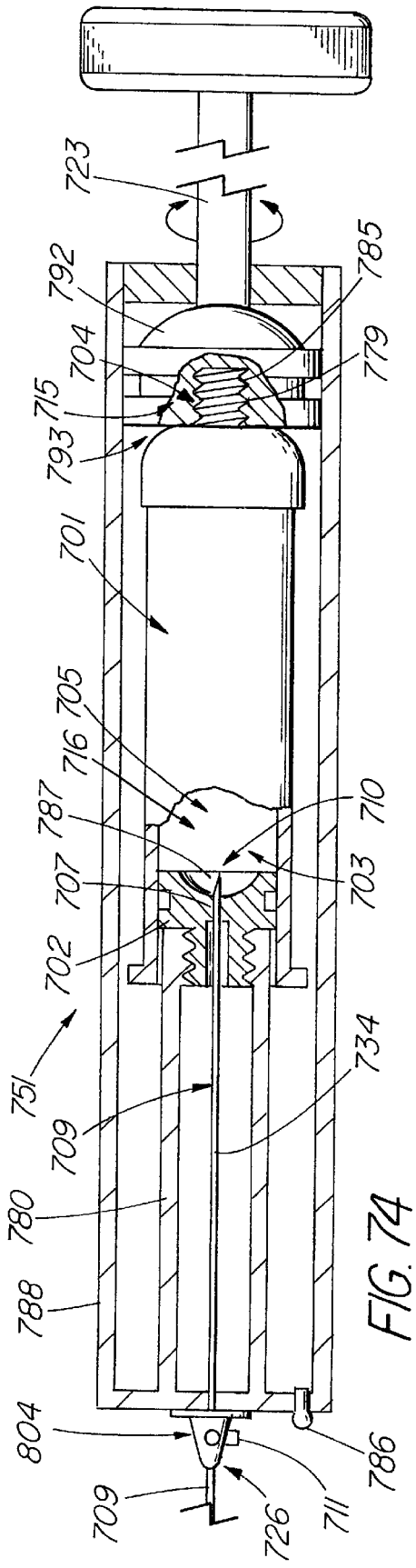

FIGS. 73–75 disclose partially sectioned side views of another embodiment of the injection apparatus 751 for radioactive fluid container 701 with radioactive fluid seal 702 in which the radioactive fluid container 701 itself is advanced by the external control mechanism 706, while the radioactive fluid 701 seal remains stationary. FIG. 73 depicts a partially sectioned side view of the radioactive fluid container 701 as it is shipped prior to incorporation into the injector apparatus. The preloaded radioactive fluid container 701 is shipped in a outer container 778, preferably lead as required by U.S. law. After the radioactive fluid vial 700 is loaded into the injection apparatus 751, a plunger 792 which provides an additional seal to the outer housing 788, is threaded over a threaded coupling 779 on the coupler 715 located at the proximal end 793 of the radioactive fluid container 701 so that the two are engaged. The radioactive fluid seal 702 of the radioactive fluid container 701 is then threaded into the sleeve engagement mechanism located within the inner sleeve 780 of the injector housing 788 which further includes a non-coring needle cannula 734 fixedly attached to the distal end 804 of the housing 788. The inner sleeve 780 includes a hollow tube that is concentrically attached to the distal end of the housing 804. The proximal end 793 of the radioactive fluid container 701 has a threaded coupling 779 to receive the threaded engagement mechanism 704 of the plunger 792, which serves as the external control mechanism 706. The radioactive fluid container 701 is advanced over the inner retention member by rotating the handle mechanism 723. The torque required to thread the source vial plunger over the inner retention member is less than the torque required to rotate the radioactive fluid seal 702 within the radioactive fluid container 701. Therefore, the radioactive fluid seal 702 does not slip and rotate within the radioactive fluid container 701 itself. As the radioactive fluid container 701 is being threaded and advanced into position prior to deployment, the needle cannula 734 pierces the radioactive fluid seal 702 which also functions as the septum 707. An outer valve 711 prevents premature release of the radioactive fluid. The proximal end 793 of the radioactive fluid container 701 includes a coupling 715 that includes a threaded portion 779 that is threaded into a double seal plunger 792 that fits within, and seals the outer housing 788. The outer housing and second plunger serves as a safety barrier to reduce potential leakage of radioactive gas.

FIG. 75 depicts a partially sectioned side view of the injection apparatus 751 of FIG. 74 after deployment. As the plunger 792 is advanced, it advances the radioactive fluid container 701 over the inner sleeve 780 of the outer housing 788. The radioactive fluid seal 702, being threaded to the inner sleeve 780, remains stationary while the radioactive fluid container 701 and plunger 792 are advanced. This compresses the gas, which in turn, is expelled through the needle cannula 734. Leakage of gas within the apparatus can be removed and scavenged via an optional vacuum line attached to a connector port 786 on the apparatus (FIG. 74).

The connection between the source vial cap and the second plunger can be rigid, such as the threaded coupling depicted in the figure, or it can be a flexible/articulating connection such as depicted in FIG. 76. A non-rigid connection can help reduce possible lateral stresses during deployment that could result in fracture of the glass source vial or a break in the seal of the first plunger. The illustrated alternative coupling embodiment includes a coupler 715 mounted to the proximal end 793 of the radioactive fluid container 701 with a tab 789 projecting outward therefrom. The tab, which may be of various shapes and configurations, is comprised of an enlarged distal portion 791 that is inserted into a receiving element 790. As depicted in FIG. 77, the receiving element includes a open-sided slot 794 into which the coupler 715 is inserted. Other alternative embodiments of the coupling mechanism can have at least one of the connector elements capable of being articulated, or made of a flexible material that permits lateral bending. Obviously, the tab 789 and receiver 790 could be located on the plunger 792 and coupler 715, respectively.

Figure 79:
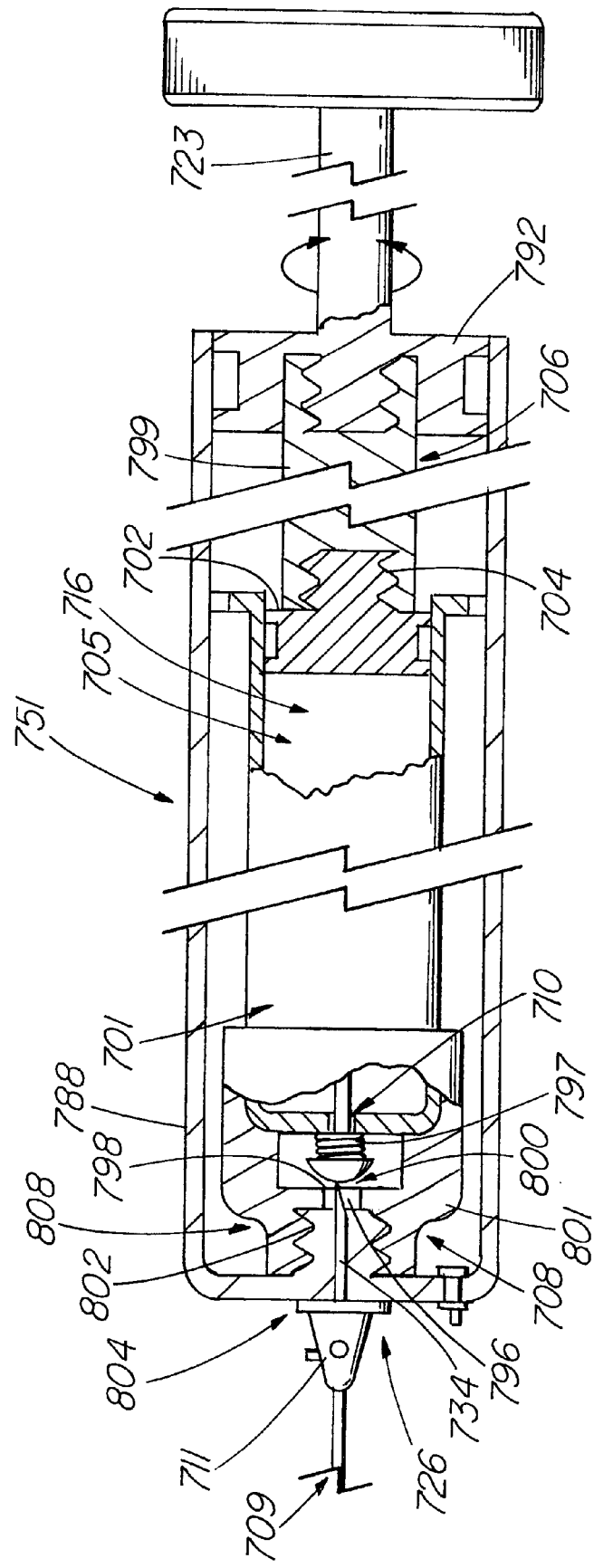
FIG. 79 is a partially sectioned side view of an alternate embodiment of a radiotherapy source vial.

FIGS. 78–79 discloses a partially sectioned side views of another embodiment of the injection apparatus 751 and radioactive fluid container 701 which includes a spring-operated port 708 for evacuating, filling or delivering radioactive fluid to or from the radioactive fluid container 701. FIG. 78 depicts a partially sectioned detail view of the port 708 as shipped prior to incorporation of the vial into the injector apparatus. The valve consists of a gate 796 that is seated against the internal lip 798 located on the inside of the container neck 807. A valve spring 797 urges the gate against the lip and seals the passageway 710 that allows the gas to exit the vial. A temporary cap 806 is threaded into the distal end of the radioactive fluid container 701 during shipping to prevent leakage or accidental engagement with the valve.

FIG. 79 depicts the entire injection apparatus 751 in which the radioactive fluid container 701 of FIG. 78 is engaged in deployment position. The radioactive fluid seal 702 of the source vial is coupled with the external control mechanism 706 which in this embodiment, includes a double-seal plunger 792 and a control mechanism adaptor 799. The control mechanism adaptor 799 is threadedly attached to both the plunger 792 and the radioactive fluid seal 702; however, it should be understood that adaptor 799 could an integral part of the plunger 792, or flexibly attached to the radioactive fluid seal 702 similar to the embodiment of FIG. 76. The radioactive fluid container 701 is threaded over a housing engagement mechanism 802 at the distal end 804 of the outer housing 788 by rotating the handle mechanism 723 of the external control mechanism 706. As the radioactive fluid container advances over the internal coupling, the needle cannula 734 attached to the outer housing 788 presses against the valve gate 796 and opens the passageway 710 by creating a space 800 between the gate 796 and internal lip 798 of the distal end cap 801 that engages the housing engagement mechanism 802. This allows the gas to move out of the vial, through the cannula 734, and into a delivery device once the external valve 711 is opened and the gas is injected.

To compress and deliver the contents of the radioactive fluid container 701, the radioactive fluid seal 702 is advanced using the handle mechanism 723 of the external control mechanism 706. The radioactive fluid container 701 remains stationary against the distal end of the injector apparatus 751 unlike the previous embodiment where the radioactive fluid container 701 itself is advanced.

The spring-actuated port 708 of the radioactive fluid container 701 allows the container to be evacuated and filled without having to compromise the integrity of the septum 707. When a rubber septum is used to seal the contents of the radioactive fluid container 701, two small holes must be made to simultaneous draw out the air in the vial and fill it with radioactive fluid. Although the septum reseals, gas may leak through the minute holes left in the septum.

What is claimed is:

1. A radiotherapy source vial (700) comprising:
   a radioactive fluid container (701) having a contained volume (705) therein;
   an expandable radioactive fluid seal (702, 731) disposed about the radioactive fluid container and being moveable with respect to the radioactive fluid container to change the contained volume therein;
   a radioactive fluid transport site (703) disposed about the radioactive fluid container and communicating with the contained volume and an exterior (726) of the radioactive fluid container; and
   an engagement mechanism (704) fixedly disposed about at least one of the radioactive fluid container and the radioactive fluid seal and fixedly connectable to an external control mechanism (706) external to the radioactive fluid container, whereby the contained volume in the radioactive fluid container can be decreased and increased by actuation of the external control mechanism.

2. The device of claim 1 wherein the radioactive fluid transport site includes a septum (707) that can be pierced by a needle or cannula (734).

3. The device of claim 2 wherein the radioactive fluid transport site is located on the radioactive fluid seal.

4. The device of claim 2 wherein the radioactive fluid container further includes a coupler (715) attached to the radioactive fluid container for engagement with the external control mechanism such that the external mechanism causes movement of the radioactive fluid container relative the radioactive fluid seal, thereby reducing the volume of the radioactive fluid container.

5. The device of claim 1 wherein the radioactive fluid transport site is a port (708), the port adapted to engage an external delivery conduit (709), thereby opening a passage (710) between the external delivery conduit and the radioactive fluid container.

6. The device of claim 1 wherein the radioactive fluid transport site includes a manually operable valve (711).

7. The device of claim 1 wherein the engagement mechanism comprises a receiver for the external control mechanism.

8. The device of claim 7 wherein the receiver includes threads for receiving a threaded external control mechanism.

9. The device of claim 8 wherein the receiver includes at least one coupling site for locking the external control mechanism with the at least one of the radioactive fluid container and the radioactive fluid seal.

10. A radiotherapy source vial (700) comprising:

a radioactive fluid container (701) having a contained volume (705) therein, the contained volume including an initial contained volume (716);

an expandable radioactive fluid seal (702) disposed about the radioactive fluid container and being moveable with respect to the radioactive fluid container to change the contained volume in therein;

a radioactive fluid transport site (703) disposed about the radioactive fluid container and communicating with the contained volume and an exterior (726) of the radioactive fluid container;

an engagement mechanism (704) fixedly disposed about at least one of the radioactive fluid container and the radioactive fluid seal and fixedly connectable to an external control mechanism (706) external to the radioactive fluid container;

a resilient mechanism (717) disposed within the radioactive fluid container and urging the radioactive fluid seal to a position in the radioactive fluid container at which the contained volume is at the initial contained volume;

and whereby the contained volume in the radioactive fluid container can be decreased and increased by actuation of the external control mechanism.

11. The device of claim 10 wherein the resilient mechanism is a spring (718,719).

12. The device of claim 10 further including a outer shield (720) disposed about the radioactive source container and having at least one opening (721,722) for the passage of radioactive fluid and through which the external control mechanism is introduced.

13. The device of claim 12 wherein the outer shield includes a first (721) and a second (722) opening, the first opening located at one end of the outer shield and through which the external control mechanism is inserted to engage with the engagement mechanism on the radiotherapy source vial, the second opening located at another end of the outer shield and through which radioactive fluid is passed therethrough.

14. The device of claim 13 further comprising a radioactive fluid delivery apparatus that includes a handle mechanism (723), a valve assembly (724), and a carriage (725); wherein the outer shield and radioactive source container are placed in the carriage which is slidable relative the valve assembly; the handle mechanism is attachable to the external control mechanism to advance and retract the external control mechanism, whereby adjusting the contained volume of the radioactive source container.

15. A radiotherapy source vial (700) comprising:

a radioactive fluid container (701) having a contained volume (705) therein;

an expandable radioactive fluid seal (702) disposed about the radioactive fluid container and being moveable with respect to the radioactive fluid container to change the contained volume in therein;

a radioactive fluid transport site (703) disposed about the radioactive fluid container and communicating with the contained volume and an exterior (726) of the radioactive fluid container;

an engagement mechanism (704) fixedly disposed about at least one of the radioactive fluid container and the radioactive fluid seal and being at least one of fixedly connected and fixedly connectable to an external control mechanism external to the radioactive fluid container; and an attachment mechanism (727) having an engaged condition, the attachment mechanism disposed on at least one of the radioactive fluid container, the radioactive fluid seal, and the engagement mechanism and when in the engaged condition, maintaining the contained volume fixed, whereby the contained volume in the radioactive fluid container can be decreased and increased by actuation of the external control mechanism.

16. The device of claim 15 wherein the attachment mechanism is a locking mechanism (728) whereby locking features (739) of the radioactive fluid seal engage locking features located about the radioactive fluid container.

17. The device of claim 16 wherein the locking mechanism (728) includes a partially threaded member (736) having threaded portions (737) that can alternately engage the locking features of the radioactive fluid container or rotatably align with unthreaded channels (738) located between the locking features to allow free longitudinal movement.

18. The device of claim 15 wherein the attachment mechanism comprises at least one of an adhesive (729) and a magnet (730).

19. A radiotherapy source vial (700) comprising:

a radioactive fluid container (701) having a contained volume therein;

an expandable radioactive fluid seal (731) disposed within the radioactive fluid container;

a radioactive fluid transport site (703) disposed about the radioactive fluid container and communicating with the contained volume and an exterior of the radioactive fluid container;

an engagement mechanism fixedly disposed about the radioactive fluid container and fixedly connectable to an external control mechanism external to the radioactive fluid container, whereby the contained volume in the radioactive fluid container can be decreased and increased by actuation of the external control mechanism.

20. The device of claim 19 wherein the expandable radioactive fluid seal comprises an inflatable member (732), and the external control mechanism comprises a fluid supply apparatus (733).

\* \* \* \* \*